US008470964B2

(12) United States Patent
Berezin et al.

(10) Patent No.: US 8,470,964 B2
(45) Date of Patent: Jun. 25, 2013

(54) PEPTIDES DERIVED FROM NCAM (FGLS)

(75) Inventors: Vladimir Berezin, Copenhagen N (DK); Elisabeth Bock, Charlottenlund (DK); Soren Ebdrup, Roskilde (DK); Boris Klementiev, Birkerød (DK)

(73) Assignee: Enkam Pharmaceuticals A/S, Copenhagen N (DK)

( * ) Notice: Subject to any disclaimer, the term of this patent is extended or adjusted under 35 U.S.C. 154(b) by 51 days.

(21) Appl. No.: 12/745,129

(22) PCT Filed: Nov. 28, 2008

(86) PCT No.: PCT/DK2008/050282
§ 371 (c)(1),
(2), (4) Date: Nov. 16, 2010

(87) PCT Pub. No.: WO2009/068042
PCT Pub. Date: Jun. 4, 2009

(65) Prior Publication Data
US 2011/0098225 A1    Apr. 28, 2011

Related U.S. Application Data

(60) Provisional application No. 61/032,683, filed on Feb. 29, 2008.

(30) Foreign Application Priority Data

Nov. 28, 2007  (DK) .................. 2007 01691
Dec. 18, 2007  (DK) .................. 2007 01813

(51) Int. Cl.
*C07K 2/00*      (2006.01)
*A61K 38/00*     (2006.01)

(52) U.S. Cl.
USPC .......................................... 530/300; 514/1.1

(58) Field of Classification Search
None
See application file for complete search history.

(56) References Cited

U.S. PATENT DOCUMENTS

| | | | |
|---|---|---|---|
| 4,599,311 | A | 7/1986 | Kawasaki |
| 4,683,202 | A | 7/1987 | Mullis |
| 5,693,488 | A | 12/1997 | Fang et al. |
| 5,837,813 | A | 11/1998 | Ruoslahti et al. |
| 5,840,689 | A | 11/1998 | Daniloff et al. |
| 6,313,265 | B1 | 11/2001 | Phillips et al. |
| 6,576,607 | B1 | 6/2003 | Schachner |
| 6,749,850 | B1 | 6/2004 | Finkelstein et al. |
| 7,167,819 | B1 | 1/2007 | Gibson et al. |
| 7,504,490 | B1 | 3/2009 | Weinstock et al. |
| 2009/0105149 | A1 | 4/2009 | Albrechtsen et al. |
| 2009/1005149 | | 4/2009 | Albrechtsen at al. |
| 2009/0305951 | A1 | 12/2009 | Kiselyov et al. |

FOREIGN PATENT DOCUMENTS

| | | |
|---|---|---|
| WO | WO 00/18791 | 4/2000 |
| WO | WO 00/24770 | 5/2000 |
| WO | WO 01/16166 | 3/2001 |
| WO | WO 01/96364 | 12/2001 |
| WO | WO 03/016351 | 2/2003 |
| WO | WO 2004/056865 | 7/2004 |
| WO | 2005014623 A2 | 2/2005 |

OTHER PUBLICATIONS

USPTO, Final Rejection, mailed Apr. 1, 2011 on Application of Kiselyov, U.S. Appl. No. 12/435,043.
USPTO, Final Rejection, mailed Jan. 18, 2011 on Application of Albrechtsen, U.S. Appl. No. 10/567,365.
Alber et al., "Nucleotide Sequence of the Triose Phosphate Isomerase Gene of *Saccharomyces cerevisiae*", *J. of Molecular and Applied Genetics*, vol. 1, No. 5, pp. 419-434, 1982.
Altman et al., "Postnatal Development of Locomotion in the Laboratory Rat", *Anim. Behav.*, vol. 23, pp. 896-920, 1975.
Beaucage et al., "Deoxynucleoside Phosphoramidites—A New Class of Key Intermediates forDeoxypolynucleotide Synthesis", *Tetrahedron Letters*, vol. 22, No. 20, pp. 1859-1862, 1981.
Berezin et al., "NCAM Mimetic Peptides—Pharmacological and Therapeutic Potential", *J. of Molecular Neuroscience*, vol. 22, pp. 33-39, 2004.
Berezin, et al., "The neural cell adhesion molecule", *Current Opinion in Drug Discovery & Development*, vol. 3, pp. 605-609, 2000.
Bruses, et al., "Roles, regulation, and mechanism of polysialic acid function during neural development", *Biochemie*, vol. 83, pp. 635-643, 2001.
Cambon et al., "A Synthetic Neural Cell Adhesion Molecule Mimetic Peptide Promotes Synaptogenesis. Enhances Presynaptic Function, and Facilitates Memory Consolidation", *J. of Neuroscience*, vol. 24, No. 17, pp. 4197-4204, Apr. 28, 2004.
Cambon, et al., "Post-training administration of a synthetic peptide ligand of the neural cell adhesion molecule, C3d, attenuates long-term expression of contextual fear conditioning", *Neuroscience*, vol. 122, pp. 183-191, 2003.
Cancilla et al., "Fibroblast growth factor receptors and their ligands in the adult rat kidney", *Kidney International*, vol. 60, pp. 147-155, 2001.
Castelnau et al., "Prion Protein Gene Expression in Cultured Astrocytes Treated by Recombinant Growth Hormone and Insulin-like Growth Factor", *Experimental Neurology*, vol. 130, pp. 407-410, 1994.

(Continued)

*Primary Examiner* — John Ulm
(74) *Attorney, Agent, or Firm* — Iver P. Cooper

(57) ABSTRACT

The present invention relates to novel compounds comprising at most 13 contiguous amino acid residues derived from the fibronectin type 3,11 module of neural cell adhesion molecule (NCAM), or a variant or fragment thereof, capable of interacting with an FGFR and thereby the compounds are capable of inducing differentiation, modulating proliferation, stimulate regeneration, neuronal plasticity or survival of cells. Further, the present invention relates to the use of the compounds for production of a medicament for treatment of conditions and diseases, in which NCAM or FGFR play a prominent role.

22 Claims, 15 Drawing Sheets

OTHER PUBLICATIONS

Cerbone et al., "Behavioral Habituation to Spatial Novelty: Interference and Noninterference Studies", *Neuroscience and Behavioral Reviews*, vol. 18, No. 4, pp. 497-518, 1994.

Chan, et al., "Identification, classification, and analysis of beta-bulges in proteins", *Protein Science*, vol. 2, pp. 1574-1589, 1993.

Cheng et al., "NGF and bFGF Protect Rat Hippocampal and Human Cortical Neurons against Hypoglycemic Damage by Stabilizing Calcium Homeostasis", *Neuron*, vol. 7, pp. 1031-1041, Dec. 1991.

Clayton et al., "Noradrenergic Receptor Blockade of the NTS Attenuates the Mnemonic Effects of Epinephrine in an Appetitive Light-Dark Discrimination Learning Task", *Neurobiology of Learning and Memory*, vol. 74, pp. 135-145, 2000.

Cordero et al., "Prior exposure to a single stress session facilitates subsequent contextual fear conditioning in rats—Evidence for a role of Corticosterone", *Hormones and Behavior*, vol. 44, pp. 338-345, 2003.

Corsaro et al., "Enhancing the Efficiency of DNA-Mediated Gene Transfer in Mammalian Cells", *Somatic Cell Genetics*, vol. 7, No. 5, pp. 603-616, 1981.

Cotman et al., "Cell Adhesion Molecules in Neural Plasticity and Pathology: Similar Mechanisms, Distinct Organizations", *Progress in Neurobiology*, vol. 55, pp. 659-669, 1998.

Cremer, et al., "NCAM is essential for axonal growth and fasciculation in the hippocampus", *Mol. Cell Neurosci.*, vol. 8, pp. 323-335, 1997.

D'Mello et al., "Induction of apoptosis in cerebellar granule neurons by low potassium: Inhibition of death by insulin-like growth factor I and cAMP", *Proc. Natl. Acad. Sci. USA*, vol. 90, pp. 10989-10993, Dec. 1993.

D'Mello, et al., "Insulin-like growth factor and potassium depolarization maintain neuronal survival by distinct pathways: possible involvement of PI 3-kinase in IGF-1 signaling", *J. Neurosci.*, vol. 17, pp. 1548-1560, 1997.

Dantzer, et al., "Modulation of social memory in male rats by neurohypophyseal peptides", *Psychopharmacology*, vol. 91, pp. 363-368, 1987.

Defoort et al., "A rational design of synthetic peptide vaccine with a built-in adjuvant", *Int. J.Peptide Protein Res.*, vol. 40, pp. 214-221, 1992.

Delobette et al., "In vitro aggregation facilitates β-amyloid peptide-(25-35)-induced amnesia in the rat", *European J. of Pharmacology*, vol. 319, pp. 1-4, 1997.

Dickson, et al., "Human Muscle Neural Cell Adhesion Molecule (N-CAM): Identification of a Muscle-Specific Sequence in the Extracellular Domain", *Cell*, vol. 50, pp. 1119-1130, Sep. 25, 1987.

Ditlevsen, et al., "The role of phosphatidylinositol 3-kinase in neural cell adhesion molecule-mediated neuronal differentiation and survival", *Journal of Neurochemisry*, vol. 84, pp. 546-556, 2003.

Doherty, et al., "CAM-FGF Receptor Interactions: A Model for Axonal Growth", *Mol. Cell Neurosci.*, vol. 8, pp. 99-111, 1996.

Drejer et al., "Selection of a Pure Cerebellar Granule Cell Culture by Kainate Treatment", *Neurochemical Research*, vol. 14, No. 8, pp. 751-754, 1989.

Drijfhout et al., "A new synthetic functionalized antigen carrier", *Int. J. Peptide Protein Res.*, vol. 37, No. 27-32, 1991.

Dryland et al., "Peptide Synthesis. Part 8. A System for Solid-phase Synthesis Under Low Pressure Continuous Flow Conditions", *J. Chem. Soc Perkin Trans. I*, pp. 125-137, 1986.

Dzhandzhugazyan, et al., "Demonstration of (Ca(2+)-Mg2+)-ATPase activity of the neural cell adhesion molecule", *FEBS Lett.*, vol. 336(2), pp. 279-283, Dec. 27, 1993.

Dzhandzhugazyan, et al., "Demonstration of an extracellular ATP-binding site in NCAM: functional implications of nucleotide binding", *Biochemistry*, vol. 36(49), pp. 15381-15395, Dec. 9, 1997.

Eilers, et al., "Role of the Jun kinase pathway in the regulation of c-Jun expression and apoptosis in sympathetic neurons", *J. Neurosci.*, vol. 18(5), pp. 1713-1724, Mar. 1, 1998.

Eldadah et al., "Ribozyme-Mediated Inhibition of Caspase-3 Protects Cerebellar Granule Cells from Apoptosis Induced by Serum-Potassium Deprivation", *J. Neuroscience*, vol. 20, No. 1, pp. 179-186, Jan. 1, 2000.

Eriksson, et al., "Refinement of the structure of human basic fibroblast growth factor at 1.6 A resolution and analysis of presumed heparin binding sites by selenate substitution", *Protein Sci*, vol. 2(8), pp. 1274-1284, Aug. 1993.

Frei, et al., "Different Extracellular Domains of the Neural Cell Adhesion Molecule (N-CAM) Are Involved in Different Functions", *Journal of Cell Biology*, vol. 118, No. 1, pp. 177-194, Jul. 1992.

Furka, et al., "General method for rapid synthesis of multicomponent peptide mixtures", *Int J Pept Protein Res.*, vol. 37(6), pp. 487-493, Jun. 1991.

Goodwin et al., "A simple procedure for solid-phase synthesis of peptide nucleic acids with N-terminal cysteine", *Bioorganic & Medicinal Chemistry Letters*, vol. 8, pp. 2231-2234, 1998.

Graham et al., "A New Technique for the Assay of Infectivity of Human Adenovirus 5 DNA", *Virology*, vol. 52, pp. 456-467, 1973.

Hart et al., "Attenuation of FGF signaling in mouse β-cells leads to diabetes", *Nature*. vol. 408, pp. 864-868, Dec. 14, 2000.

Hartz, et al., "A synthetic peptide ligand of NCAM affects exploratory behaviour and memory in rodents", *Pharmacology, Biochemistry and Behavior*, vol. 75, pp. 861-867, 2003.

Hatten, et al., "In vitro neurite extension by granule neurons is dependent upon astroglial-derived fibroblast growth factor", *Dev Biol*, vol. 125(2), pp. 280-289, Feb. 1988.

Henck et al., "Growth and Development in Rats Given Recombinant Human Epidermal Growth Factor $_{1-48}$ as Neonates", *Toxicological Sciences*, vol. 62, pp. 80-91, 2001.

Hitzeman et al., "Isolation and Characterization of the Yeast 3-Phosphoglycerokinase Gene (PGK) by an Immunological Screening Technique", *J. of Biol. Chem.*, vol. 255, No. 24, pp. 12073-12080, Dec. 25, 1980.

Horstkorte, et al., "The fourth immunoglobulin-like domain of NCAM contains a carbohydrate recognition domain for oligomannosidic glycans implicated in association with L1 and neurite outgrowth", *J. Cell Biol.*, vol. 121(6), pp. 1409-1421, Jun. 1993.

Hulley, et al., "L1 neural cell adhesion molecule is a survival factor for fetal dopaminergic neurons", *J Neurosci Res.*, vol. 53(2), pp. 129-134, Jul. 15, 1998.

Jensen, et al., "Structure and interactions of NCAM modules 1 and 2, basic elements in neural cell adhesion", *Nat Struct Biol*, vol. 6, pp. 486-493. May 5, 1999.

Jessen, et al., "Neural Cell Adhesion Molecule-Mediated Neurite Outgrowth Is Repressed by Overexpression of HES-1", *Journal of Neuroscience Research*, vol. 71, pp. 1-6, 2003.

Jessen, et al., The transcription factors CREB and c-Fos Play key roles in NCAM-mediated neuritogenesis in PC12-E2 cells. *Journal of Neurochemistry*, vol. 79, pp. 1149-1160, 2001.

Jungnickel et al., "Fibroblast growth factor receptor 3 signaling regulates injury-related effects in the peripheral nervous system", *Mol. Cell. Neurosci.*, vol. 25, pp. 21-29, 2004.

Kasper, et al., "Structural basis of cell-cell adhesion by NCAM", *Nat Struct Biol*, vol. 7(5), pp. 389-393, May 2000.

Kasper, et al., "Functional Characterization of NCAM Fibronection Type III Domains: Demonstration of Modulatory Effects of the Proline-Rich Sequence Encoded by Alternatively Spliced Exons a and AAG", *Journal of Neuroscience Research*, vol. 46, pp. 173-186, 1996.

Kaufman et al., "Amplification and Expression of Sequences Cotransfected with a Modular Dihydrofolate Reductase Complementary DNA Gene", *J. Mol. Biol.*, vol. 159, pp. 601-621, 1982.

Kimler et al., "Ovulatory delay alters postnatal growth, behavior, and brain structure in rats", Developmental Brain Research, vol. 107, pp. 49-55, 1998.

Kiryushko et al., "A Synthetic Peptide Ligand of Neural Cell Adhesion Molecule (NCAM), C3d, Promotes Neuroitogenesis and Synaptogenesis and Modulates Presynaptic Function in Primary Cultures of Rat Hippocampal Neurons", *J. of Biol. Chem.*, vol. 278, No. 14, pp. 12325-12334, Apr. 4, 2003.

Kiselyov et al., :Structural Basis for a Direct Interaction between FGFR1 and NCAM and Evidence for a Regulatory Role of ATP, *Structure*, vol. 11, pp. 691-701, Jun. 2003.

Kiselyov, et al., "The first immunoglobulin-like neural cell adhesion molecule (NCAM) domain is involved in double-reciprocal interaction with the second immunoglobulin-like NCAM domain and in heparin binding", *J Biol Chem*, vol. 272(15), pp. 10125-10134, Apr. 11, 1997.

Kiselyov, et al. Abstract, "Structure of the second fibronectin type III module of NCAM. Identification of a neuritogenic site" *European Journal of Neuroscience*, vol. 12, No. 11, 2000.

Klementiev, et al., "A neural cell adhesion molecule-derived peptide reduces neuropathological signs and cognitive impairment induced by Abeta(25-35)", *Neuroscience*, vol. 145, pp. 209-224, 2007.

Klementiev, et al., "A peptide agonist of the neural cell adhesion molecule (NCAM), C3, protects against developmental defects induced by a teratogen pyrimethamine", *Int. J. Devl Neuroscience*, vol. 20, pp. 527-536, 2002.

Kogan et al., "Long-Term Memory Underlying Hippocampus-Dependent Social Recognition in Mice", *Hippocampus*, vol. 10, pp. 47-56, 2000.

Kolkova, et al., "Neural Cell Adhesion Molecule-Stimulated Neurite Outgrowth Depends on Activation of Protein Kinase C and the Ras-Mitogen-Activated Protein Kinase Pathway", *The Journal of Neuroscience*, vol. 20(6), pp. 2238-2246, Mar. 15, 2000.

Kruman et al., "Evidence that 4-Hydroxynonenal Mediates Oxidative Stress-Induced Neuronal Apoptosis", *J. of Neurosci.*, vol. 17, No. 13, pp. 5089-5100, Jul. 1, 1997.

Laake et al., "A simple in vitro model of ischemia based on hippocampal slice cultures and propidium iodide fluorescence", *Brain Research Protocols*, vol. 4, pp. 173-184, 1999.

Lam, et al., "A new type of synthetic peptide library for identifying ligand-binding activity", *Nature*, vol. 354, pp. 82-84, Nov. 7, 1991.

Loyter et al., "Mechanisms of DNA uptake by mammalian cells: Fate of exogenously added DNA monitored by the use of fluorescent dyes", *Proc. Natl. Acad. Sci. USA*, vol. 79, pp. 422-426, Jan. 1982.

Lu et al., "Chemically unambiguous peptide immunogen: preparation, orientation and antigenicity of purified peptide conjugated to the multiple antigen peptide system", *Mol. Immunol.*, vol. 28, No. 6, pp. 623-630, 1991.

Maar et al., "Characterization of Microwell Cultures of Dissociated Brain Tissue for Studies of Cell-Cell Interactions", *J. of Neurosci. Res.*, vol. 47, pp. 163-172, 1997.

Malich et al., "The sensitivity and specificity of the MTS tetrazolium assay for detecting the in vitro cytotoxicity of the 20 chemicals using human cell lines", *Toxicology*, vol. 124, pp. 179-192, 1997.

Matthes et al., "Simultaneous rapid chemical synthesis of over one hundred oligonucleotides on a microscale", *EMBO J.*, vol. 3, No. 4, pp. 801-805, 1984.

Maurice et al., "Amnesia induced in mice by centrally administered β-amyloid peptides involves cholinergic dysfunction", *Brain Research*, vol. 706, pp. 181-193, 1996.

McKnight et al., "Identification and molecular analysis of a third *Aspergillus nidulans* alcohol dehydrogenase gene", *EMBO J.*, vol. 4, No. 8, pp. 2093-2099, 1985.

Merle et al., "Basic Fibroblast Growth Factor Activates Calcium Channels in Neonatal Rat Cardiomyocytes", *J. of Biol. Chem.*, vol. 270, pp. 17361-17367, Jul. 21, 1995.

Ming, et al., "A fibronectin fragment inhibits tumor growth, angiogenesis, and metasis", *Proc. Nat. Acad. Sci. (USA)*, vol. 98, No. 2, pp. 620-624, Jan. 16, 2001.

Miyamoto et al., "Autocrine FGF Signaling is Required for Vascular Smooth Muscle Cell Survival In Vitro", *J. of Cell. Physiology*, vol. 177, pp. 58-67, 1998.

Morris, "Developments of a water-maze procedure for studying spatial learning in a rat", *J. of Neurosci. Methods*, vol. 11, pp. 47-60, 1984.

Neumann et al., "Gene transfer into mouse lyoma cells by electroporation in high electric fields", *EMBO J.*, vol. 1, No. 7, pp. 841-845, 1982.

Ozen et al., "Role of Fibroblast Growth Factor Receptor Signaling in Prostate Cancer Cell Survival", *J. of Natl. Cancer Inst.*, vol. 93, No. 23, pp. 1783-1790, Dec. 5, 2001.

Palmiter et al., "Metallothionein-Human GH Fusion Genes Stimulate Growth of Mice", *Science*, No. 222, pp. 809-814, 1983.

Pedersen, et al., "Neuritogenic and Survival-Promoting Effects of the P2 Peptide Derived From a Homphilic Binding Site in the Neural Cell Adhesion Molecule", *Journal of Neuroscience Research*, vol. 75, pp. 55-65, 2004.

Pigino et al., "Presenilin-1 Mutations Reduce Cytoskeletal Association, Deregulate Neurite Growth, and Potentiate Neuronal Dystrophy and Tau Phosphorylation", *J. of Neurosci.*, vol. 21, No. 3, pp. 834-842, Feb. 1, 2001.

Povlsen et al., "Intracellular Signaling by the Neural Cell Adhesion Molecule", *Neurochemical Research*, vol. 28, No. 1, pp. 127-141, Jan. 2003.

Powers et al., "Fibroblast growth factors, their receptors and signaling", *Endocrine-Related Cancer*, vol. 7, pp. 165-197, 2000.

Rajagopalan et al., "Use of the 3-nitro-2-pyridine sulfenyl protecting group to introduce $N^\varepsilon$-branching at lysine during solid-phase peptide synthesis", *Int. J. Peptide Protein Res.*, vol. 45, pp. 173-179, 1995.

Ranheim, et al., "Homophilic adhesion mediated by the neural cell adhesion molecule involves multiple immunoglobulin domains", *Proc Natl Acad Sci USA*, vol. 93(9), pp. 4071-4075, Apr. 30, 1996.

Rao, et al., "Identification of a peptide sequence involved in homophilic binding in the neural cell adhesion molecule", *J Cell Biol*, vol. 118(4), pp. 937-949, Aug. 1992.

Rao, et al., "Mechanism of homophilic binding mediated by the neural cell adhesion molecule NCAM. Evidence for isologous interaction", *J Biol Chem.*, vol. 269(44), pp. 27540-27548, Nov. 4, 1994.

Retzler, et al., Analysis of neurocan structures interacting with the neural cell adhesion molecule N-CAM:, *J Biol Chem.*, 271(44):27304-10, Nov. 1, 1996.

Reuss et al., "Fibroblast growth factors and their receptors in the central nervous system", *Cell Tissue Res.*, vol. 313, pp. 139-157, 2003.

Rønn et al., "Identification of a neuritogenic ligand of the neural cell adhesion molecule using a combinatorial library of synthetic peptides", *Nature Biotechnology*, vol. 17, pp. 1000-1005, Oct. 1999.

Rønn et al., "The neural cell adhesion molecule in synaptic plasticity and ageing", *Int. J. Devl. Neuroscience*, vol. 18, pp. 193-199, 2000.

Rønn et al., "A simple procedure for quantification of neurite outgrowth based on stereological principles", *J. of Neuroscience Methods*, vol. 100, pp. 25-32, 2000.

Ronn, et al., "NCAM-antibodies modulate induction of long-term potentiation in rat hippocampal CA1", *Brain Res.*, vol. 677(1), pp. 145-151, Apr. 17, 1995.

Rønn et al., "Characterization of a novel NCAM ligand with a stimulatory effect on neurite outgrowth identified by screening a combinatorial peptide library", *European Journal of Neuroscience*, vol. 16, pp. 1720-1730, 2002.

Rønn et al., "Increased intracellular calcium is required for neurite outgrowth induced by a synthetic peptide ligand of NCAM", *FEBS Letters*, vol. 519, pp. 60-66, 2002.

Rønn et al., "Neurite Outgrowth Induced by a Synthetic Peptide Ligand of Neural Cell Adhesion Molecule Requires Fibroblast Growth Factor Receptor Activation", *Journal of Neurochemistry*, vol. 75, pp. 665-671, 2000.

Rougon, et al., "New insights into the diversity and function of neuronal immunoglobulin superfamily molecules", *Annu Rev Neurosci.*, vol. 26, pp. 207-238, 2003.

Russell et al., "DNA sequences of two yeast promoter-up mutants", *Nature*, vol. 304, No. 18, pp. 652-654, Aug. 1983.

Saiki et al., "Primer-Directed Enzymatic Amplification of DNA with a Thermostable DNA Polymerase", *Science*, vol. 239, pp. 487-491, 1988.

Sarin et al., "Quantitative Monitoring of Solid-Phase Peptide Synthesis by the Ninhydrin Reaction", *Analytical Biochemistry*, vol. 117, pp. 147-157, 1981.

Secher, et al., "A neural cell adhesion molecule-derived fibroblast growth factor receptor agonist, the FGL-peptide, promotes early postnatal sensorimotor development and enhances social memory retention", *Neuroscience*, vol. 141, pp. 1289-1299, 2006.

Sibanda, et al., "A systematic classification with applications to modeling by homology, electron density fitting and protein engineering", *J Mol Biol*, vol. 206(4), pp. 759-777, Apr. 20, 1989.

Skaper, et al., "Neurotrophins rescue cerebellar granule neurons from oxidative stress-mediated apoptotic death: selective involvement of phosphatidylinositol 3-kinase and the mitogen-activated protein kinsae pathway", *J Neurochem.*, vol. 70(5), pp. 1859-1868, May 1998.

Skladchikova, et al., "Extracellular adenosine triphosphate affects neural cell adhesion molecule (NCAM)-mediated cell adhesion and neurite outgrowth", *J Neurosci Res*, vol. 57(2), pp. 207-218, Jul. 15, 1999.

Slavin, "Fibroblast Growth Factors: At The Heart of Angiogenesis", *Cell Biology International*, vol. 19, No. 5, pp. 431-444, 1995.

Soroka, et al., "Structure and Interactions of NCAM Igl-2-3 Suggest a Novel Zipper Mechanism for Homophilic Adhesion", *Structure*, vol. 10, pp. 1291-1301, Oct. 2003.

Soroka, et al., "Induction of Neuronal Differentiation by a Peptide Corresponding to the Homophilic Binding Site of the second Ig Module of the Neural Cell Adhesion Molecule", *Journal of Biological Chemistry*, vol. 277, No. 27, pp. 24676-24683, Jul. 5, 2002.

Southern et al., "Transformation of Mammalian Cells to Antibiotic Resistance with a Bacterial Gene Under Control of the SV40 Early Region Promoter", *J. of Molecular and Applied Genetics*, vol. 1, pp. 327-341, 1982.

Stahlhut et al., "NCAM-Fibronectin-Type-III-Domain Substrata With and Without a Six-Amino-Acid-Long-Proline-Rich Insert Increase the Dendritic and Axonal Arborization of Spinal Motoneurons", *J. of Neuroscience Research*, vol. 48, pp. 112-121, 1997.

Stoppini et al., "A simple method for organotypic cultures of nervous tissue", *J. of Neuroscience Methods*, vol. 37, pp. 173-182, 1991.

Subramani et al., Expression of the Mouse Dihydrofolate Reductase Complementary Deoxyribonucleic Acid in Simian Virus 40 Vectors, *Molecular and Cellular Biology*, pp. 854-864, Sep. 1981.

Van Kampen, et al., "AR-R 17779 improves social recognition in rats by activation of nicotinic alpha7 receptors", *Psychopharmacology*, vol. 172, pp. 375-383, 2004.

Vasudevan et al., "Muscarinic acetylcholine receptor produced in recombinant baculovirus infected Sf9 insect cells couples with endogenous G-proteins to activate ion channels", *FEBS Letters*, vol. 311, No. 1, pp. 7-11, Oct. 1992.

Vianna et al., "Learning & Memory. Role of Hippocampal Signaling Pathways in Long-Term Memory Formation of a Nonassociative Learning Task in the Rat", *Learn Mem.*, vol. 7, pp. 333-340, 2000.

Villalba, et al., "Pituitary adenylate cyclase-activating polypeptide (PACAP-38) protects cerebellar granule neurons from apoptosis by activating the mitogen-activated protein kinase (MAP kinase) pathway", *J Neurosci*, vol. 17(1), pp. 83-90, Jan. 1, 1997.

Walmod et al., "Automated in Vitro Screening of Teratogens", *Toxicology and Applied Pharmacology*, vol. 181, pp. 1-15, 2002.

Walmod, et al., "Zippers make signals: NCAM-mediated molecular interactions and signal transduction", *Neurochem Res.*, vol. 29, pp. 2015-2035, 2004.

Welzl et al., "Cell Adhesion Molecules: Key Players in Memory Consolidation?", *News Physiol. Sci.*, vol. 18, pp. 147-150, 2003.

Wigler et al., "Biochemical Transfer of Single-Copy Eucaryotic Genes Using Total Cellular DNA as Donor", *Cell*, vol. 14, pp. 725-731, Jul. 1978.

Wilmot, et al., "Beta-turns and their distortions: a proposed new nomenclature", *Protein Eng.*, vol. 3(6), pp. 479-493, May 1990.

Yao, et al. "Requirement for phosphatidylinositol-3 kinase in the prevention of apoptosis by nerve growth factor", *Science*, vol. 267(5206), pp. 2003-2006, Mar. 31, 1995.

Ye et al., "Increase of Acidic Fibroblast Growth Factor in the Brains of Hamsters Infected with Either 263K or 139H Strains of Scrapie", *J. of Molecular Neuroscience*, vol. 18, pp. 179-188, 2002.

Zhu et al., "Evidendce that FGF receptor signaling is necessary for endoderm-regulated development of precardiac mesoderm", *Mechanisms of Ageing and Development*, vol. 108, pp. 77-85, 1999.

Kiselyov, Amendment, filed Dec. 16, 2010 on Application of Kiselyov, U.S. Appl. No. 12/435,043.

USPTO, Final Rejection, mailed Sep. 16, 2010 on Application of Kiselyov, U.S. Appl. No. 12/435,043.

USPTO, Rejection, mailed Dec. 23, 2009 on Application of Kiselyov, U.S. Appl. No. 12/435,043.

Albrechtsen, Amendment, mailed Nov. 8, 2010 on Application of Albrechtsen, U.S. Appl. No. 10/567,365.

USPTO, Rejection, mailed Aug. 31, 2010 on Application of Albrechtsen, U.S. Appl. No. 10/567,365.

PEPTIDES DERIVED FROM NCAM (FGLS)

FIELD OF INVENTION

The present invention relates to novel compounds comprising at most 13 contiguous amino acid residues derived from the fibronectin type 3,II module of neural cell adhesion molecule (NCAM), or a variant or fragment thereof, capable of interacting with an FGFR and thereby the compounds are capable of inducing differentiation, modulating proliferation, stimulate regeneration, neuronal plasticity and/or survival of cells. Further, the present invention relates to the use of said compounds for production of a medicament for treatment of conditions and diseases, wherein NCAM and/or FGFR play a prominent role.

BACKGROUND OF INVENTION

NCAM is a cell surface glycoprotein belonging to the Ig superfamily of CAMs (for review see Kiselyov et al., 2005). NCAM can be expressed as three major isoforms (A, B and C) with differences in the cytoplasmic domain. The extracellular part of NCAM is identical for the three isoforms and consists of five Ig-like and two fibronectin type III (F3) modules. NCAM is widely expressed during embryonic development, whereas in the adult organism it is mainly found in tissues of neural origin. NCAM plays a major role during development of the nervous system, mediating adhesion between neural cells and stimulating neurite outgrowth and fasciculation, promoting cell survival and synaptic plasticity (Cremer et al., 1997; Berezin et al., 2000; Bruses and Rutishauser, 2001; Rougon and Hobert, 2003; Walmod et al., 2004). NCAM mediates cell-cell adhesion through homophilic binding and regulates neurite outgrowth via FGFR (Doherty and Walsh, 1996; Kiselyov et al., 2003 and 2005). The FGFR site involved in binding to NCAM has been mapped to the Ig3 module, and the corresponding site in NCAM—to the second F3 module (Kiselyov et al., 2003). This interaction leads to activation of intracellular signaling cascades mediating cell differentiation and survival.

The identified NCAM fragment having the sequence EVYVVAENQQGKSKA (FGL peptide) involved in the direct interaction between NCAM and FGFR has recently been suggested as a new candidate compound for the treatment of a variety of pathologic disorders where the stimulation of activity of FGFR may play the key role (WO 03/016351). It is located in F3, II and binds and activates the FGF receptors 1 and 2, promotes neurotigenesis, and neuronal cell survival in vitro (Kiselyev et al., 2003; Neiiendam et al., 2004) and improves long-term memory in rat (Cambon et al., 2004). The FGL peptide has also been shown to promote neuronal survival and rescue the cognitive deficit in a rat model of amyloid-beta peptide induced neurotoxicity. (Klementiev et al. 2007).

SUMMARY OF INVENTION

The present invention concerns a compound comprising at the most 13 amino acids derived from the fibronectin type 3,II module of neural cell adhesion molecule (NCAM), capable of interacting with an FGFR.

A compound of the invention is capable of inducing differentiation, modulating proliferation, stimulate regeneration, neuronal plasticity and/or survival of cells.

Another aspect of the invention relates to use of a compound of the invention as medicaments and for the preparation of medicaments for treatment of a condition or disease wherein FGFR and/or NCAM play a role in pathology or recovery from disease.

Further, the present invention describes a pharmaceutical composition comprising at least one compound of the invention.

Still, in another aspect a compound of the invention may be used for the production of an antibody.

A: The graph illustrates the results obtained in the SRT 5 hour after the last administration. In each experimental group results were obtained from 7 to 10 rats. Significant memory enhancing effects were detected in all peptide groups $*P<0.05$; $P<0.01$; $*P<0.001$.

B: The graph illustrates the results obtained in the SRT 77 hour after the last administration. In each experimental group data were obtained from 8 to 10 rats. Significant memory enhancing effects were detected for the FGLs, and $FGL_L$ peptide groups $**P<0.01$ FIG. 6. Effects of FGLs on spatial learning in the Morris Water Maze. Rats received FGLs or vehicle subcutaneously as a single dose of 2.5 mg/kg 5, 3 and 1 day prior to first test (trials 1-4 in above graph). The second test (trials 5-8 in above graph) took place the day after the first test. The results were analysed using analysis of variance (ANOVA) and Student's t-test. Data are mean escape latency(s) (±SEM) to find the platform over the 2 training days (t1-t4). $*p<0.05$, when compared with the Vehicle/Control group at the same time point.

Figure 7:
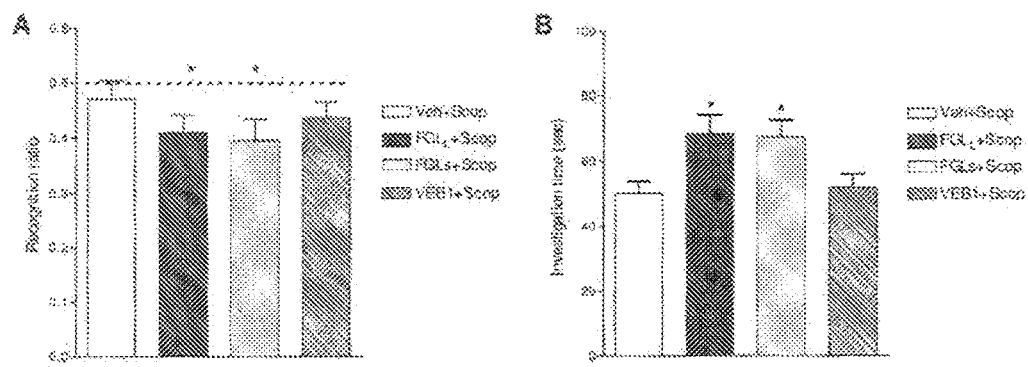

FIG. 7. Effects of subcutaneous administration of $FGL_L$ FGLs, and VEB1 (2 administrations with a 19 hours interval, at 8 mg/kg) on the scopolamine induced social amnesia as evaluated in the Social Recognition Test (SRT). The rats were tested with the initial trial of SRT performed 5 h after the last administration of peptide/vehicle and 30 minutes after scopolamine (0.01 mg/kg s.c.) administration. The juvenile rat was presented twice with an inter-trial interval of 15 minutes.

A—Recognition ratios (RR) of rats treated with scopolamine and vehicle (Veh) or scopolamine and one of the three peptides as detailed above. Results are shown as Mean and SEM of recognition ratio (RR). A RR value significantly below 0.5 indicates social memory. Comparisons of RR values to a hypothetical value 0.50 were carried out using one-sample t-test. In each experimental group data were obtained from 10 rats. Significant effects against scopolamine induced social amnesia were detected for the $FGL_L$, and FGLs peptide groups $*P<0.05$.

B—Cumulative investigation time (T1, in seconds) during the first trial of the SRT of rats treated with scopolamine and vehicle (Veh) or scopolamine and one of the three peptides as detailed above. Results are shown as Mean and SEM of T1. Comparison between groups were carried out by ANOVA followed by Dunnett Multiple Comparison Test. In each experimental group data were obtained from 10 rats. Rats of the $FGL_L$, and FGLs peptide groups showed a significantly longer T1 than rats treated with vehicle. $*P<0.05$.

Figure 8:
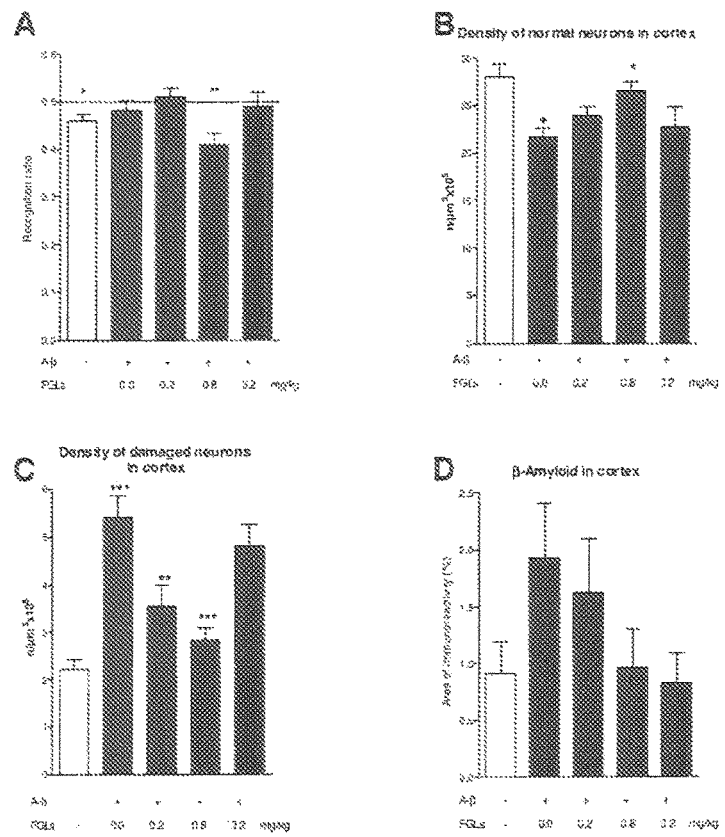

FIG. 8. The effect of FGLs (administered subcutaneously at the stated doses), or vehicle on the development of cognitive impairment (deficit in short-term social memory) and neurodegeneration after (25-35) β-amyloid (A-β) fragment neurointoxication. Comparisons of RR values to a hypothetical value 0.50 were carried using one-sample t-test. Inter-group comparisons between A-β groups were carried out using One Way ANOVA and Newman-Keuls post-hoc test and comparison between A-β vehicle and sham-operated animals by un-paired t-test.

A: The effect of FGLs administration on the β-amyloid neurotoxicity induced deficit on performance in the Social Recognition Test. Results are shown as Mean and SEM of recognition ratio (RR). 10-12 animals per groups. A RR value significantly below 0.5 indicates social memory. $*p<0.05$, $**p<0.01$ when compared to the A-β/V group.

B: The effect of FGLs administration on the β-amyloid neurotoxicity induced decrease in density of intact neurons in the cingulate cortex. 7-8 rats per group. $+/*p<0.05$ when compared with the A-β/V group.

C: The effect of FGLs administration on the β-amyloid neurotoxicity induced induced increase in density of damaged neurons in the cingulate cortex. 7-8 rats per group. $p<0.01+++/*p<0.001$ when compared with the A-β/V group.

D: The effect of FGLs administration on the β-amyloid neurotoxicity induced increase of amyloid burden (% of A-β/V control value) in the cingulate cortex. 7-8 rats per group. Neither the lesion, nor the peptide had significant effects.

Figure 9:
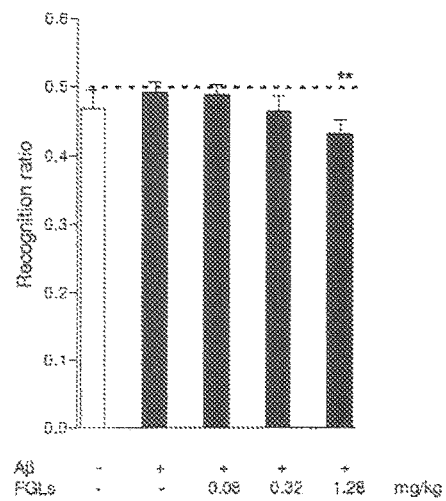

FIG. 9. Effects of intranasal administration of FGLs on the β-amyloid neurotoxicity induced deficit on performance in the Social Recognition Test. Rats received an intranasal administration of FGLs at the stated doses or vehicle daily at days 7 to 21 after i.c.v. administration of the (25-35) β-amyloid (A-β) fragment. 8-10 animals per group. Results are expressed as Means and SEM of Recognition Ratio and analyzed by one-sample t-test: $**p<0.05$.

Figure 10:
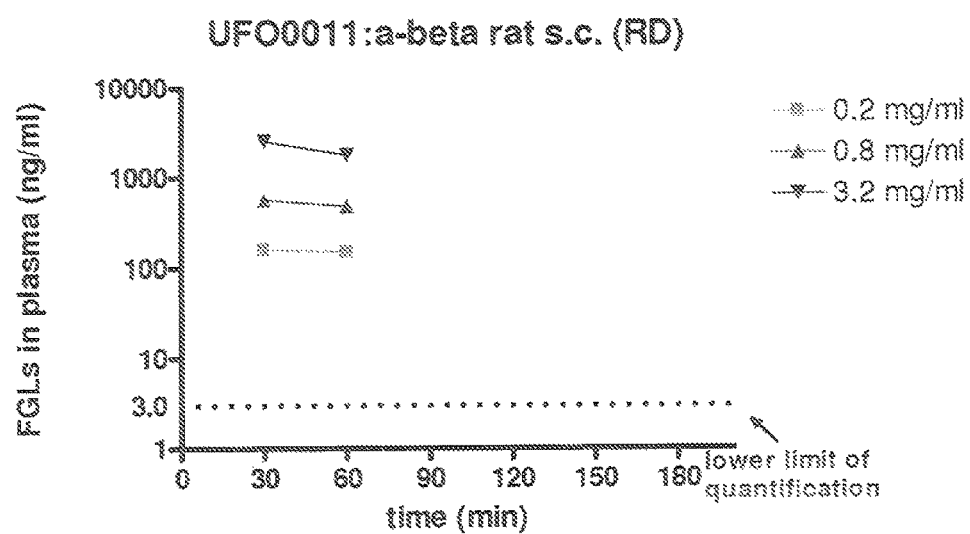

FIG. 10. Concentration of FGLs in blood plasma of rat after intranasal administration of FGLs at 0.2, 0.8 or 3.2 mg/kg daily at days 7 to 21, after i.c.v. administration of the (25-35) β-amyloid (A-β) fragment. Blood samples were obtained 30 min and 60 min after the last administration and FGLs concentration were measured.

Figure 11:
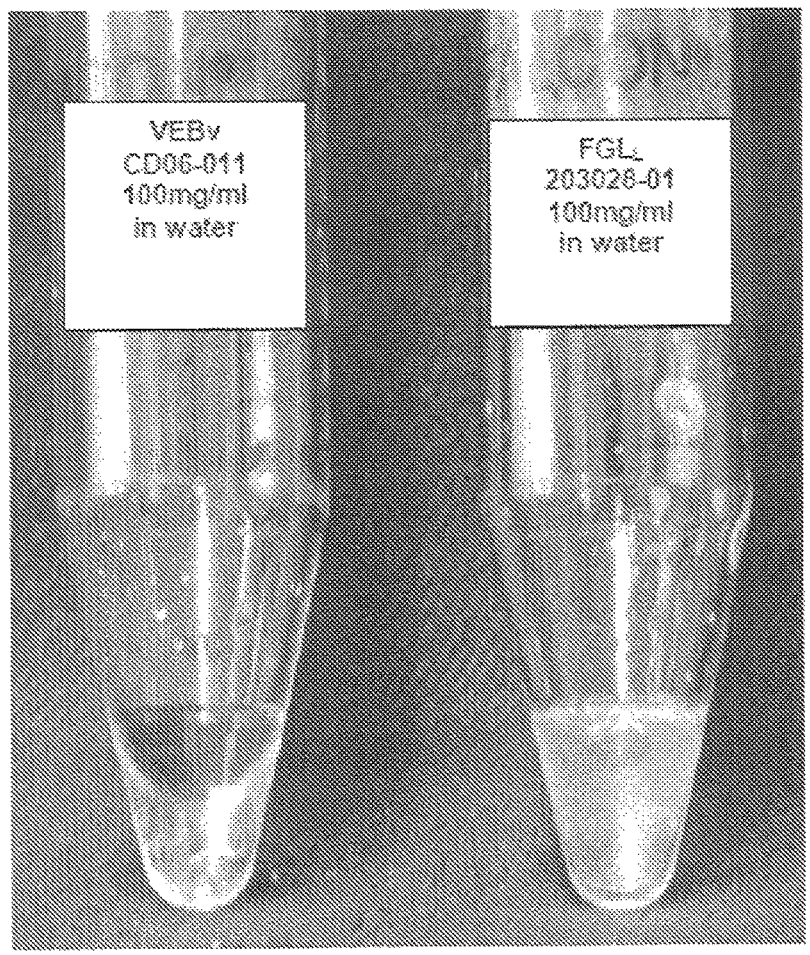

FIG. 11. Visual appearance of $FGL_L$ and FGLs. 100 mg of $FGL_L$ and FGLs, respectively were diluted in 1 ml water at room temperature for visual inspection.

Figure 12:
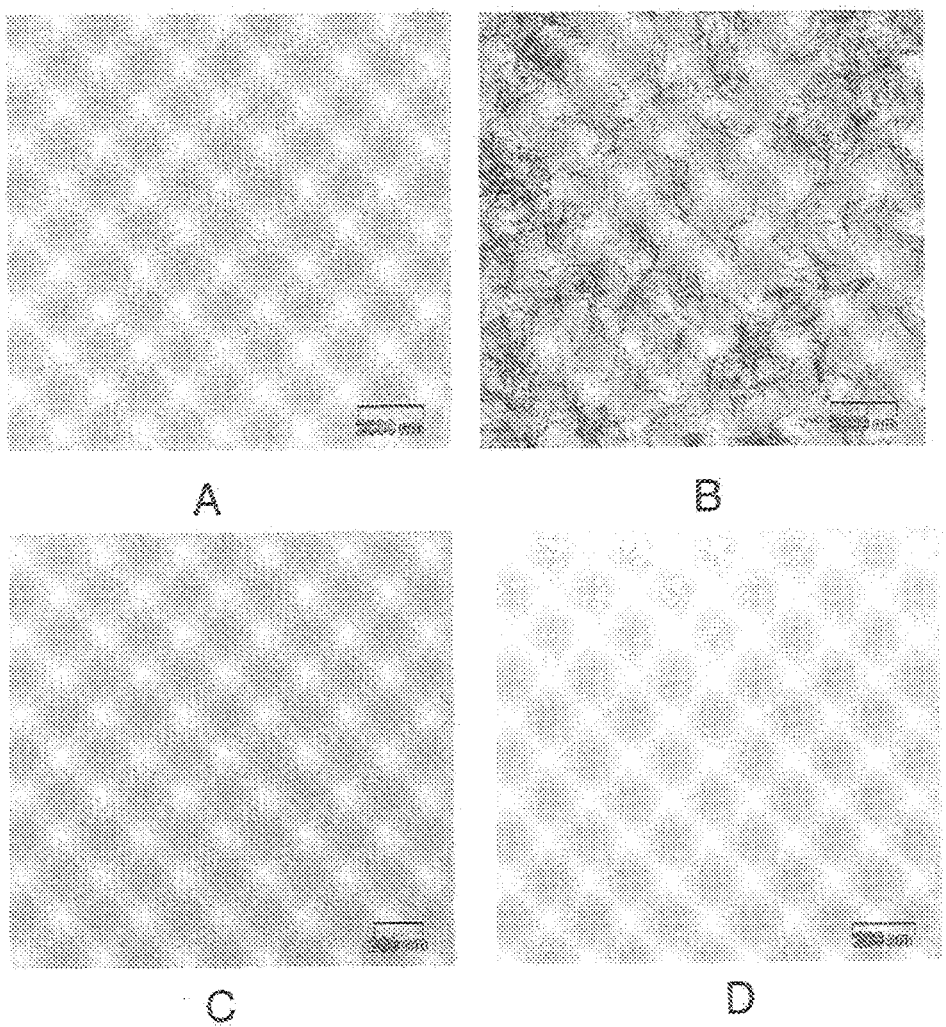

FIG. 12. Light microscopy picture of $FGL_L$ and FGLs diluted in water and PBS. 5 mg of $FGL_L$ and FGLs respectively were diluted in 1 ml water or PBS at room temperature. A. 5 mg/ml $FGL_L$ in water, B. 5 mg/ml $FGL_L$ in PBS, C. 5 mg/ml FGLs in water, D. 5 mg/ml FGLs in PBS.

Figure 13:
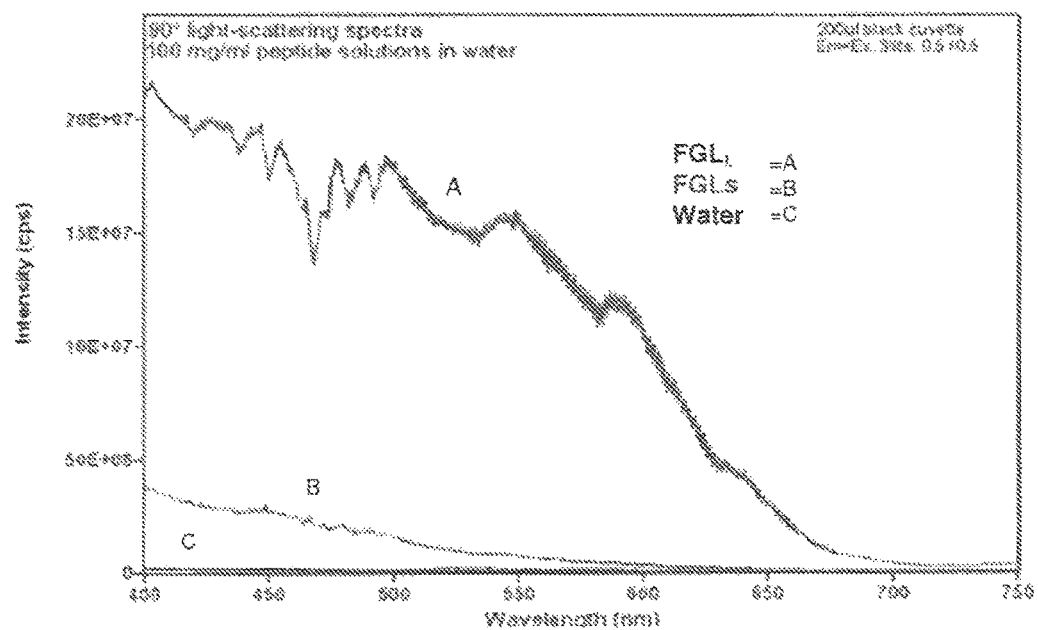

FIG. 13. 90° light-scattering spectra of 100 mg/ml FGLL, FGLs in water. A. $FGF_L$, B. FGFs, C. water.

Figure 14:
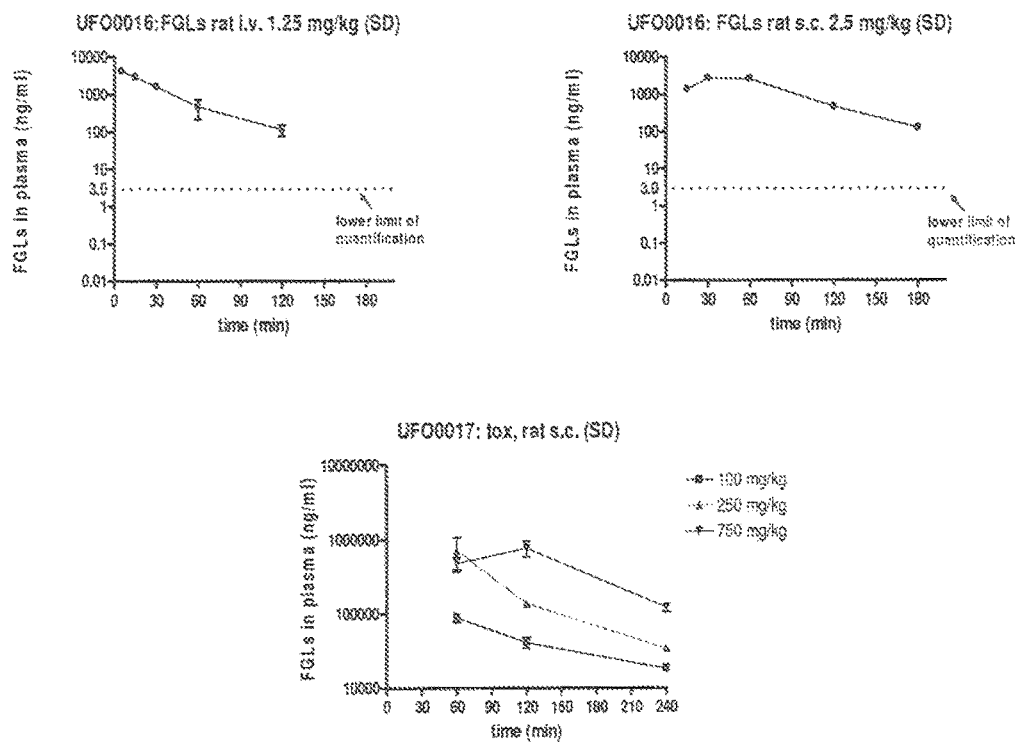

FIG. 14. Concentration of FGLs in blood plasma of rat after peptide administration. Rats were administered 1.25 mg/kg i.v or 2.5 mg/kg s.c. Blood samples were taken at different time points after administration and FGLs concentration were measured.

Figure 15:
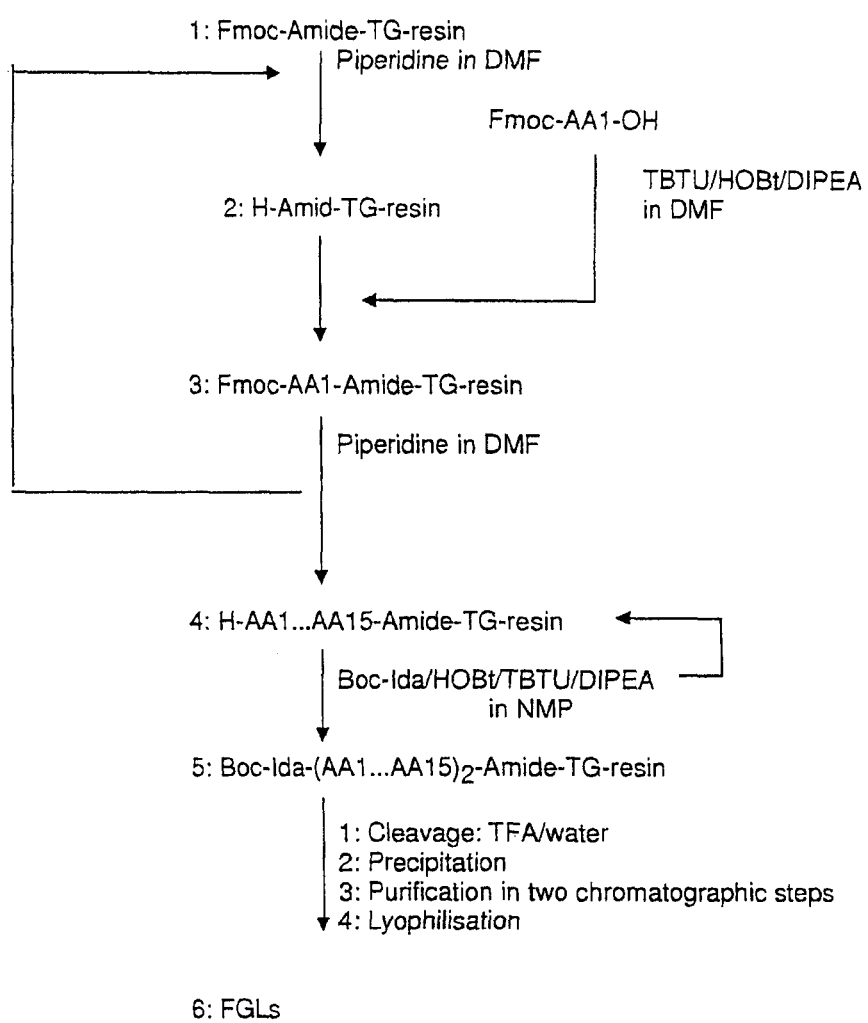

FIG. 15. Flowchart showing the preparation of FGLs.

DETAILED DESCRIPTION OF THE INVENTION

The present invention discloses truncated forms of $FGL_L$ with an improved effect, which is more soluble and thereby more easy to formulate. The novel compounds according to the invention, comprises at the most 13 amino acids derived from the same motif on the F3, II module as $FGL_L$.

The removal of amino acids from $FGL_L$ from the N-terminal end leads to a more soluble peptide that does not show potential for aggregation, which allows it to be formulated for and administered both intranasally and subcutaneously.

A compound according to the invention comprise a contiguous amino acid sequence of at the most 13 amino acids which is derived from the fibronectin type 3, II module of NCAM, or a variant or fragment thereof.

In a preferred embodiment the compounds according to the invention may comprise a contiguous amino acid sequence comprising at the most 13 amino acids which is derived from NCAM. Accordingly, in this embodiment the amino acid sequence according to the invention may be selected from the following amino acid sequences:

```
VAENQQGKSKA        SEQ ID NO: 1
EVVAENQQGKSKA      SEQ ID NO: 2
NVVAENQQGKSKA      SEQ ID NO: 3
NSVAENQQGKSKA.     SEQ ID NO: 4
```

In the present context the standard one-letter code for amino acid residues as well as the standard three-letter code are applied. Abbreviations for amino acids are in accordance with the recommendations in the IUPAC-IUB Joint Commission on Biochemical Nomenclature Eur. J. Biochem, 1984, vol. 184, pp 9-37. Throughout the description and claims either the three letter code or the one letter code for natural amino acids are used. Where the L or D form has not been specified it is to be understood that the amino acid in question has the natural L form, cf. Pure & Appl. Chem. Vol. (56(5) pp 595-624 (1984) or the D form, so that the peptides formed may be constituted of amino acids of L form, D form, or a sequence of mixed L forms and D forms.

Where nothing is specified it is to be understood that the C-terminal amino acid of a peptide for use according to the invention exists as the free carboxylic acid, this may also be specified as "—OH". However, the C-terminal amino acid of a peptide for use according to the invention may be the amidated derivative, which is indicated as "—NH$_2$". Where nothing else is stated the N-terminal amino acid of a polypeptide comprises a free amino-group, this may also be specified as "H—".

A peptide, fragment, homologue or variant thereof according to the invention can also comprise one or several unnatural amino acids.

A preferred peptide according to the invention is an isolated contiguous peptide sequence which comprises at most 13 amino acid residues of NCAM fibronectin type 3, II module. It is understood that all peptides according to the invention comprise at least one amino acid sequence selected from any of the sequences SEQ ID NOs: 1-4 or a fragment, variant or homologue thereof.

Thus, some embodiments of the invention may relate to a peptide comprising a fragment of a sequence selected from SEQ ID NOs:1-4. Another embodiment may relate to variants of SEQ ID NOs:1-4. A further embodiment may relate to homologues of SEQ ID NOs: 1-4

A variant according to the invention of an amino acid sequence selected from the sequences SEQ ID NOs: 1-4 may be i) an amino acid sequence which has at least 75% identity with a selected sequence, such as 76-80% identity, for example 81-85% identity, such as 86-90% identity, for example 91-95% identity, such as 96-99% identity, wherein the identity is defined as a percentage of identical amino acids in said sequence when it is collated with the selected sequence. The identity between amino acid sequences may be calculated using well known algorithms such as BLOSUM 30, BLOSUM 40, BLOSUM 45, BLOSUM 50, BLOSUM 55, BLOSUM 60, BLOSUM 62, BLOSUM 65, BLOSUM 70, BLOSUM 75, BLOSUM 80, BLOSUM 85, or BLOSUM 90;

ii) an amino acid sequence which has at least 75% positive amino acid matches with a selected sequence, such as 76-80% positive amino acid matches, for example 81-85% positive amino acid matches, such as 86-90% positive amino acid matches, for example 91-95% positive amino acid matches, such as 96-99% positive amino acid matches, wherein the positive amino acid match is defined as the presence at the same position in two compared sequences of amino acid residues which has similar physical and/or chemical properties. Preferred positive amino acid matches of the present invention are K to R, E to D, L to M, Q to E, I to V, I to L, A to S, Y to W, K to Q, S to T, N to S and Q to R;

iii) an amino acid sequence which is identical to a selected sequence, or it has at least 75% identity with said sequence such as 76-80% identity, for example 81-85% identity, such as 86-90% identity, for example 91-95% identity, such as 96-99% identity, or has at least 75% positive amino acid matches with the selected sequence, such as 76-80% positive amino acid matches, for example 81-85% positive amino acid matches, such as 86-90% positive amino acid matches, for example 91-95% positive amino acid matches, such as 96-99% positive amino acid matches, and comprises other chemical moieties, e. g. phosphoryl, sulphur, acetyl, glycosyl moieties.

The term "variant of a peptide sequence" also means that the peptide sequence may be modified, for example by substitution of one or more of the amino acid residues. Both L-amino acids and D-amino acids may be used. Other modification may comprise derivatives such as esters, sugars, etc., for example methyl and acetyl esters, as well as polyethylene glycol modifications.

Furthermore, an amine group of the peptide may be converted to amides, wherein the acid part of the amide is a fatty acid.

In another aspect, variants of the amino acid sequences according to the invention may comprise, within the same variant, or fragments thereof or among different variants, or fragments thereof, at least one substitution, such as a plurality of substitutions introduced independently of one another. Variants of the complex, or fragments thereof may thus comprise conservative substitutions independently of one another, wherein at least one glycine (Gly) of said variant, or fragments thereof is substituted with an amino acid selected from the group of amino acids consisting of Ala, Val, Leu, and Ile, and independently thereof, variants, or fragments thereof, wherein at least one alanine (Ala) of said variants, or fragments thereof is substituted with an amino acid selected from the group of amino acids consisting of Gly, Val, Leu, and Ile, and independently thereof, variants, or fragments thereof, wherein at least one valine (Val) of said variant, or fragments thereof is substituted with an amino acid selected from the group of amino acids consisting of Gly, Ala, Leu, and Ile, and independently thereof, variants, or fragments thereof, wherein at least one leucine (Leu) of said variant, or fragments thereof is substituted with an amino acid selected from the group of amino acids consisting of Gly, Ala, Val, and Ile, and independently thereof, variants, or fragments thereof, wherein at least one isoleucine (Ile) of said variants, or fragments thereof is substituted with an amino acid selected from the group of amino acids consisting of Gly, Ala, Val and Leu, and independently thereof, variants, or fragments thereof wherein at least one aspartic acids (Asp) of said variant, or fragments thereof is substituted with an amino acid selected from the group of amino acids consisting of Glu, Asn, and Gln, and independently thereof, variants, or fragments thereof, wherein at least one aspargine (Asn) of said variants, or fragments thereof is substituted with an amino acid selected from the group of amino acids consisting of Asp, Glu, and Gln, and independently thereof, variants, or fragments thereof, wherein at least one glutamine (Gln) of said variants, or fragments thereof is substituted with an amino acid selected from the group of amino acids consisting of Asp, Glu, and Asn, and wherein at least one phenylalanine (Phe) of said variants, or fragments thereof is substituted with an amino acid selected from the group of amino acids consisting of Tyr, Trp, His, Pro, and preferably selected from the group of amino acids consisting of Tyr and Trp, and independently thereof, variants, or fragments thereof, wherein at least one tyrosine (Tyr) of said variants, or fragments thereof is substituted with an amino acid selected from the group of amino acids consisting of Phe, Trp, His, Pro, preferably an amino acid selected from the group of amino acids consisting of Phe and Trp, and independently thereof, variants, or fragments thereof, wherein at least one arginine (Arg) of said fragment is substituted with an amino acid selected from the group of amino acids consisting of Lys and His, and independently thereof, variants, or fragments thereof, wherein at least one lysine (Lys) of said variants, or fragments thereof is substituted with an amino acid selected from the group of amino acids consisting of Arg and His, and independently thereof, variants, or fragments thereof, and independently thereof, variants, or fragments thereof, and wherein at least one proline (Pro) of said variants, or fragments thereof is substituted with an amino acid selected from the group of amino acids consisting of Phe, Tyr, Trp, and His, and independently thereof, variants, or fragments thereof, wherein at least one cysteine (Cys) of said variants, or fragments thereof is substituted with an amino acid selected from the group of amino acids consisting of Asp, Glu, Lys, Arg, His, Asn, Gln, Ser, Thr, and Tyr.

It thus follows from the above that the same variant of a peptide fragment, or fragment of said variant may comprise more than one conservative amino acid substitution from more than one group of conservative amino acids as defined herein above. The term "conservative amino acid substitution" is used synonymously herein with the term "homologous amino acid substitution".

The groups of conservative amino acids are as the following:
  A, G (neutral, weakly hydrophobic),
  Q, N, S, T (hydrophilic, non-charged)
  E, D (hydrophilic, acidic)
  H, K, R (hydrophilic, basic)
  L, P, I, V, M, F, Y, W (hydrophobic, aromatic)
  C (cross-link forming)

Conservative substitutions may be introduced in any position of a preferred predetermined peptide for use according to the invention or fragment thereof. It may however also be desirable to introduce non-conservative substitutions, particularly, but not limited to, a non-conservative substitution in any one or more positions.

A non-conservative substitution leading to the formation of a variant fragment of the peptide for use according to the invention would for example differ substantially in polarity, for example a residue with a non-polar side chain (Ala, Leu, Pro, Trp, Val, Ile, Leu, Phe or Met) substituted for a residue with a polar side chain such as Gly, Ser, Thr, Cys, Tyr, Asn, or Gln or a charged amino acid such as Asp, Glu, Arg, or Lys, or substituting a charged or a polar residue for a non-polar one; and/or ii) differ substantially in its effect on peptide backbone orientation such as substitution of or for Pro or Gly by another residue; and/or iii) differ substantially in electric charge, for example substitution of a negatively charged residue such as Glu or Asp for a positively charged residue such as Lys, His or Arg (and vice versa); and/or iv) differ substantially in steric bulk, for example substitution of a bulky residue such as His, Trp, Phe or Tyr for one having a minor side chain, e.g. Ala, Gly or Ser (and vice versa).

Substitution of amino acids may in one embodiment be made based upon their hydrophobicity and hydrophilicity values and the relative similarity of the amino acid side-chain substituents, including charge, size, and the like.

Examples of variants are:

EX1a-X2b-VAENQQGKSKA

DX1a-X2a-VAENQQGKSKA

Wherein X1a is F, A, C, G, Q, L, M, N, S, Y, T, I, P, V, more preferred X1a is A, G, L, M, V, P, I
And X2b is Q, N, S, T, G or deleted
Specific non-limiting examples of variants are:

| | |
|---|---|
| EVVAENQQGKSKA | (SEQ ID NO: 2) |
| NVVAENQQGKSKA | (SEQ ID NO: 3) |
| NSVAENQQGKSKA | (SEQ ID NO: 4) |
| AVAENQQGKSKA | (SEQ ID NO: 5) |
| GVAENQQGKSKA | (SEQ ID NO: 6) |
| LVAENQQGKSKA | (SEQ ID NO: 7) |
| MVAENQQGKSKA | (SEQ ID NO: 8) |
| VVAENQQGKSKA | (SEQ ID NO: 9) |
| PVAENQQGKSKA | (SEQ ID NO: 10) |
| IVAENQQGKSKA | (SEQ ID NO: 11) |
| QAVAENQQGKSKA | (SEQ ID NO: 12) |
| QGVAENQQGKSKA | (SEQ ID NO: 13) |
| QLVAENQQGKSKA | (SEQ ID NO: 14) |
| QMVAENQQGKSKA | (SEQ ID NO: 15) |
| QVVAENQQGKSKA | (SEQ ID NO: 16) |
| QPVAENQQGKSKA | (SEQ ID NO: 17) |
| QIVAENQQGKSKA | (SEQ ID NO: 18) |
| NAVAENQQGKSKA | (SEQ ID NO: 19) |
| NGVAENQQGKSKA | (SEQ ID NO: 20) |
| NLVAENQQGKSKA | (SEQ ID NO: 21) |
| NMVAENQQGKSKA | (SEQ ID NO: 22) |
| NVVAENQQGKSKA | (SEQ ID NO: 23) |
| NPVAENQQGKSKA | (SEQ ID NO: 24) |
| NIVAENQQGKSKA | (SEQ ID NO: 25) |
| SAVAENQQGKSKA | (SEQ ID NO: 26) |
| SGVAENQQGKSKA | (SEQ ID NO: 27) |
| SLVAENQQGKSKA | (SEQ ID NO: 28) |
| SMVAENQQGKSKA | (SEQ ID NO: 29) |
| SVVAENQQGKSKA | (SEQ ID NO: 30) |

| | |
|---|---|
| SPVAENQQGKSKA | (SEQ ID NO: 31) |
| SIVAENQQGKSKA | (SEQ ID NO: 32) |
| TAVAENQQGKSKA | (SEQ ID NO: 33) |
| TGVAENQQGKSKA | (SEQ ID NO: 34) |
| TLVAENQQGKSKA | (SEQ ID NO: 35) |
| TMVAENQQGKSKA | (SEQ ID NO: 36) |
| TVVAENQQGKSKA | (SEQ ID NO: 37) |
| TPVAENQQGKSKA | (SEQ ID NO: 38) |
| TIVAENQQGKSKA | (SEQ ID NO: 39) |
| GAVAENQQGKSKA | (SEQ ID NO: 40) |
| GGVAENQQGKSKA | (SEQ ID NO: 41) |
| GLVAENQQGKSKA | (SEQ ID NO: 42) |
| GMVAENQQGKSKA | (SEQ ID NO: 43) |
| GVVAENQQGKSKA | (SEQ ID NO: 44) |
| GPVAENQQGKSKA | (SEQ ID NO: 45) |
| GIVAENQQGKSKA | (SEQ ID NO: 46) |

In another embodiment the variant has the following formula

X3a-X3b-X3c-VAENQQGKSKA

Wherein X3a is F, A, C, G, Q, L, M, N, S, Y, T, I, P, V or deleted, or more preferred X3a is A, G, L, M, V, P, I or deleted, and X3b is D or E, and X3c is A, G, L, M, V, P, I or deleted With the proviso that X3a and X3c cannot both be deleted Examples of specific variants are:

| | |
|---|---|
| DAVAENQQGKSKA | (SEQ ID NO: 47) |
| DGVAENQQGKSKA | (SEQ ID NO: 48) |
| DLVAENQQGKSKA | (SEQ ID NO: 49) |
| DMVAENQQGKSKA | (SEQ ID NO: 50) |
| DVVAENQQGKSKA | (SEQ ID NO: 51) |
| DPVAENQQGKSKA | (SEQ ID NO: 52) |
| DIVAENQQGKSKA | (SEQ ID NO: 53) |
| EAVAENQQGKSKA | (SEQ ID NO: 54) |
| EGVAENQQGKSKA | (SEQ ID NO: 55) |
| ELVAENQQGKSKA | (SEQ ID NO: 56) |
| EMVAENQQGKSKA | (SEQ ID NO: 57) |
| EVVAENQQGKSKA | (SEQ ID NO: 2) |
| EPVAENQQGKSKA | (SEQ ID NO: 58) |
| EIVAENQQGKSKA | (SEQ ID NO: 59) |
| ADVAENQQGKSKA | (SEQ ID NO: 60) |
| GDVAENQQGKSKA | (SEQ ID NO: 61) |
| LDVAENQQGKSKA | (SEQ ID NO: 62) |
| MDVAENQQGKSKA | (SEQ ID NO: 63) |
| VDVAENQQGKSKA | (SEQ ID NO: 64) |
| PDVAENQQGKSKA | (SEQ ID NO: 65) |
| IDVAENQQGKSKA | (SEQ ID NO: 66) |
| AEVAENQQGKSKA | (SEQ ID NO: 67) |
| GEVAENQQGKSKA | (SEQ ID NO: 68) |
| LEVAENQQGKSKA | (SEQ ID NO: 69) |
| MEVAENQQGKSKA | (SEQ ID NO: 70) |
| VEVAENQQGKSKA | (SEQ ID NO: 71) |
| PEVAENQQGKSKA | (SEQ ID NO: 72) |
| IEVAENQQGKSKA | (SEQ ID NO: 73) |

In yet another embodiment the variant has the formula

X2a-X2b-VAENQQGKSKA

Wherein X2a is F, A, C, G, Q, L, M, N, S, Y, T, I, P, V, or more preferred X2a is A, G, L, M, V, P, I And X2b is D, E Both fragments and variants of amino acid sequences according to the invention are the functional equivalents of said sequences.

By the term "functional equivalent" of an amino acid sequence is in the present context meant a molecule which meets the criteria for a variant or a fragment of said amino acid sequence described above and which is capable of one or more functional activities of said sequence or a compound comprising said sequence. In a preferred embodiment the functional equivalent of an amino acid sequence according to the invention is capable of binding and modulating activity of FGFRs.

The invention relates both to isolated peptides according to the invention and fusion proteins comprising peptides according to the invention.

In one embodiment, the peptide according to the invention is an isolated peptide. By the term "isolated peptide" is meant that the peptide according to the invention is an individual compound and not a part of another compound. The isolated peptide may be produced by use of any recombinant technology methods or chemical synthesis and separated from other compounds, or it may be separated from a longer polypeptide or protein by a method of enzymatic or chemical cleavage and further separated from other protein fragments.

An isolated peptide according to the invention may in another embodiment comprise a fragment of NCAM which comprises a contiguous amino acid sequence derived from NCAM, selected from SEQ ID NOs:1-4 or variant thereof. In another embodiment the isolated peptide may consist of one or more of the sequences SEQ ID NOs:1-4.

Lipophilic Group

In one embodiment the compound according to the invention is provided with at least one lipophilic group, such as a fatty acid.

The lipophilic group may be attached to the peptide as such or to a linker or a spacer connected to the peptide(s).

In one embodiment of the invention an amino group of a spacer forms an amide bond with a carboxyl group of the lipophilic substituent.

In one embodiment of the invention the lipophilic substituent comprises a partially or completely hydrogenated cyclopentanophenathrene skeleton.

In one embodiment of the invention the lipophilic substituent is an straight-chain or branched alkyl group. In one embodiment of the invention the lipophilic substituent is the acyl group of a straight-chain or branched fatty acid.

In a further preferred embodiment the lipophillic substituent is a acyl group of the formula *C(C=O)—(CH)$_{6-40}$—CH$_3$. The * specifies the point of attachment In a further preferred embodiment the lipophillic substituent is a acyl group of the formula *C(C=O)—(CH)$_{8-26}$—CH$_3$. The * specifies the point of attachment In a further preferred embodiment the lipophillic substituent is a acyl group of the formula *C(C=O)—(CH)$_{8-20}$—CH$_3$. The * specifies the point of attachment.

In a further preferred embodiment the lipophillic substituent is a acyl group of the formula *C(C=O)—(CH)$_m$CH$_3$. The * specifies the point of attachment, and m is 8, 9, 10, 11, 12, 13, 14, 15, 16, 17, 18.

In a further preferred embodiment the lipophillic substituent comprises of a straight or branched dicarboxylic acids In a further preferred embodiment the lipophillic substituent comprises of a straight or branched dicarboxylic acids of the formula *C(C=O)—(CH)$_{6-40}$—C(O)OH. The * specifies the point of attachment In a further preferred embodiment the lipophillic substituent comprises of a straight or branched dicarboxylic acids of the formula *C(C=O)—(CH)$_{8-26}$—C(O)OH. The * specifies the point of attachment In a further preferred embodiment the lipophillic substituent comprises of a straight or branched dicarboxylic acids of the formula *C(C=O)—(CH)$_{8-20}$—C(O)OH. The * specifies the point of attachment In a further preferred embodiment the lipophillic substituent comprises of a straight or branched dicarboxylic acids of the formula *C(C=O)—(CH)$_{8-18}$—C(O)OH. The * specifies the point of attachment In a further preferred embodiment the lipophillic substituent comprises of a straight or branched dicarboxylic acids of the formula *C(C=O)—(CH)$_n$—C(O)OH. The * specifies the point of attachment n is 8, 9, 10, 11, 12, 13, 14, 15, 16, 17, 18.

Production of Peptide Sequences

The peptide sequences of the present invention may be prepared by any conventional synthetic methods, recombinant DNA technologies, enzymatic cleavage of full-length proteins which the peptide sequences are derived from, or a combination of said methods.

Recombinant Preparation

Thus, in one embodiment the peptides of the invention are produced by use of recombinant DNA technologies.

The DNA sequence encoding a peptide or the corresponding full-length protein the peptide originates from may be prepared synthetically by established standard methods, e.g. the phosphoamidine method described by Beaucage and Caruthers, 1981, Tetrahedron Lett. 22:1859-1869, or the method described by Matthes et al., 1984, EMBO J. 3:801-805. According to the phosphoamidine method, oligonucleotides are synthesised, e.g. in an automatic DNA synthesiser, purified, annealed, ligated and cloned in suitable vectors.

The DNA sequence encoding a peptide may also be prepared by fragmentation of the DNA sequences encoding the corresponding full-length protein of peptide origin, using DNAase I according to a standard protocol (Sambrook et al., Molecular cloning: A Laboratory manual. 2 rd ed., CSHL Press, Cold Spring Harbor, N.Y., 1989). The present invention relates to full-length proteins selected from the groups of proteins identified above. The DNA encoding the full-length proteins of the invention may alternatively be fragmented using specific restriction endonucleases. The fragments of DNA are further purified using standard procedures described in Sambrook et al., Molecular cloning: A Laboratory manual. 2 rd ed., CSHL Press, Cold Spring Harbor, N.Y., 1989.

The DNA sequence encoding a full-length protein may also be of genomic or cDNA origin, for instance obtained by preparing a genomic or cDNA library and screening for DNA sequences coding for all or part of the full-length protein by hybridisation using synthetic oligonucleotide probes in accordance with standard techniques (cf. Sambrook et al., Molecular Cloning: A Laboratory Manual, 2nd Ed., Cold Spring Harbor, 1989). The DNA sequence may also be prepared by polymerase chain reaction using specific primers, for instance as described in U.S. Pat. No. 4,683,202 or Saiki et al., 1988, Science 239:487-491.

The DNA sequence is then inserted into a recombinant expression vector, which may be any vector, which may conveniently be subjected to recombinant DNA procedures. The choice of vector will often depend on the host cell into which it is to be introduced. Thus, the vector may be an autonomously replicating vector, i.e. a vector that exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

In the vector, the DNA sequence encoding a peptide or a full-length protein should be operably connected to a suitable promoter sequence. The promoter may be any DNA sequence, which shows transcriptional activity in the host cell of choice and may be derived from genes encoding proteins either homologous or heterologous to the host cell. Examples of suitable promoters for directing the transcription of the coding DNA sequence in mammalian cells are the SV 40 promoter (Subramani et al., 1981, Mol. Cell Biol. 1:854-864), the MT-1 (metallothionein gene) promoter (Palmiter et al., 1983, Science 222: 809-814) or the adenovirus 2 major late promoter. A suitable promoter for use in insect cells is the polyhedrin promoter (Vasuvedan et al., 1992, FEBS Lett. 311:7-11). Suitable promoters for use in yeast host cells include promoters from yeast glycolytic genes (Hitzeman et al., 1980, J. Biol. Chem. 255:12073-12080; Alber and Kawasaki, 1982, J. Mol. Appl. Gen. 1: 419-434) or alcohol dehydrogenase genes (Young et al., 1982, in Genetic Engineering of Microorganisms for Chemicals, Hollaender et al, eds., Plenum Press, New York), or the TPI1 (U.S. Pat. No. 4,599,311) or ADH2-4c (Russell et al., 1983, Nature 304: 652-654) promoters. Suitable promoters for use in filamentous fungus host cells are, for instance, the ADH3 promoter (McKnight et al., 1985, EMBO J. 4:2093-2099) or the tpiA promoter.

The coding DNA sequence may also be operably connected to a suitable terminator, such as the human growth hormone terminator (Palmiter et al., op. cit.) or (for fungal hosts) the TPI1 (Alber and Kawasaki, op. cit.) or ADH3 (McKnight et al., op. cit.) promoters. The vector may further comprise elements such as polyadenylation signals (e.g. from SV 40 or the adenovirus 5 Elb region), transcriptional enhancer sequences (e.g. the SV 40 enhancer) and translational enhancer sequences (e.g. the ones encoding adenovirus VA RNAs).

The recombinant expression vector may further comprise a DNA sequence enabling the vector to replicate in the host cell in question. An example of such a sequence (when the host cell is a mammalian cell) is the SV 40 origin of replication. The vector may also comprise a selectable marker, e.g. a gene the product of which complements a defect in the host cell, such as the gene coding for dihydrofolate reductase (DHFR) or one which confers resistance to a drug, e.g. neomycin, hydromycin or methotrexate.

The procedures used to ligate the DNA sequences coding the peptides or full-length proteins, the promoter and the terminator, respectively, and to insert them into suitable vectors containing the information necessary for replication, are well known to persons skilled in the art (cf., for instance, Sambrook et al., op. cit.).

To obtain recombinant peptides of the invention the coding DNA sequences may be usefully fused with a second peptide coding sequence and a protease cleavage site coding sequence, giving a DNA construct encoding the fusion protein, wherein the protease cleavage site coding sequence positioned between the HBP fragment and second peptide coding DNA, inserted into a recombinant expression vector, and expressed in recombinant host cells. In one embodiment, said second peptide selected from, but not limited by the group comprising glutathion-S-reductase, calf thymosin, bacterial thioredoxin or human ubiquitin natural or synthetic variants, or peptides thereof. In another embodiment, a peptide sequence comprising a protease cleavage site may be the Factor Xa, with the amino acid sequence IEGR, enterokinase, with the amino acid sequence DDDDK, thrombin, with the amino acid sequence LVPR/GS, or *Acharombacter lyticus*, with the amino acid sequence XKX, cleavage site.

The host cell into which the expression vector is introduced may be any cell which is capable of expression of the peptides or full-length proteins, and is preferably a eukaryotic cell, such as invertebrate (insect) cells or vertebrate cells, e.g. *Xenopus laevis* oocytes or mammalian cells, in particular insect and mammalian cells. Examples of suitable mammalian cell lines are the HEK293 (ATCC CRL-1573), COS (ATCC CRL-1650), BHK (ATCC CRL-1632, ATCC CCL-10) or CHO (ATCC CCL-61) cell lines. Methods of transfecting mammalian cells and expressing DNA sequences introduced in the cells are described in e.g. Kaufman and Sharp, J. Mol. Biol. 159, 1982, pp. 601-621; Southern and Berg, 1982, J. Mol. Appl. Genet. 1:327-341; Loyter et al., 1982, Proc. Natl. Acad. Sci. USA 79: 422-426; Wigler et al., 1978, Cell 14:725; Corsaro and Pearson, 1981, in Somatic Cell Genetics 7, p. 603; Graham and van der Eb, 1973, Virol. 52:456; and Neumann et al., 1982, EMBO J. 1:841-845.

Alternatively, fungal cells (including yeast cells) may be used as host cells. Examples of suitable yeast cells include cells of *Saccharomyces* spp. or *Schizosaccharomyces* spp., in particular strains of *Saccharomyces cerevisiae*. Examples of other fungal cells are cells of filamentous fungi, e.g. *Aspergillus* spp. or *Neurospora* spp., in particular strains of *Aspergillus oryzae* or *Aspergillus niger*. The use of *Aspergillus* spp. for the expression of proteins is described in, e.g., EP 238 023.

The medium used to culture the cells may be any conventional medium suitable for growing mammalian cells, such as a serum-containing or serum-free medium containing appropriate supplements, or a suitable medium for growing insect, yeast or fungal cells. Suitable media are available from commercial suppliers or may be prepared according to published recipes (e.g. in catalogues of the American Type Culture Collection).

The peptides or full-length proteins recombinantly produced by the cells may then be recovered from the culture medium by conventional procedures including separating the host cells from the medium by centrifugation or filtration, precipitating the proteinaceous components of the supernatant or filtrate by means of a salt, e.g. ammonium sulphate, purification by a variety of chromatographic procedures, e.g. HPLC, ion exchange chromatography, affinity chromatography, or the like.

Synthetic Preparation

The methods for synthetic production of peptides are well known in the art. Detailed descriptions as well as practical advice for producing synthetic peptides may be found in Synthetic Peptides: A User's Guide (Advances in Molecular Biology), Grant G. A. ed., Oxford University Press, 2002, or in: Pharmaceutical Formulation: Development of Peptides and Proteins, Frokjaer and Hovgaard eds., Taylor and Francis, 1999.

Peptides may for example be synthesised by using Fmoc chemistry and with Acm-protected cysteins. After purification by reversed phase HPLC, peptides may be further processed to obtain for example cyclic or C- or N-terminal modified isoforms. The methods for cyclization and terminal modification are well-known in the art and described in detail in the above-cited manuals.

In a preferred embodiment the peptide sequences of the invention are produced synthetically, in particular, by the Sequence Assisted Peptide Synthesis (SAPS) method.

Peptides may be synthesised either batchwise in a polyethylene vessel equipped with a polypropylene filter for filtration or in the continuous-flow version of the polyamide solid-phase method (Dryland, A. and Sheppard, R. C., (1986) J. Chem. Soc. Perkin Trans. I, 125-137.) on a fully automated peptide synthesiser using 9-fluorenylmethyloxycarbonyl (Fmoc) or tert.-Butyloxycarbonyl, (Boc) as N-a-amino protecting group and suitable common protection groups for side-chain functionality's.

Multimeric Compound

An isolated peptide sequence of the invention may be connected to another isolated peptide sequence by a chemical bond in a fusion protein or the amino acid sequences may be connected to each other through a linker group. In some embodiments a peptide sequence of the invention may be formulated as an oligomer (multimer) of monomers, wherein each monomer is as a peptide sequence defined above. Particularly, multimeric peptides such as dendrimers may form conformational determinants or clusters due to the presence of multiple flexible peptide monomers. In one embodiment the compound is a dimmer, in another embodiment the compound is a trimer or a tetramer. In one embodiment the compound is a dendrimer, such as four peptides linked to a lysine backbone, or coupled to a polymer carrier, for example a protein carrier, such as BSA. Polymerisation such as repetitive sequences or attachment to various carriers are well-known in the art, e.g. lysine backbones, such as lysine dendrimers carrying 4 peptides, 8 peptides, 16 peptides, or 32 peptides. Other carriers may be lipophilic dendrimers, or micelle-like carriers formed by lipophilic derivatives, or starburst (star-like) carbon chain polymer conjugates.

Thus, according to the invention a multimeric compound may be a polymer comprising two or more identical or different peptide sequences of the invention, wherein in a preferred embodiment, at least one of the two or more amino acid sequences is selected from a sequence of a peptide according to this invention.

In some embodiments, the compound may comprise two identical amino acid sequences or the compound may comprise four identical copies of an amino acid sequence.

In other embodiments, the compound may comprise two or more different amino acid sequences, wherein at least one of the two amino acid sequences is a sequence selected from the peptide sequences shown herein, or fragments or variants thereof. More preferably two or more sequences are selected from the sequences shown herein.

A multimeric compound of the invention is a compound comprising the formula $(Z_n\text{-}L_m)_q$, wherein
- Z is an individually selected peptide comprising the sequence QQGKSKA;
- L is individually selected from the group consisting of lipophilic substituents, linkers, optionally substituted, and spacers, optionally substituted;
- n is an individually selected integer from 1 to 6;
- m is an individually selected integer from 0 to 6;
- q is an individually selected integer from 1 to 4,
- with the proviso that when m is 0 and q is 1, then z is at most 13 contiguous amino acid residues,
- or a pharmaceutically acceptable salt thereof.

Examples of compounds of the invention are:

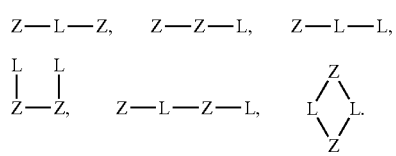

A preferred multimeric compound of the invention is a compound wherein the amino acid sequences are connected to each other through a linker or a linker group, such as

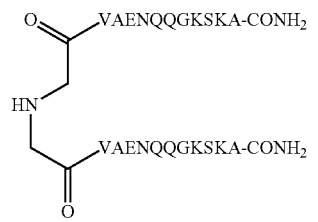

FGLs

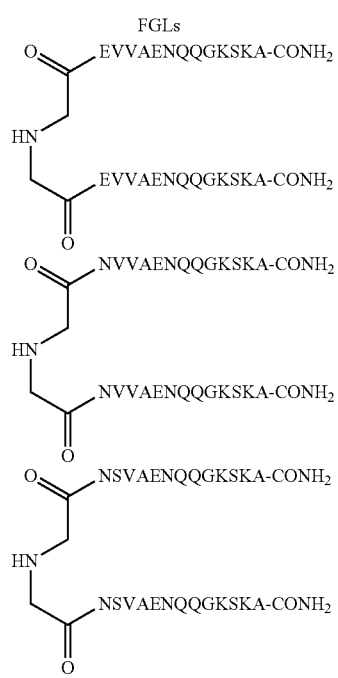

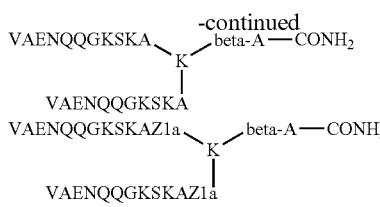

wherein
Z1a is one of two aminoacid selected from the group F, A, G, Q, L, M, N, S, Y, T, I, P, V
More preferred:
Z1a is one or two aminoacids selected from the group A, G, Q, L, N, S, T, I, P, V
Even more preferred:
Z1a is one or two aminoacids selected from A, G, S, N
Z1a is one aminoacid selected from the group F, A, G, Q, L, M, N, S, Y, T, I, P, V
More preferred:
Z1a is one aminoacids selected from the group A, G, Q, L, N, S, T, I, P, V
Even more preferred:
Z1a is one aminoacids selected from A, G, S, N In one embodiment two individual peptide sequences of a compound are co-joined by a linker. A linker molecule may according to the invention be selected from achiral di-, tri- or tetracarboxylic acids, said acids having the general formula

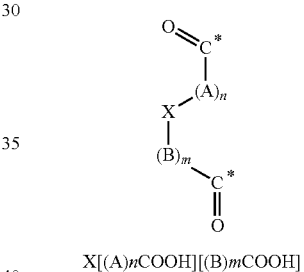

$X[(A)n\text{COOH}][(B)m\text{COOH}]$

The compound may be produced by the LPA method as described in WO 00/18791.

In one embodiment
n and m independently are an integer of from 1 to 20,
X is HN, $H_2N(CR_2)pCR$, $RHN(CR_2)pCR$, $HO(CR_2)pCR$, $HS(CR_2)pCR$, halogen-$(CR_2)pCR$, $HOOC(CR_2)pCR$, $ROOC(CR_2)pCR$, $HCO(CR_2)pCR$, $RCO(CR_2)pCR$, [HOOC(A)n][HOOC(B)m]$CR(CR_2)pCR$, $H_2N(CR_2)p$, $RHN(CR_2)p$, $HO(CR_2)p$, $HS(CR_2)p$, halogen-$(CR_2)p$, $HOOC(CR_2)p$, $ROOC(CR_2)p$, $HCO(CR_2)p$, $RCO(CR_2)p$, or [HOOC(A)n][HOOC(B)m]$(CR_2)p$, wherein p is 0 or integer of from 1 to 20, A and B independently are a substituted or unsubstituted $C_{1-10}$ alkyl, a substituted or unsubstituted $C_{2-10}$ alkenyl, a substituted or unsubstituted cyclic moiety, a substituted or unsubstituted heterocyclic moiety, a substituted or unsubstituted aromatic moiety, or A and B together form a substituted or unsubstituted cyclic moiety, substituted or unsubstituted heterocyclic moiety, substituted or unsubstituted aromatic moiety.

Under the term $C_{1-10}$ alkyl is meant straight or branched chain alkyl groups having 1-10 carbon atoms, e.g. methyl, ethyl, isopropyl, butyl, and tertbutyl.

Under the term $C_{2-10}$ alkenyl is meant straight or branched chain alkenyl groups having 2-10 carbon atoms, e.g. ethynyl, propenyl, isopropenyl, butenyl, and tert-butenyl.

Under the term cyclic moiety is meant cyclohexan, and cyclopentane.

Under the term aromatic moiety is meant phenyl.

The wording "A and B forms a cyclic, heterocyclic or aromatic moiety" denotes cyclohexan, piperidine, benzene, and pyridine.

In one embodiment the suitable achiral di-, tri- or tetracarboxylic acids to be used in the present invention have the general formula

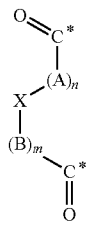

X[(A)nCOOH][(B)mCOOH]

wherein n and m independently are an integer of from 1 to 20, X is HN, A and B independently are a substituted or unsubstituted $C_{1-10}$ alkyl, a substituted or unsubstituted $C_{2-10}$ alkenyl, a substituted or unsubstituted cyclic moiety, a substituted or unsubstituted heterocyclic moiety, a substituted or unsubstituted aromatic moiety, or A and B together form a substituted or unsubstituted cyclic moiety, substituted or unsubstituted heterocyclic moiety, substituted or unsubstituted aromatic moiety.

In another embodiment suitable achiral di-, tri- or tetracarboxylic acids to be used in the present method have the general formula

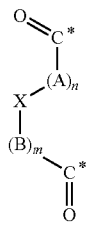

X[(A)nCOOH][(B)mCOOH]

wherein n and m are 0 or an integer of from 1 to 20, X is $H_2N(CR_2)pCR$, or $RHN(CR_2)pCR$, wherein p is 0 or integer of from 1 to 20, wherein each R is H, a substituted or unsubstituted $C_{1-10}$ alkyl, a substituted or unsubstituted $C_{2-10}$ alkenyl, a substituted or unsubstituted cyclic moiety, a substituted or unsubstituted heterocyclic moiety, a substituted or unsubstituted aromatic moiety, or A and B together form a substituted or unsubstituted cyclic moiety, substituted or unsubstituted heterocyclic moiety, substituted or unsubstituted aromatic moiety.

In still another embodiment suitable achiral di-, tri- or tetracarboxylic acids to be used in the present method have the general formula

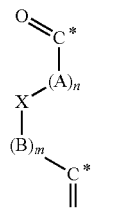

X[(A)nCOOH][(B)mCOOH]

wherein n and m are 0 or an integer of from 1 to 20, X is $HO(CR_2)pCR$, $HS(CR_2)pCR$, halogen-$(CR_2)pCR$, $HOOC(CR_2)pCR$, $ROOC(CR_2)pCR$, $HCO(CR_2)pCR$, $RCO(CR_2)pCR$, or $[HOOC(A)n][HOOC(B)m]CR(CR_2)pCR$, wherein p is 0 or integer of from 1 to 20, each R independently is H or a substituted or unsubstituted $C_{1-10}$ alkyl, a substituted or unsubstituted $C_{2-10}$ alkenyl, a substituted or unsubstituted cyclic moiety, a substituted or unsubstituted heterocyclic moiety, a substituted or unsubstituted aromatic moiety, or A and B together form a substituted or unsubstituted cyclic moiety, substituted or unsubstituted heterocyclic moiety, substituted or unsubstituted aromatic moiety.

In yet another embodiment suitable achiral di-, tri- or tetracarboxylic acids to be used in the present method have the general formula

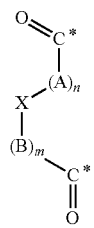

X[(A)nCOOH][(B)mCOOH]

Wherein n and m are 0 or an integer of from 1 to 20, X is $H_2N(CR_2)p$, $RHN(CR_2)p$, $HO(CR_2)p$, $HS(CR_2)p$, halogen-$(CR_2)p$, $HOOC(CR_2)p$, $ROOC(CR_2)p$, $HCO(CR_2)p$, $RCO(CR_2)p$, or $[HOOC(A)n][HOOC(B)m](CR_2)p$, wherein p is 0 or integer of from 1 to 20, each R independently is H or a substituted or unsubstituted $C_{1-10}$ alkyl, a substituted or unsubstituted $C_{2-10}$ alkenyl, a substituted or unsubstituted cyclic moiety, a substituted or unsubstituted heterocyclic moiety, a substituted or unsubstituted aromatic moiety, or A and B together form a substituted or unsubstituted cyclic moiety, substituted or unsubstituted heterocyclic moiety, substituted or unsubstituted aromatic moiety.

Favourable di-, tri- and tetracarboxylic acids for providing the ring structure may be selected from imino diacetic acid, 2-amino malonic acid, 3-amino glutaric acid, 3-methylamino glutaric acid, 3-chloro glutamic acid, 3-methoxy-carbonyl glutaric acid, 3-acetyl glutaruc acid, glutaric acid, tricarballylic acid, 3,4-bis-carboxymethyl adipic acid, 4-(2-carboxyethyl)-pimelic acid, (3,5-bis-carboxymethyl-phenyl)-acetic acid, 3,4-bis-carboxymethyl-adipic acid, benzene-1,2,4,5-tetra carboxylic acid, 4-(3-carboxy-allylamino)-but-2-enoic acid, 4,4-imino-dibenzoic acid, 1,4-dihydropyridine-3,5-dicarboxylic acid, 5-amino isophthalic acid, 2-chloro malonic acid, 3-hydroxy glutaric acid, and benzene-1,3,5-tricarboxylic acid.

Fragment coupling (fragment coupling or fragment condensation) may be performed according to standard procedures, e.g. as described in Peptide Synthesis protocols, Methods in Molecular Biology Vol. 35, Chapter 15, 303-316, Nyfeler R, Pennington M W and Dunne B M Eds., Humana Press, 1994. Accordingly, fragments may be synthesised on a solid phase, cleaved from the solid phase with full preservation of protecting groups, purified and characterised as described above. Suitable fragments may also be obtained by other techniques described above.

According to the invention two individual peptide sequences comprising two or more of the defined above amino acid sequences are connected to each other so that one of these two peptide sequences is covalently bound to one of two carboxylic group of a linker molecule selected from the molecules defined above and another of the peptide sequences is covalently bound to another carboxylic group of said linker molecule. The peptide sequences are covalently bound to the linker through their amino- or carboxy-groups of the N- or C terminal amino acid residue, respectively. Accordingly, a compound of the invention has the formula COOH/CONH2-peptide sequence-NH—CO-linker-CO—NH-peptide sequence-COOH/CONH2 or NH2-peptide sequence-CO—NH-linker-NH—CO-peptide sequence-NH2.

In one embodiment the compound according to the invention is exemplified by the following formula:

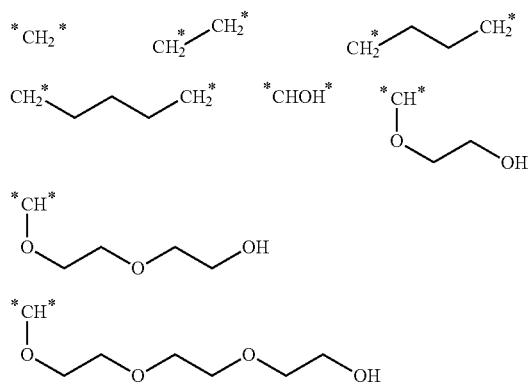

Wherein T1a is selected from the group consisting of, wherein * is the point of attachment

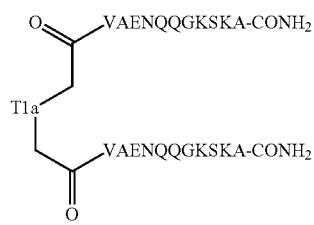

In another preferred multimeric compound of the invention, two individual peptide sequences are connected to each other through two individual linkers or linker groups, such as

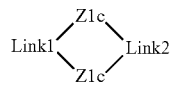

Link2 may have the following structure where * denotes the point of attachment to the C-terminal of the amino acid sequences Z1c or Link 2 is absent and the C-terminal group is an acidic acid or amide (unsubstituted amide shown in structure):

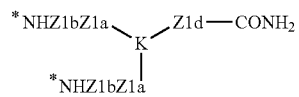

Where Z1a is one or two amino acids independently selected from the group consisting of F, A, G, Q, L, M, N, S, Y, T, I, P, V or absent.

Z1b is one amino acid selected from the group consisting of F, A, G, Q, L, M, N, S, Y, T, I, P, V or absent.

Z1d is a beta amino acid as e.g. beta-alanine.

Each Z1c is independently selected from one of the peptide sequences shown herein.

The C-terminal amide might be mono or disubstituted with a branched or unbranched C1-20 alkyle group. The alkyle group might be substituted with one or more functional groups as e.g. a hydroxyl group, carboxylic acid group, an amide group or a halogen group.

Link 1 can in one embodiment be a suitable achiral di-, tri- or tetracarboxylic acids having the general formula:

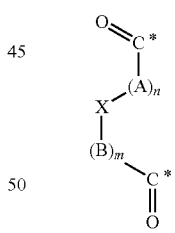

where * denotes the point of attachment to the N-terminal part of the amino acid sequence Z1c or Link1 is absent and the N-terminal amino group is a $NH_2$ group, wherein n and m independently are an integer of from 1 to 20, X is HN, A and B independently are a substituted or unsubstituted $C_{1-10}$ alkyl, a substituted or unsubstituted $C_{2-10}$ alkenyl, a substituted or unsubstituted cyclic moiety, a substituted or unsubstituted heterocyclic moiety, a substituted or unsubstituted aromatic moiety, or A and B together form a substituted or unsubstituted cyclic moiety, substituted or unsubstituted heterocyclic moiety, substituted or unsubstituted aromatic moiety.

In another embodiment link1 is a suitable achiral di-, tri- or tetracarboxylic having the general formula:

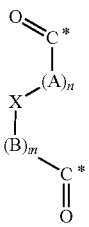

where * denotes the point of attachment of the N-terminal part of the amino acid sequence Z1c, wherein n and m independently are an integer of from 1 to 20, X is Y1b-Y1a-N, A and B independently are a substituted or unsubstituted $C_{1-10}$ alkyl, a substituted or unsubstituted $C_{2-10}$ alkenyl, a substituted or unsubstituted cyclic moiety, a substituted or unsubstituted heterocyclic moiety, a substituted or unsubstituted aromatic moiety, or A and B together form a substituted or unsubstituted cyclic moiety, substituted or unsubstituted heterocyclic moiety, substituted or unsubstituted aromatic moiety.

Wherein Y1a is a spacer

Wherein Y1b is a lipophilic substituent comprising of an acyl group of a straight chain or branched fatty acid or a strait or branched dicarboxylic acid.

In one embodiment of the invention the spacer is a dicarboxylic acid group having from 1 to 7 methylene groups, such as two methylene groups which spacer forms a bridge between the amino group that Y1a is attached to and an amino group of the lipophilic substituent.

In one embodiment of the invention the spacer is selected from the list consisting of .beta.-alanine, gamma-aminobutyric acid (GABA), .gamma.-glutamic acid, Lys, Asp, Glu, a dipeptide containing Asp, a dipeptide containing Glu, or a dipeptide containing Lys. In one embodiment of the invention the spacer is .beta.-alanine. In one embodiment of the invention the spacer is gamma-aminobutyric acid (GABA). In one embodiment of the invention the spacer is .quadrature.-glutamic acid.

In one embodiment of the invention the amino group that Y1a is attached to forms an amide bond with a carboxylic group of a spacer, and an amino group of the spacer forms an amide bond with a carboxyl group of the lipophilic substituent.

In one embodiment of the invention the lipophilic substituent comprises a partially or completely hydrogenated cyclopentanophenathrene skeleton.

In one embodiment of the invention the lipophilic substituent is a straight-chain or branched alkyl group. In one embodiment of the invention the lipophilic substituent is the acyl group of a straight-chain or branched fatty acid.

In a further preferred embodiment the lipophillic substituent is a acyl group of the formula $*C(C=O)—(CH)_{6-40}—CH_3$. The * specifies the point of attachment In a further preferred embodiment the lipophillic substituent is a acyl group of the formula $*C(C=O)—(CH)_{8-26}—CH_3$. The * specifies the point of attachment In a further preferred embodiment the lipophillic substituent is a acyl group of the formula $*C(C=O)—(CH)_{8-20}—CH_3$. The * specifies the point of attachment.

In a further preferred embodiment the lipophillic substituent is a acyl group of the formula $*C(C=O)—(CH)_m CH_3$. The * specifies the point of attachment.

m is 8, 9, 10, 11, 12, 13, 14, 15, 16, 17, 18.

In a further preferred embodiment the lipophillic substituent comprises of a straight or branched dicarboxylic acids of the formula $*C(C=O)—(CH)_{6-40}—C(O)OH$. The * specifies the point of attachment In a further preferred embodiment the lipophillic substituent comprises of a straight or branched dicarboxylic acids of the formula $*C(C=O)—(CH)_{8-26}—C(O)OH$. The * specifies the point of attachment In a further preferred embodiment the lipophillic substituent comprises of a straight or branched dicarboxylic acids of the formula $*C(C=O)—(CH)_{8-20}—C(O)OH$. The * specifies the point of attachment In a further preferred embodiment the lipophillic substituent comprises of a straight or branched dicarboxylic acids of the formula $*C(C=O)—(CH)_{8-18}—C(O)OH$. The * specifies the point of attachment In a further preferred embodiment the lipophillic substituent comprises of a straight or branched dicarboxylic acids of the formula $*C(C=O)—(CH)_n—C(O)OH$. The * specifies the point of attachment n is 8, 9, 10, 11, 12, 13, 14, 15, 16, 17, 18.

In another embodiment link1 is a suitable achiral di-, tri- or tetracarboxylic acid having the general formula

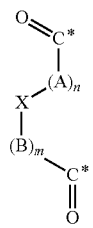

where * denotes the point of attachment of the N-terminal part of the amino acid sequence Z1c, wherein n and m are 0 or an integer of from 1 to 20, X is $H_2N(CR_2)pCR$, or $RHN(CR_2)pCR$, wherein p is 0 or integer of from 1 to 20, wherein each R is H, a substituted or unsubstituted $C_{1-10}$ alkyl, a substituted or unsubstituted $C_{2-10}$ alkenyl, a substituted or unsubstituted cyclic moiety, a substituted or unsubstituted heterocyclic moiety, a substituted or unsubstituted aromatic moiety, or A and B together form a substituted or unsubstituted cyclic moiety, substituted or unsubstituted heterocyclic moiety, substituted or unsubstituted aromatic moiety.

In another embodiment link1 is a suitable achiral di-, tri- or tetracarboxylic acid having the general structure

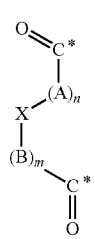

where * denotes the point of attachment of the N-terminal part of the amino acid sequence Z1c, wherein n and m are 0 or an integer of from 1 to 20, X is $HO(CR_2)pCR$, $HS(CR_2)pCR$, halogen-$(CR_2)pCR$, $HOOC(CR_2)pCR$, $ROOC(CR_2)pCR$, $HCO(CR_2)pCR$, $RCO(CR_2)pCR$, or $[HOOC(A)n][HOOC(B)m]CR(CR_2)pCR$, wherein p is 0 or integer of from 1 to 20, each R independently is H or a substituted or unsubstituted $C_{1-10}$ alkyl, a substituted or unsubstituted $C_{2-10}$ alkenyl, a substituted or unsubstituted cyclic moiety, a substituted or unsubstituted heterocyclic moiety, a substituted or unsubstituted aromatic moiety, or A and B together form a substituted or unsubstituted cyclic moiety, substituted or unsubstituted heterocyclic moiety, substituted or unsubstituted aromatic moiety.

In another embodiment link1 is a suitable achiral di-, tri- or tetracarboxylic acid having the general structure

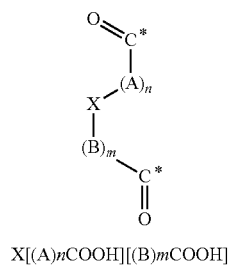

X[(A)nCOOH][(B)mCOOH]

where * denotes the point of attachment of the N-terminal part of the amino acid sequence Z1c, wherein n and m are 0 or an integer of from 1 to 20, X is $H_2N(CR_2)p$, $RHN(CR_2)p$, $HO(CR_2)p$, $HS(CR_2)p$, halogen-$(CR_2)p$, $HOOC(CR_2)p$, $ROOC(CR_2)p$, $HCO(CR_2)p$, $RCO(CR_2)p$, or [HOOC(A)n][HOOC(B)m]$(CR_2)p$, wherein p is 0 or integer of from 1 to 20, each R independently is H or a substituted or unsubstituted $C_{1-10}$ alkyl, a substituted or unsubstituted $C_{2-10}$ alkenyl, a substituted or unsubstituted cyclic moiety, a substituted or unsubstituted heterocyclic moiety, a substituted or unsubstituted aromatic moiety, or A and B together form a substituted or unsubstituted cyclic moiety, substituted or unsubstituted heterocyclic moiety, substituted or unsubstituted aromatic moiety.

In another embodiment link1 is a suitable achiral di-, tri- or tetracarboxylic acid having the general structure

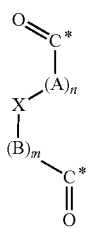

where * denotes the point of attachment of the N-terminal part of the amino acid sequence Z1c, wherein X is one of the following groups where * denotes is the point of attachment

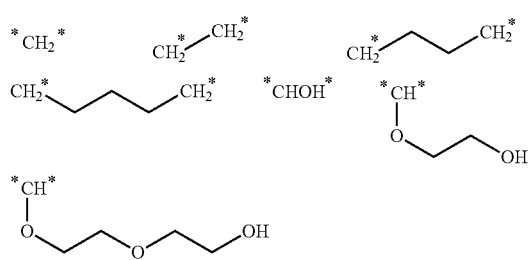

-continued

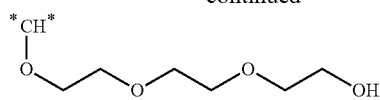

Under the term $C_{1-10}$ alkyl is meant straight or branched chain alkyl groups having 1-10 carbon atoms, e.g. methyl, ethyl, isopropyl, butyl, and tertbutyl.

Under the term $C_{2-10}$ alkenyl is meant straight or branched chain alkenyl groups having 2-10 carbon atoms, e.g. ethynyl, propenyl, isopropenyl, butenyl, and tert-butenyl.

Under the term cyclic moiety is meant cyclohexan, and cyclopentane.

Under the term aromatic moiety is meant phenyl.

The wording "A and B forms a cyclic, heterocyclic or aromatic moiety" denotes cyclohexan, piperidine, benzene, and pyridine.

By reaction with a carboxylic acid, a construct of the type X(CO-sequence)2-solid phase, wherein X as defined above, is obtained.

By the term "sequence" is in the present content meant a peptide comprising naturally occurring and/or non-naturally occurring amino acids, a PNA-sequence, or peptidomimetic. By "naturally occurring amino acids" is meant L- and D-forms of the 20 acids found in nature. Non-naturally occurring amino acids are e.g. modified naturally occurring amino acids. The term sequence is further intended to comprise one or more of such sequences. Examples of suitable peptidomimetics are described in Marshall G. R., (1993) Tetrahedron, 49:3547-3558. The term "chemical moieties" denotes an entity enhancing the solubility or biological activity of the LPA, and entity for directing the LPA to its target or a marker. Preferred embodiments for the sequences are described above.

The group X permits directly or indirectly continued stepwise synthesis or a fragment coupling of the same sequence, or of one or more different sequences and/or moieties. Orientation of peptide fragments (N to C or C to N) in LPA is defined as desired. In one embodiment the present invention features LPAs with N to C orientation, in another embodiment it concerns the compounds with simultaneous N to C and C to N presentation of the sequences, and in yet another embodiment the sequences have C to N orientation.

In the case where X comprises a temporally protected amino function, synthesis or coupling can be carried out directly after protection. Suitable activation of all carboxyl-containing groups providing effective formation of the ring system (on step (c), see above) can be ensured using half-equivalent carboxy acid. In case of tri- or tetracarboxylic acids the activated carboxy group may further be derivatised with a diamine such as ethylenediamine or an amine suitably functionalised for further reactions such as mercapto-, an oxy-, an oxo or carboxyl group. In the case of diamine, peptide synthesis or fragment coupling can be continued directly according to the desired sequence or chemical moiety. In a preferred embodiment, the Fmoc-protection strategy is used, but any amino protection group may be used depending on the synthesis or coupling strategy. Examples are the Boc-protection group strategy.

Since the continued stepwise synthesis or fragment coupling is performed with one or in case of a bifunctional chemical moiety such as lysine with two amino acid groups, it has surprisingly been found that a much better result can be obtained as compared to conventional tetrameric lysine dendimers obtained by the MAP synthesis. Furthermore, optimal peptide synthesis procedures or coupling procedures can be used for the single chains attached to the solid phase, and their homogeneity can be verified prior to forming the LPA. Cleavage from the solid phase and simultaneous side-chain deprotection can be performed by standard peptide synthesis procedures (described above). A final product may thus be obtained having optimal and well-defined composition. Purification by standard chromatography methods such as HPLC or gel filtration can easily be performed, if desired or needed.

Favourable di-, tri- and tetracarboxylic acids for providing the ring structure may be selected from imino diacetic acid, 2-amino malonic acid, 3-amino glutaric acid, 3-methylamino glutaric acid, 3-chloro glutamic acid, 3-methoxy-carbonyl glutaric acid, 3-acetyl glutaruc acid, glutaric acid, tricarballylic acid, 3,4-bis-carboxymethyl adipic acid, 4-(2-carboxyethyl)-pimelic acid, (3,5-bis-carboxymethyl-phenyl)-acetic acid, 3,4-bis-carboxymethyl-adipic acid, benzene-1,2,4,5-tetra carboxylic acid, 4-(3-carboxy-allylamino)-but-2-enoic acid, 4,4-imino-dibenzoic acid, 1,4-dihydropyridine-3,5-dicarboxylic acid, 5-amino isophthalic acid, 2-chloro malonic acid, 3-hydroxy glutaric acid, and benzene-1,3,5-tricarboxylic acid.

Fragment coupling (fragment coupling or fragment condensation) may be performed according to standard procedures, e.g. as described in Peptide Synthesis protocols, Methods in Molecular Biology Vol. 35, Chapter 15, 303-316, Nyfeler R, Pennington M W and Dunne B M Eds., Humana Press, 1994. Accordingly, fragments may be synthesised on a solid phase, cleaved from the solid phase with full preservation of protecting groups, purified and characterised as described above. Suitable fragments may also be obtained by other techniques described above.

It is a preferred embodiment of the invention to use the above LPA method for the production of a compound of the invention.

Medicament

It is an objective of the invention to provide a compound capable of modulating the activity of NCAM, said compound being concerned by the invention as a medicament for the treatment of diseases, wherein modulation of FGFR signaling may be considered as an essential condition for curing.

Accordingly, the invention relates to the use of one or more of the peptides comprising a sequence corresponding to NCAM or a fragment thereof or a variant for the manufacture of a medicament.

In one embodiment the medicament of the invention comprises at least one of the amino acid sequences set forth in SEQ ID NOS: 1-4 or fragments or variants of said sequences. In another embodiment the medicament of the invention comprises an antibody capable of binding to an epitope comprising NCAM or a fragment thereof or a fragment or variant of said antibody.

The medicament may in one aspect prevent death of cells in vitro or in vivo, wherein the composition is administered to a subject, in vitro or in vivo in an effective amount of one or more of the compounds described above or a composition as described below.

The medicament of the invention comprises an effective amount of one or more of the compounds as defined above, or a composition comprising compound as defined above, in combination with pharmaceutically acceptable additives. Such medicament may suitably be formulated for oral, percutaneous, intramuscular, intravenous, intracranial, intrathecal, intracerebroventricular, intranasal or pulmonal administration.

Strategies in formulation development of medicaments and compositions based on the peptides of the present invention generally correspond to formulation strategies for any other protein-based drug product. Potential problems and the guidance required to overcome these problems are dealt with in several textbooks, e.g. "Therapeutic Peptides and Protein Formulation. Processing and Delivery Systems", Ed. A. K. Banga, Technomic Publishing AG, Basel, 1995.

Injectables are usually prepared either as liquid solutions or suspensions, solid forms suitable for solution in, or suspension in, liquid prior to injection. The preparation may also be emulsified. The active ingredient is often mixed with excipients which are pharmaceutically acceptable and compatible with the active ingredient. Suitable excipients are, for example, water, saline, dextrose, glycerol, ethanol or the like, and combinations thereof. In addition, if desired, the preparation may contain minor amounts of auxiliary substances such as wetting or emulsifying agents, pH buffering agents, or which enhance the effectiveness or transportation of the preparation.

Pharmaceutical compositions containing a compound according to the present invention may be prepared by conventional techniques, e.g. as described in Remington's Pharmaceutical Sciences, 1985 or in Remington: The Science and Practice of Pharmacy, 19.sup.th edition, 1995.

In one embodiment of the invention the pharmaceutical formulation is an aqueous formulation, i.e. formulation comprising water. Such formulation is typically a solution or a suspension. In a further embodiment of the invention the pharmaceutical formulation is an aqueous solution. The term "aqueous formulation" is defined as a formulation comprising at least 50% w/w water. Likewise, the term "aqueous solution" is defined as a solution comprising at least 50% w/w water, and the term "aqueous suspension" is defined as a suspension comprising at least 50% w/w water.

One object of the present invention is to provide a pharmaceutical formulation comprising a compound according to the present invention which is present in a concentration from about 0.1 mg/ml to about 50 mg/ml, such as from about 0.1 mg/ml to about 25 mg/ml. The pH may be from 2.0 to 10.0, such as from 7.0 to 8.5 The formulation may further comprise a buffer system, preservative(s), isotonicity agent(s), chelating agent(s), stabilizers and surfactants. In a another embodiment of the invention the pH of the formulation is selected from the list consisting of 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, and 10.0. Preferably, the pH of the formulation is at least 1 pH unit from the isoelectric point of the compound according to the present invention, even more preferable the pH of the formulation is at least 2 pH unit from the isoelectric point of the compound according to the present invention.

In another embodiment the pharmaceutical formulation is a freeze-dried formulation, whereto the physician or the patient adds solvents and/or diluents prior to use, in order to obtain for example the concentrations mentioned above.

In another embodiment the pharmaceutical formulation is a dried formulation (e.g. freeze-dried or spray-dried) ready for use without any prior dissolution.

In a further aspect the invention relates to a pharmaceutical formulation comprising an aqueous solution of a compound according to the present invention, and a buffer, wherein said compound is present in a concentration from 0.1 mg/ml or above, and wherein said formulation has a pH from about 2.0 to about 10.0.

In a further aspect the invention relates to a pharmaceutical formulation comprising an aqueous solution of a compound according to the present invention, and a buffer, wherein said compound is present in a concentration from 0.1 mg/ml or above, and wherein said formulation has a pH from about 7.0 to about 8.5.

The buffer maybe selected from the group consisting of sodium acetate, sodium carbonate, citrate, glycylglycine, histidine, glycine, lysine, arginine, sodium dihydrogen phosphate, disodium hydrogen phosphate, sodium phosphate, and tris(hydroxymethyl)aminomethane, hepes, bicine, tricine, malic acid, succinate, maleic acid, fumaric acid, tartaric acid, aspartic acid or mixtures thereof. Each one of these specific buffers constitutes an alternative embodiment of the invention.

The formulation may further comprise a pharmaceutically acceptable preservative. In a further embodiment of the invention the preservative is selected from the group consisting of phenol, o-cresol, m-cresol, p-cresol, methyl p-hydroxybenzoate, propyl p-hydroxybenzoate, 2-phenoxyethanol, butyl p-hydroxybenzoate, 2-phenylethanol, benzyl alcohol, ethanol, chlorobutanol, and thimerosal, bronopol, benzoic acid, imidurea, chlorhexidine, sodium dehydroacetate, chlorocresol, ethyl p-hydroxybenzoate, benzethonium chloride, chlorphenesine (3p-chlorphenoxypropane-1,2-diol) or mixtures thereof. In a further embodiment of the invention the preservative is present in a concentration from 0.1 mg/ml to 30 mg/ml. In a further embodiment of the invention the preservative is present in a concentration from 0.1 mg/ml to 20 mg/ml. In a further embodiment of the invention the preservative is present in a concentration from 0.1 mg/ml to 5 mg/ml. In a further embodiment of the invention the preservative is present in a concentration from 5 mg/ml to 10 mg/ml. In a further embodiment of the invention the preservative is present in a concentration from 10 mg/ml to 20 mg/ml. Each one of these specific preservatives constitutes an alternative embodiment of the invention. The use of a preservative in pharmaceutical compositions is well-known to the skilled person. For convenience reference is made to Remington: The Science and Practice of Pharmacy, 19.sup.th edition, 1995.

In a further embodiment of the invention the formulation further comprises an isotonic agent. In a further embodiment of the invention the isotonic agent is selected from the group consisting of a salt (e.g. sodium chloride), a sugar or sugar alcohol, an amino acid (e.g. L-glycine, L-histidine, arginine, lysine, isoleucine, aspartic acid, tryptophan, threonine), an alditol (e.g. glycerol (glycerine), 1,2-propanediol (propyleneglycol), 1,3-propanediol, 1,3-butanediol) polyethyleneglycol (e.g. PEG400), or mixtures thereof. Any sugar such as mono-, di-, or polysaccharides, or water-soluble glucans, including for example fructose, glucose, mannose, sorbose, xylose, maltose, lactose, sucrose, trehalose, dextran, pullulan, dextrin, cyclodextrin, soluble starch, hydroxyethyl starch and carboxymethylcellulose-Na may be used. In one embodiment the sugar additive is sucrose. Sugar alcohol is defined as a C4-C8 hydrocarbon having at least one —OH group and includes, for example, mannitol, sorbitol, inositol, galacititol, dulcitol, xylitol, and arabitol. In one embodiment the sugar alcohol additive is mannitol. The sugars or sugar alcohols mentioned above may be used individually or in combination. There is no fixed limit to the amount used, as long as the sugar or sugar alcohol is soluble in the liquid preparation and does not adversely effect the stabilizing effects achieved using the methods of the invention. In one embodiment, the sugar or sugar alcohol concentration is between about 1 mg/ml and about 150 mg/ml. In a further embodiment of the invention the isotonic agent is present in a concentration from 1 mg/ml to 50 mg/ml. In a further embodiment of the invention the isotonic agent is present in a concentration from 1 mg/ml to 7 mg/ml. In a further embodiment of the invention the isotonic agent is present in a concentration from 8 mg/ml to 24 mg/ml. In a further embodiment of the invention the isotonic agent is present in a concentration from 25 mg/ml to 50 mg/ml. Each one of these specific isotonic agents constitutes an alternative embodiment of the invention. The use of an isotonic agent in pharmaceutical compositions is well-known to the skilled person. For convenience reference is made to Remington: The Science and Practice of Pharmacy, 19.sup.th edition, 1995.

In a further embodiment of the invention the formulation further comprises a chelating agent. In a further embodiment of the invention the chelating agent is selected from salts of ethylenediaminetetraacetic acid (EDTA), citric acid, and aspartic acid, and mixtures thereof. In a further embodiment of the invention the chelating agent is present in a concentration from 0.1 mg/ml to 5 mg/ml. In a further embodiment of the invention the chelating agent is present in a concentration from 0.1 mg/ml to 2 mg/ml. In a further embodiment of the invention the chelating agent is present in a concentration from 2 mg/ml to 5 mg/ml. Each one of these specific chelating agents constitutes an alternative embodiment of the invention. The use of a chelating agent in pharmaceutical compositions is well-known to the skilled person. For convenience reference is made to Remington: The Science and Practice of Pharmacy, 19.sup.th edition, 1995.

In a further embodiment of the invention the formulation further comprises a stabiliser. The use of a stabilizer in pharmaceutical compositions is well-known to the skilled person. For convenience reference is made to Remington: The Science and Practice of Pharmacy, 19.sup.th edition, 1995.

More particularly, compositions of the invention are stabilized liquid pharmaceutical compositions whose therapeutically active components include a polypeptide that possibly exhibits aggregate formation during storage in liquid pharmaceutical formulations. By "aggregate formation" is intended a physical interaction between the polypeptide molecules that results in formation of oligomers, which may remain soluble, or large visible aggregates that precipitate from the solution. By "during storage" is intended a liquid pharmaceutical composition or formulation once prepared, is not immediately administered to a subject. Rather, following preparation, it is packaged for storage, either in a liquid form, in a frozen state, or in a dried form for later reconstitution into a liquid form or other form suitable for administration to a subject. By "dried form" is intended the liquid pharmaceutical composition or formulation is dried either by freeze drying (i.e., lyophilization; see, for example, Williams and Polli (1984) J. Parenteral Sci. Technol. 38:48-59), spray drying (see Masters (1991) in Spray-Drying Handbook (5th ed; Longman Scientific and Technical, Essez, U.K.), pp. 491-676; Broadhead et al. (1992) Drug Devel. Ind. Pharm. 18:1169-1206; and Mumenthaler et al. (1994) Pharm. Res. 11:12-20), or air drying (Carpenter and Crowe (1988) Cryobiology 25:459-470; and Roser (1991) Biopharm. 4:47-53). Aggregate formation by a polypeptide during storage of a liquid pharmaceutical composition can adversely affect biological activity of that polypeptide, resulting in loss of therapeutic efficacy of the pharmaceutical composition. Furthermore, aggregate formation may cause other problems such as blockage of tubing, membranes, or pumps when the polypeptide-containing pharmaceutical composition is administered using an infusion system.

The term "stabilized formulation" refers to a formulation with increased physical stability, increased chemical stability or increased physical and chemical stability.

The term "physical stability" of the protein formulation as used herein refers to the tendency of the protein to form biologically inactive and/or insoluble aggregates of the protein as a result of exposure of the protein to thermo-mechanical stresses and/or interaction with interfaces and surfaces that are destabilizing, such as hydrophobic surfaces and interfaces. Physical stability of the aqueous protein formulations is evaluated by means of visual inspection and/or turbidity measurements after exposing the formulation filled in suitable containers (e.g. cartridges or vials) to mechanical/physical stress (e.g. agitation) at different temperatures for various time periods. Visual inspection of the formulations is performed in a sharp focused light with a dark background. The turbidity of the formulation is characterized by a visual score ranking the degree of turbidity for instance on a scale from 0 to 3 (a formulation showing no turbidity corresponds to a visual score 0, and a formulation showing visual turbidity in daylight corresponds to visual score 3). A formulation is classified physical unstable with respect to protein aggregation, when it shows visual turbidity in daylight. Alternatively, the turbidity of the formulation can be evaluated by simple turbidity measurements well-known to the skilled person. Physical stability of the aqueous protein formulations can also be evaluated by using a spectroscopic agent or probe of the conformational status of the protein. The probe is preferably a small molecule that preferentially binds to a non-native conformer of the protein. One example of a small molecular spectroscopic probe of protein structure is Thioflavin T. Thioflavin T is a fluorescent dye that has been widely used for the detection of amyloid fibrils. In the presence of fibrils, and perhaps other protein configurations as well, Thioflavin T gives rise to a new excitation maximum at about 450 nm and enhanced emission at about 482 nm when bound to a fibril protein form. Unbound Thioflavin T is essentially non-fluorescent at the wavelengths.

Other small molecules can be used as probes of the changes in protein structure from native to non-native states. For instance the "hydrophobic patch" probes that bind preferentially to exposed hydrophobic patches of a protein. The hydrophobic patches are generally buried within the tertiary structure of a protein in its native state, but become exposed as a protein begins to unfold or denature. Examples of these small molecular, spectroscopic probes are aromatic, hydrophobic dyes, such as anthracene, acridine, phenanthroline or the like. Other spectroscopic probes are metal-amino acid complexes, such as cobalt metal complexes of hydrophobic amino acids, such as phenylalanine, leucine, isoleucine, methionine, and valine, or the like.

The term "chemical stability" of the protein formulation as used herein refers to chemical covalent changes in the protein structure leading to formation of chemical degradation products with potential less biological potency and/or potential increased immunogenic properties compared to the native protein structure. Various chemical degradation products can be formed depending on the type and nature of the native protein and the environment to which the protein is exposed. Elimination of chemical degradation can most probably not be completely avoided and increasing amounts of chemical degradation products is often seen during storage and use of the protein formulation as well-known by the person skilled in the art. Most proteins are prone to deamidation, a process in which the side chain amide group in glutaminyl or asparaginyl residues is hydrolysed to form a free carboxylic acid. Other degradations pathways involves formation of high molecular weight transformation products where two or more protein molecules are covalently bound to each other through transamidation and/or disulfide interactions leading to formation of covalently bound dimer, oligomer and polymer degradation products (Stability of Protein Pharmaceuticals, Ahern. T. J. & Manning M. C., Plenum Press, New York 1992). Oxidation (of for instance methionine residues) can be mentioned as another variant of chemical degradation. The chemical stability of the protein formulation can be evaluated by measuring the amount of the chemical degradation products at various time-points after exposure to different environmental conditions (the formation of degradation products can often be accelerated by for instance increasing temperature). The amount of each individual degradation product is often determined by separation of the degradation products depending on molecule size and/or charge using various chromatography techniques (e.g. SEC-HPLC and/or RP-HPLC).

Hence, as outlined above, a "stabilized formulation" refers to a formulation with increased physical stability, increased chemical stability or increased physical and chemical stability. In general, a formulation must be stable during use and storage (in compliance with recommended use and storage conditions) until the expiration date is reached.

In one embodiment of the invention the pharmaceutical formulation comprising the compound according to the present invention is stable for more than 6 weeks of usage and for more than 3 years of storage.

In another embodiment of the invention the pharmaceutical formulation comprising the compound according to the present invention is stable for more than 4 weeks of usage and for more than 3 years of storage.

In a further embodiment of the invention the pharmaceutical formulation comprising the compound according to the present invention is stable for more than 4 weeks of usage and for more than two years of storage.

In an even further embodiment of the invention the pharmaceutical formulation comprising the compound is stable for more than 2 weeks of usage and for more than two years of storage. The pharmaceutical compositions of the invention may further comprise an amount of an amino acid base sufficient to decrease aggregate formation by the polypeptide during storage of the composition. By "amino acid base" is intended an amino acid or a combination of amino acids, where any given amino acid is present either in its free base form or in its salt form. Where a combination of amino acids is used, all of the amino acids may be present in their free base forms, all may be present in their salt forms, or some may be present in their free base forms while others are present in their salt forms. In one embodiment, amino acids used for preparing the compositions of the invention are those carrying a charged side chain, such as arginine, lysine, aspartic acid, and glutamic acid. In one embodiment, the amino acid used for preparing the compositions of the invention is glycine. Any stereoisomer (i.e. L or D) of a particular amino acid (e.g. methionine, histidine, imidazole, arginine, lysine, isoleucine, aspartic acid, tryptophan, threonine and mixtures thereof) or combinations of these stereoisomers, may be present in the pharmaceutical compositions of the invention so long as the particular amino acid is present either in its free base form or its salt form. In one embodiment the L-stereoisomer is used. Compositions of the invention may also be formulated with analogues of these amino acids. By "amino acid analogue" is intended a derivative of the naturally occurring amino acid that brings about the desired effect of decreasing aggregate formation by the polypeptide during storage of the liquid pharmaceutical compositions of the invention. Suitable arginine analogues include, for example, aminoguanidine, ornithine and N-monoethyl L-arginine, suitable methionine analogues include ethionine and buthionine and suitable cystein analogues include S-methyl-L cystein. As with the other amino acids, the amino acid analogues are incorporated into the compositions in either their free base form or their salt form. In a further embodiment of the invention the amino acids or amino acid analogues are used in a concentration, which is sufficient to prevent or delay aggregation of the protein.

In a further embodiment of the invention methionine (or other sulphuric amino acids or amino acid analogous) may be added to inhibit oxidation of methionine residues to methionine sulfoxide when the polypeptide acting as the therapeutic agent is a polypeptide comprising at least one methionine residue susceptible to such oxidation. By "inhibit" is intended minimal accumulation of methionine oxidized species over time. Inhibiting methionine oxidation results in greater retention of the polypeptide in its proper molecular form. Any stereoisomer of methionine (L, D or a mixture thereof) can be used. The amount to be added should be an amount sufficient to inhibit oxidation of the methionine residues such that the amount of methionine sulfoxide is acceptable to regulatory agencies. Typically, this means that the composition contains no more than about 10% to about 30% methionine sulfoxide. Generally, this can be achieved by adding methionine such that the ratio of methionine added to methionine residues ranges from about 1:1 to about 1000:1, such as 10:1 to about 100:1.

In a further embodiment of the invention the formulation further comprises a stabiliser selected from the group of high molecular weight polymers or low molecular compounds. In a further embodiment of the invention the stabilizer is selected from polyethylene glycol (e.g. PEG 3350), polyvinylalcohol (PVA), polyvinylpyrrolidone, carboxy-/hydroxycellulose or derivates thereof (e.g. HPC, HPC-SL, HPC-L and HPMC), cyclodextrins, sulphur-containing substances as monothioglycerol, thioglycolic acid and 2-methylthioethanol, and different salts (e.g. sodium chloride). Each one of these specific stabilizers constitutes an alternative embodiment of the invention.

The pharmaceutical compositions may also comprise additional stabilizing agents, which further enhance stability of a therapeutically active polypeptide therein. Stabilizing agents of particular interest to the present invention include, but are not limited to, methionine and EDTA, which protect the polypeptide against methionine oxidation, and a nonionic surfactant, which protects the polypeptide against aggregation associated with freeze-thawing or mechanical shearing.

In a further embodiment of the invention the formulation further comprises a surfactant. In a further embodiment of the invention the surfactant is selected from a detergent, ethoxylated castor oil, polyglycolyzed glycerides, acetylated monoglycerides, sorbitan fatty acid esters, polyoxypropylene-polyoxyethylene block polymers (e.g. poloxamers such as Pluronic® F68, poloxamer 188 and 407, Triton X-100), polyoxyethylene sorbitan fatty acid esters, starshaped PEO, polyoxyethylene and polyethylene derivatives such as alkylated and alkoxylated derivatives (tweens, e.g. Tween-20, Tween-40, Tween-80 and Brij-35), polyoxyethylene hydroxystearate, monoglycerides or ethoxylated derivatives thereof, diglycerides or polyoxyethylene derivatives thereof, alcohols, glycerol, lecitins and phospholipids (e.g. phosphatidyl serine, phosphatidyl choline, phosphatidyl ethanolamine, phosphatidyl inositol, diphosphatidyl glycerol and sphingomyelin), derivates of phospholipids (e.g. dipalmitoyl phosphatidic acid) and lysophospholipids (e.g. palmitoyl lysophosphatidyl-L-serine and 1-acyl-sn-glycero-3-phosphate esters of ethanolamine, choline, serine or threonine) and alkyl, alkoxyl (alkyl ester), alkoxy(alkyl ether)-derivatives of lysophosphatidyl and phosphatidylcholines, e.g. lauroyl and myristoyl derivatives of lysophosphatidylcholine, dipalmitoylphosphatidylcholine, and modifications of the polar head group, that is cholines, ethanolamines, phosphatidic acid, serines, threonines, glycerol, inositol, and the positively charged DODAC, DOTMA, DCP, BISHOP, lysophosphatidylserine and lysophosphatidylthreonine, and glycerophospholipids (e.g. cephalins), glyceroglycolipids (e.g. galactopyranoside), sphingoglycolipids (e.g. ceramides, gangliosides), dodecylphosphocholine, hen egg lysolecithin, fusidic acid derivatives—(e.g. sodium tauro-dihydrofusidate etc.), long-chain fatty acids and salts thereof C6-C12 (e.g. oleic acid and caprylic acid), acylcarnitines and derivatives, $N.^{\alpha}$-acylated derivatives of lysine, arginine or histidine, or side-chain acylated derivatives of lysine or arginine, $N.^{\alpha}$-acylated derivatives of dipeptides comprising any combination of lysine, arginine or histidine and a neutral or acidic amino acid, $N.^{\alpha}$-acylated derivative of a tripeptide comprising any combination of a neutral amino acid and two charged amino acids, DSS (docusate sodium, CAS registry no [577-11-7]), docusate calcium, CAS registry no [128-49-4]), docusate potassium, CAS registry no [7491-09-0]), SDS (sodium dodecyl sulfate or sodium lauryl sulfate), sodium caprylate, cholic acid or derivatives thereof, bile acids and salts thereof and glycine or taurine conjugates, ursodeoxycholic acid, sodium cholate, sodium deoxycholate, sodium taurocholate, sodium glycocholate, N-Hexadecyl-N, N-dimethyl-3-ammonio-1-propanesulfonate, anionic (alkyl-aryl-sulphonates) monovalent surfactants, zwitterionic surfactants (e.g. N-alkyl-N,N-dimethylammonio-1-propanesulfonates, 3-cholamido-1-propyldimethylammonio-1-propanesulfonate, cationic surfactants (quaternary ammonium bases) (e.g. cetyltrimethylammonium bromide, cetylpyridinium chloride), non-ionic surfactants (e.g. Dodecyl $\beta$-D-glucopyranoside), poloxamines (e.g. Tetronic's), which are tetrafunctional block copolymers derived from sequential addition of propylene oxide and ethylene oxide to ethylenediamine, or the surfactant may be selected from the group of imidazoline derivatives, or mixtures thereof. Each one of these specific surfactants constitutes an alternative embodiment of the invention.

The use of a surfactant in pharmaceutical compositions is well-known to the skilled person. For convenience reference is made to Remington: The Science and Practice of Pharmacy, 19.sup.th edition, 1995.

It is possible that other ingredients may be present in the peptide pharmaceutical formulation of the present invention. Such additional ingredients may include wetting agents, emulsifiers, antioxidants, bulking agents, tonicity modifiers, chelating agents, metal ions, oleaginous vehicles, proteins (e.g., human serum albumin, gelatin or proteins) and a zwitterion (e.g., an amino acid such as betaine, taurine, arginine, glycine, lysine and histidine). Such additional ingredients, of course, should not adversely affect the overall stability of the pharmaceutical formulation of the present invention.

Compositions of the invention may further be compounded in, or attached to, for example through covalent, hydrophobic and electrostatic interactions, a drug carrier, drug delivery system and advanced drug delivery system in order to further enhance stability of the compound, increase bioavailability, increase solubility, decrease adverse effects, achieve chronotherapy well known to those skilled in the art, and increase patient compliance or any combination thereof. Examples of carriers, drug delivery systems and advanced drug delivery systems include, but are not limited to, polymers, for example cellulose and derivatives, polysaccharides, for example dextran and derivatives, starch and derivatives, poly(vinyl alcohol), acrylate and methacrylate polymers, polylactic and polyglycolic acid and block copolymers thereof, polyethylene glycols, carrier proteins, for example albumin, gels, for example, thermogelling systems, for example block co-polymeric systems well known to those skilled in the art, micelles, liposomes, microspheres, nanoparticulates, liquid crystals and dispersions thereof, L2 phase and dispersions there of, well known to those skilled in the art of phase behaviour in lipid-water systems, polymeric micelles, multiple emulsions, self-emulsifying, self-microemulsifying, cyclodextrins and derivatives thereof, and dendrimers.

Compositions of the current invention are specifically useful in the formulation of controlled, sustained, protracting, retarded, and slow release drug delivery systems. More specifically, but not limited to, compositions are useful in formulation of parenteral controlled release and sustained release systems (both systems leading to a many-fold reduction in number of administrations), well known to those skilled in the art. Even more preferably, are controlled release and sustained release systems administered subcutaneous. Without limiting the scope of the invention, examples of useful controlled release system and compositions are hydrogels, oleaginous gels, liquid crystals, polymeric micelles, microspheres, nanoparticles, Methods to produce controlled release systems useful for compositions of the current invention include, but are not limited to, crystallization, condensation, co-crystallization, precipitation, co-precipitation, emulsification, dispersion, high pressure homogenization, encapsulation, spray drying, microencapsulation, coacervation, phase separation, solvent evaporation to produce microspheres, extrusion and supercritical fluid processes. General reference is made to Handbook of Pharmaceutical Controlled Release (Wise, D. L., ed. Marcel Dekker, New York, 2000) and Drug and the Pharmaceutical Sciences vol. 99: Protein Formulation and Delivery (MacNally, E. J., ed. Marcel Dekker, New York, 2000).

Thus, the injectable compositions of the GLP-1 derivative of the invention can be prepared using the conventional techniques of the pharmaceutical industry which involves dissolving and mixing the ingredients as appropriate to give the desired end product.

According to one procedure, the GLP-1 derivative is dissolved in an amount of water which is somewhat less than the final volume of the composition to be prepared. An isotonic agent, a preservative and a buffer is added as required and the pH value of the solution is adjusted—if necessary—using an acid, e.g. hydrochloric acid, or a base, e.g. aqueous sodium hydroxide as needed. Finally, the volume of the solution is adjusted with water to give the desired concentration of the ingredients.

Further to the above-mentioned components, solutions containing a GLP-1 derivative according to the present invention may also contain a surfactant in order to improve the solubility and/or the stability of the GLP-1 derivative.

A composition for nasal administration of certain peptides may, for example, be prepared as described in European Patent No. 272097 (to Novo Nordisk A/S) or in WO 93/18785.

According to one preferred embodiment of the present invention, the GLP-1 derivative is provided in the form of a composition suitable for administration by injection. Such a composition can either be an injectable solution ready for use or it can be an amount of a solid composition, e.g. a lyophilised product, which has to be dissolved in a solvent before it can be injected. The injectable solution preferably contains not less than about 2 mg/ml, preferably not less than about 5 mg/ml, more preferred not less than about 10 mg/ml of the GLP-1 derivative and, preferably, not more than about 100 mg/ml of the GLP-1 derivative.

Formulations of the compounds of the invention can be prepared by techniques known to the person skilled in the art. The formulations may contain pharmaceutically acceptable carriers and excipients including microspheres, liposomes, microcapsules, nanoparticles or the like as described above.

Pharmaceutical compositions containing a compound according to the present invention may be administered to a patient in need of such treatment at several sites, for example, at topical sites, for example, skin and mucosal sites, at sites which bypass absorption, for example, administration in an artery, in a vein, in the heart, and at sites which involve absorption, for example, administration in the skin, under the skin, in a muscle or in the abdomen.

Administration of pharmaceutical compositions according to the invention may be through several routes of administration, for example, lingual, sublingual, buccal, in the mouth, oral, in the stomach and intestine, nasal, pulmonary, for example, through the bronchioles and alveoli or a combination thereof, epidermal, dermal, transdermal, vaginal, rectal, ocular, for examples through the conjunctiva, uretal, and parenteral to patients in need of such a treatment.

Compositions of the current invention may be administered in several dosage forms, for example, as solutions, suspensions, emulsions, microemulsions, multiple emulsion, foams, salves, pastes, plasters, ointments, tablets, coated tablets, rinses, capsules, for example, hard gelatine capsules and soft gelatine capsules, suppositories, rectal capsules, drops, gels, sprays, powder, aerosols, inhalants, eye drops, ophthalmic ointments, ophthalmic rinses, vaginal pessaries, vaginal rings, vaginal ointments, injection solution, in situ transforming solutions, for example in situ gelling, in situ setting, in situ precipitating, in situ crystallization, infusion solution, and implants.

Compositions of the current invention are useful in the formulation of solids, semi-solids, powder and solutions for pulmonary administration of the compound, using, for example a metered dose inhaler, dry powder inhaler and a nebulizer, all being devices well known to those skilled in the art.

Parenteral administration may be performed by subcutaneous, intramuscular, intraperitoneal or intravenous injection by means of a syringe, optionally a pen-like syringe. Alternatively, parenteral administration can be performed by means of an infusion pump. A further option is a composition which may be a solution or suspension for the administration of the compound according to the present invention in the form of a nasal or pulmonal spray. As a still further option, the pharmaceutical compositions containing the compound of the invention can also be adapted to transdermal administration, e.g. by needle-free injection or from a patch, optionally an iontophoretic patch, or transmucosal, e.g. buccal, administration.

Other formulations are such suitable for nasal and pulmonal administration, e.g. inhalators and aerosols.

The active compound may be formulated as neutral or salt forms. Pharmaceutically acceptable salts include acid addition salts (formed with the free amino groups of the peptide compound) and which are formed with inorganic acids such as, for example, hydrochloric or phosphoric acids, or such organic acids as acetic acid, oxalic acid, tartaric acid, mandelic acid, and the like. Salts formed with the free carboxyl group may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The preparations are administered in a manner compatible with the dosage formulation, and in such amount as will be therapeutically effective. The quantity to be administered depends on the subject to be treated, including, e.g. the weight and age of the subject, the disease to be treated and the stage of disease. Suitable dosage ranges are per kilo body weight normally of the order of several hundred μg active ingredient per administration with a preferred range of from about 0.1 μg to 5000 μg per kilo body weight. Using monomeric forms of the compounds, the suitable dosages are often in the range of from 0.1 μg to 5000 μg per kilo body weight, such as in the range of from about 0.1 μg to 3000 μg per kilo body weight, and especially in the range of from about 0.1 μg to 1000 μg per kilo body weight. Using multimeric forms of the compounds, the suitable dosages are often in the range of from 0.1 μg to 1000 μg per kilo body weight, such as in the range of from about 0.1 μg to 750 μg per kilo body weight, and especially in the range of from about 0.1 μg to 500 μg per kilo body weight such as in the range of from about 0.1 μg to 250 μg per kilo body weight. In particular when administering nasally smaller dosages are used than when administering by other routes. Administration may be performed once or may be followed by subsequent administrations. The dosage will also depend on the route of administration and will vary with the age and weight of the subject to be treated. A preferred dosage of multimeric forms would be in the interval 1 mg to 70 mg per 70 kg body weight.

For most indications a localised or substantially localised application is preferred.

Some of the compounds of the present invention are sufficiently active, but for some of the others, the effect will be enhanced if the preparation further comprises pharmaceutically acceptable additives and/or carriers. Such additives and carriers will be known in the art. In some cases, it will be advantageous to include a compound, which promotes delivery of the active substance to its target as described above.

In many instances, it will be necessary to administrate the formulation multiple times. Administration may be a continuous infusion, such as intraventricular infusion or administration in more doses such as more times a day, daily, more times a week, weekly, etc. It is preferred that administration of the medicament is initiated before or shortly after the individual has been subjected to the factor(s) that may lead to cell death. Preferably the medicament is administered within 8 hours from the factor onset, such as within 5 hours from the factor onset. Many of the compounds exhibit a long term effect whereby administration of the compounds may be conducted with long intervals, such as 1 week or 2 weeks.

In connection with the use in nerve guides, the administration may be continuous or in small portions based upon controlled release of the active compound(s). Furthermore, precursors may be used to control the rate of release and/or site of release. Other kinds of implants and well as oral administration may similarly be based upon controlled release and/or the use of precursors.

As discussed above, the present invention relates to treatment of individuals for inducing differentiation, modulating proliferation, stimulate regeneration, neuronal plasticity and survival of cells in vitro or in vivo, the treatment involving administering an effective amount of one or more compounds as defined above.

Another strategy for administration is to implant or inject cells capable of expressing and secreting the compound in question. Thereby the compound may be produced at the location where it is going to act.

Treatment

The compounds according to the invention are particularly useful for treating neurodegenerative diseases, as well as conditions with impaired cognition, and the treatment according to the invention is in one embodiment useful for inducing differentiation, modulating proliferation, stimulating regeneration, neuronal plasticity and survival of cells, for example cells being implanted or transplanted. The compounds are useful for the diseases and conditions mentioned below, in particular useful for the treatment of Alzheimer's disease, Parkinson's disease, Huntington's disease, cerebral ischemia, as well as stress.

In further embodiment the treatment may be for stimulation of survival of cells which are at risk of dying due to a variety of factors, such as traumas and injuries, acute diseases, chronic diseases and/or disorders, in particular degenerative diseases normally leading to cell death, other external factors, such as medical and/or surgical treatments and/or diagnostic methods that may cause formation of free radicals or otherwise have cytotoxic effects, such as X-rays and chemotherapy. In relation to chemotherapy peptides according to the invention are useful in cancer treatment.

Thus, the treatment comprises treatment and/or prophylaxis of cell death in relation to diseases or conditions of the central and peripheral nervous system, such as postoperative nerve damage, traumatic nerve damage, e.g. resulting from spinal cord injury, impaired myelination of nerve fibers, postischaemic damage, e.g. resulting from a stroke, multiinfarct dementia, multiple sclerosis, nerve degeneration associated with diabetes mellitus, neuro-muscular degeneration, schizophrenia, Alzheimer's disease, Parkinson's disease, or Huntington's disease.

Also, in relation to diseases or conditions of the muscles including conditions with impaired function of neuro-muscular connections, such as genetic or traumatic atrophic muscle disorders; or for the treatment of diseases or conditions of various organs, such as degenerative conditions of the gonads, of the pancreas, such as diabetes mellitus type I and II, of the kidney, such as nephrosis the compounds according to the invention may be used for inducing differentiation, modulating proliferation, stimulate regeneration, neuronal plasticity and survival, i.e. stimulating survival.

Furthermore, the treatment may be for preventing cell death of heart muscle cells, such as after acute myocardial infarction, in order to induce angiogenesis. Furthermore, in one embodiment the treatment is for the stimulation of the survival of heart muscle cells, such as survival after acute myocardial infarction. In another aspect the treatment is for revascularisation, such as after injuries.

It is also within the scope of the invention a use of the peptides for the promotion of wound-healing. The present peptides are capable of stimulating angiogenesis and thereby they can promote the wound healing process.

The invention further discloses a use of peptides in the treatment of cancer. Regulation of activation of receptor tyrosine kinases is important for tumor agiogenesis, proliferation and spreading.

In yet a further embodiment a use of the peptides is for the stimulation of the ability to learn and/or of the short and/or long term memory, as FGFR activity is important for differentiation of neural cells.

In still another embodiment a peptide for use according to the invention is for the treatment of body damages due to alcohol consumption. Developmental malformations of foetuses, long-term neurobehavioral alterations, alcoholic liver disease are particularly concerned.

Therapeutic treatment of prion diseases including using a peptide is still another embodiment of the invention.

In particular the use according to the invention of a peptide may be for the treatment of clinical conditions, such as neoplasms such as malignant neoplasms, benign neoplasms, carcinoma in situ and neoplasms of uncertain behavior, cancer in breast, thyroidal, pancreas, brain, lung, kidney, prostate, liver, heart, skin, blood organ, muscles (sarcoma), cancers with dysfunction and/or over- or under-expression of specific receptors and/or expression of mutated receptors or associated with soluble receptors, such as but not limited to Erb-receptors and FGF-receptors, diseases of endocrine glands, such as diabetes mellitus I and II, pituitary gland tumor, psychoses, such as senile and presenile organic psychotic conditions, alcoholic psychoses, drug psychoses, transient organic psychotic conditions, Alzheimer's disease, cerebral lipidoses, epilepsy, general paresis [syphilis], hepatolenticular degeneration, Huntington's chorea, Jakob-Creutzfeldt disease, multiple sclerosis, Pick's disease of the brain, polyareriti nodosa, syphilis, schizophrenic disorders, affective psychoses, neurotic disorders, personality disorders, including character neurosis, nonpsychotic personality disorder associated with organic brain syndromes, paranoid personality disorder, fanatic personality, paranoid personality (disorder), paranoid traits, sexual deviations and disorders or dysfunctions (including reduced sexual drive for what ever reason), mental retardation, disease in the nervesystem and sense organs, such as affecting sight, hearing, smell, feeling, tasting, cognitive anomalies after disease, injury (e.g. after trauma, surgical procedure, and violence), inflammatory disease of the central nervous system, such as meningitis, encephalitis, cerebral degenerations such as Alzheimer's disease, Pick's disease, senile degeneration of brain, senility NOS, communicating hydrocephalus, obstructive hydrocephalus, Parkinson's disease including other extra pyramidal disease and abnormal movement disorders, spinocerebellar disease, cerebellar ataxia, Marie's Sanger-Brown, Dyssynergia cerebellaris myoclonica, primary cerebellar degeneration, such as spinal muscular atrophy, familial, juvenile, adult spinal muscular atrophy, motor neuron disease, amyotrophic lateral sclerosis, motor neuron disease, progressive bulbar palsy, pseudobulbar palsy, primary lateral sclerosis, other anterior horn cell diseases, anterior horn cell disease, unspecified, other diseases of spinal cord, syringomyelia and syringobulbia, vascular myelopathies, acute infarction of spinal cord (embolic) (nonembolic), arterial thrombosis of spinal cord, edema of spinal cord, hematomyelia, subacute necrotic myelopathy, subacute combined degeneration of spinal cord in diseases classified elsewhere, myelopathy, drug-induced, radiation-induced myelitis, disorders of the autonomic nervous system, disorders of peripheral autonomic, sympathetic, parasympathetic, or vegetative system, familial dysautonomia [Riley-Day syndrome], idiopathic peripheral autonomic neuropathy, carotid sinus syncope or syndrome, cervical sympathetic dystrophy or paralysis. peripheral autonomic neuropathy in disorders classified elsewhere, amyloidosis, diseases of the peripheral nerve system, brachial plexus lesions, cervical rib syndrome, costoclavicular syndrome, scalenus anticus syndrome, thoracic outlet syndrome, brachial neuritis or radiculitis NOS, including in newborn. Inflammatory and toxic neuropathy, including acute infective polyneuritis, Guillain-Barre syndrome, Postinfectious polyneuritis, polyneuropathy in collagen vascular disease, disorders of the globe including disorders affecting multiple structures of eye, such as purulent endophthalmitis, diseases of the ear and mastoid process, chronic rheumatic heart disease, ischaemic heart disease, arrhythmia, diseases in the pulmonary system, respiratory system, sensoring e.g. oxygene, astma, abnormality of organs and soft tissues in newborn, including in the nerve system, complications of the administration of anesthetic or other sedation in labor and delivery, diseases in the skin including infection, insufficient circulation problem, burn injury and other mechanic and/or physical injuries, injuries, including after surgery, crushing injury, burns. Injuries to nerves and spinal cord, including division of nerve, lesion in continuity (with or without open wound), traumatic neuroma (with or without open wound), traumatic transient paralysis (with or without open wound), accidental puncture or laceration during medical procedure, injury to optic nerve and pathways, optic nerve injury, second cranial nerve, injury to optic chiasm, injury to optic pathways, injury to visual cortex, unspecified blindness, injury to other cranial nerve(s), injury to other and unspecified nerves, poisoning by drugs, medicinal and biological substances, genetic or traumatic atrophic muscle disorders; or for the treatment of diseases or conditions of various organs, such as degenerative conditions of the gonads, of the pancreas, such as diabetes mellitus type I and II, of the kidney, such as nephrosis. Scrapie, Creutzfeldt-Jakob disease, Gerstmann-Straussler-Sheinker (GSS) disease; pain syndrome, encephalitis, drug/alcohol abuse, anxiety, postoperative nerve damage, peri-operative ischemia, inflammatory disorders with tissue damage, either by affecting the infections agent or protecting the tissue, HIV, hepatitis, and following symptoms, autoimmune disorders, such as rheumatoid arthritis, SLE, ALS, and MS. Anti-inflammatory effects, asthma and other allergic reactions, acute myocardial infarction, and other related disorders or sequel from AMI, metabolic disorders, such as obscenity lipid disorders (e.g. hyper cholestorolamia, artheslerosis, disorders of amino-acid transport and metabolism, disorders of purine and pyrimidine metabolism and gout, bone disorders, such as fracture, osteoporosis, osteo arthritis (OA), Atrophic dermatitis, psoriasis, infection cased disorders, stem cell protection or maturation in vivo or in vitro.

In yet a further embodiment the medicament is administered for increasing well being, such as stimulation of sexual motivation, desire or pleasure. The well-being may be physically as well as physiologically.

Antibody

It is an objective of the present invention to provide the use of an antibody, antigen binding fragment or recombinant protein thereof capable of selectively binding to an epitope comprising a contiguous amino acid sequence derived from NCAM or a fragment, homologue or variant thereof. The invention relates to any antibody capable of selectively binding to an epitope comprising a contiguous amino acid sequence derived from NCAM, selected from any of the sequences set forth in SEQ ID NOS: 1-4, or a fragment or variant of said sequence.

By the term "epitope" is meant the specific group of atoms (on an antigen molecule) that is recognized by (that antigen's) antibodies. The term "epitope" is the equivalent to the term "antigenic determinant". The epitope may comprise 3 or more amino acid residues, such as for example 4, 5, 6, 7, 8 amino acid residues, located in close proximity, such as within a contiguous amino acid sequence, or located in distant parts of the amino acid sequence of an antigen, but due to protein folding have been approached to each other.

Antibody molecules belong to a family of plasma proteins called immunoglobulins, whose basic building block, the immunoglobulin fold or domain, is used in various forms in many molecules of the immune system and other biological recognition systems. A typical immunoglobulin has four polypeptide chains, containing an antigen binding region known as a variable region and a non-varying region known as the constant region.

Native antibodies and immunoglobulins are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end. The constant domain of the light chain is aligned with the first constant domain of the heavy chain, and the light chain variable domain is aligned with the variable domain of the heavy chain. Particular amino acid residues are believed to form an interface between the light and heavy chain variable domains (Novotny J, & Haber E. Proc Natl Acad Sci USA. 82(14):4592-6, 1985).

Depending on the amino acid sequences of the constant domain of their heavy chains, immunoglobulins can be assigned to different classes. There are at least five (5) major classes of immunoglobulins: IgA, IgD, IgE, IgG and IgM, and several of these may be further divided into subclasses (isotypes), e.g. IgG-1, IgG-2, IgG-3 and IgG-4; IgA-1 and IgA-2. The heavy chains constant domains that correspond to the different classes of immunoglobulins are called alpha (α), delta (δ), epsilon (ε), gamma (γ) and mu (μ), respectively. The light chains of antibodies can be assigned to one of two clearly distinct types, called kappa (κ) and lambda (λ), based on the amino sequences of their constant domain. The subunit structures and three-dimensional configurations of different classes of immunoglobulins are well known.

The term "variable" in the context of variable domain of antibodies, refers to the fact that certain portions of the variable domains differ extensively in sequence among antibodies. The variable domains are for binding and determine the specificity of each particular antibody for its particular antigen. However, the variability is not evenly distributed through the variable domains of antibodies. It is concentrated in three segments called complementarity determining regions (CDRs) also known as hypervariable regions both in the light chain and the heavy chain variable domains.

The more highly conserved portions of variable domains are called the framework (FR). The variable domains of native heavy and light chains each comprise four FR regions, largely adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the antigen-binding site of antibodies. The constant domains are not involved directly in binding an antibody to an antigen, but exhibit various effector functions, such as participation of the antibody in antibody-dependent cellular toxicity.

An antibody that is contemplated for use in the present invention thus can be in any of a variety of forms, including a whole immunoglobulin, an antibody fragment such as Fv, Fab, and similar fragments, a single chain antibody which includes the variable domain complementarity determining regions (CDR), and the like forms, all of which fall under the broad term "antibody", as used herein. The present invention contemplates the use of any specificity of an antibody, polyclonal or monoclonal, and is not limited to antibodies that recognize and immunoreact with a specific antigen. In the context of both the therapeutic and screening methods described below, preferred embodiments are the use of an antibody or fragment thereof that is immunospecific for an antigen or epitope of the invention.

The term "antibody fragment" refers to a portion of a full-length antibody, generally the antigen binding or variable region. Examples of antibody fragments include Fab, Fab', F(ab')$_2$ and Fv fragments. Papain digestion of antibodies produces two identical antigen binding fragments, called the Fab fragment, each with a single antigen binding site, and a residual "Fc" fragment, so-called for its ability to crystallize readily. Pepsin treatment yields an F(ab')$_2$ fragment that has two antigen binding fragments that are capable of cross-linking antigen, and a residual other fragment (which is termed pFc'). Additional fragments can include diabodies, linear antibodies, single-chain antibody molecules, and multispecific antibodies formed from antibody fragments. As used herein, "functional fragment" with respect to antibodies, refers to Fv, F(ab) and F(ab')$_2$ fragments.

The term "antibody fragment" is used herein interchangeably with the term "antigen binding fragment".

Antibody fragments may be as small as about 4 amino acids, 5 amino acids, 6 amino acids, 7 amino acids, 9 amino acids, about 12 amino acids, about 15 amino acids, about 17 amino acids, about 18 amino acids, about 20 amino acids, about 25 amino acids, about 30 amino acids or more. In general, an antibody fragment of the invention can have any upper size limit so long as it is has similar or immunological properties relative to antibody that binds with specificity to an epitope comprising a peptide sequence selected from any of the sequences identified herein as SEQ ID NOs: 1-13, or a fragment of said sequences. Thus, in context of the present invention the term "antibody fragment" is identical to term "antigen binding fragment".

Antibody fragments retain some ability to selectively bind with its antigen or receptor. Some types of antibody fragments are defined as follows:
(1) Fab is the fragment that contains a monovalent antigen-binding fragment of an antibody molecule. A Fab fragment can be produced by digestion of whole antibody with the enzyme papain to yield an intact light chain and a portion of one heavy chain.
(2) Fab' is the fragment of an antibody molecule can be obtained by treating whole antibody with pepsin, followed by reduction, to yield an intact light chain and a portion of the heavy chain. Two Fab' fragments are obtained per antibody molecule.
Fab' fragments differ from Fab fragments by the addition of a few residues at the carboxyl terminus of the heavy chain CH1 domain including one or more cysteines from the antibody hinge region.
(3) (Fab')$_2$ is the fragment of an antibody that can be obtained by treating whole antibody with the enzyme pepsin without subsequent reduction.
(4) F(ab')$_2$ is a dimer of two Fab' fragments held together by two disulfide bonds.

Fv is the minimum antibody fragment that contains a complete antigen recognition and binding site. This region consists of a dimer of one heavy and one light chain variable domain in a tight, non-covalent association ($V_H$-$V_L$ dimer). It is in this configuration that the three CDRs of each variable domain interact to define an antigen binding site on the surface of the $V_H$-$V_L$ dimer. Collectively, the six CDRs confer antigen binding specificity to the antibody. However, even a single variable domain (or half of an Fv comprising only three CDRs specific for an antigen) has the ability to recognize and bind antigen, although at a lower affinity than the entire binding site.

(5) Single chain antibody ("SCA"), defined as a genetically engineered molecule containing the variable region of the light chain, the variable region of the heavy chain, linked by a suitable polypeptide linker as a genetically fused single chain molecule. Such single chain antibodies are also referred to as "single-chain Fv" or "sFv" antibody fragments. Generally, the Fv polypeptide further comprises a polypeptide linker between the VH and VL domains that enables the sFv to form the desired structure for antigen binding. For a review of sFv see Pluckthun in The Pharmacology of Monoclonal Antibodies 113: 269-315 Rosenburg and Moore eds. Springer-Verlag, NY, 1994.

The term "diabodies" refers to small antibody fragments with two antigen-binding sites, which fragments comprise a heavy chain variable domain (VH) connected to a light chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies are described more fully in, for example, EP 404,097; WO 93/11161, and Hollinger et al., Proc. Natl. Acad Sci. USA 90: 6444-6448 (1993).

The invention also contemplates multivalent antibodies having at least two binding domains. The binding domains may have specificity for the same ligand or for different ligands. In one embodiment the multispecific molecule is a bispecific antibody (BsAb), which carries at least two different binding domains, at least one of which is of antibody origin. Multivalent antibodies may be produced by a number of methods. Various methods for preparing bi- or multivalent antibodies are for example described in U.S. Pat. Nos. 5,260,203; 5,455,030; 4,881,175; 5,132,405; 5,091,513; 5,476,786; 5,013,653; 5,258,498; and 5,482,858.

The invention contemplate both polyclonal and monoclonal antibody, antigen binding fragments and recombinant proteins thereof which are capable of binding an epitope according to the invention.

The preparation of polyclonal antibodies is well-known to those skilled in the art. See, for example, Green et al. 1992. Production of Polyclonal Antisera, in: Immunochemical Protocols (Manson, ed.), pages 1-5 (Humana Press); Coligan, et al., Production of Polyclonal Antisera in Rabbits, Rats Mice and Hamsters, in: Current Protocols in Immunology, section 2.4.1, which are hereby incorporated by reference.

The preparation of monoclonal antibodies likewise is conventional. See, for example, Kohler & Milstein, Nature, 256: 495-7 (1975); Coligan, et al., sections 2.5.1-2.6.7; and Harlow, et al., in: Antibodies: A Laboratory Manual, page 726, Cold Spring Harbor Pub. (1988), Monoclonal antibodies can be isolated and purified from hybridoma cultures by a variety of well-established techniques. Such isolation techniques include affinity chromatography with Protein-A Sepharose, size-exclusion chromatography, and ion-exchange chromatography. See, e.g., Coligan, et al., sections 2.7.1-2.7.12 and sections 2.9.1-2.9.3; Barnes, et al., Purification of Immunoglobulin G (IgG). In: Methods in Molecular Biology, 1992, 10:79-104, Humana Press, NY.

Methods of in vitro and in vivo manipulation of monoclonal antibodies are well known to those skilled in the art. For example, the monoclonal antibodies to be used in accordance with the present invention may be made by the hybridoma method first described by Kohler and Milstein, 1975, Nature 256, 495-7, or may be made by recombinant methods, e.g., as described in U.S. Pat. No. 4,816,567. The monoclonal antibodies for use with the present invention may also be isolated from phage antibody libraries using the techniques described in Clackson et al., 1991, Nature 352: 624-628, as well as in Marks et al., 1991, J Mol Biol 222: 581-597. Another method involves humanizing a monoclonal antibody by recombinant means to generate antibodies containing human specific and recognizable sequences. See, for review, Holmes, et al., 1997, J Immunol 158:2192-2201 and Vaswani, et al., 1998, Annals Allergy, Asthma & Immunol 81:105-115.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional polyclonal antibody preparations that typically include different antibodies directed against different determinants (epitopes), each monoclonal antibody is directed against a single determinant on the antigen. In additional to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567); Morrison et al., 1984, Proc Natl Acad Sci 81: 6851-6855.

Methods of making antibody fragments are also known in the art (see for example, Harlow and Lane, Antibodies: A Laboratory Manual, Cold Spring Harbor Laboratory, NY, 1988, incorporated herein by reference). Antibody fragments of the present invention can be prepared by proteolytic hydrolysis of the antibody or by expression in E. coli of DNA encoding the fragment. Antibody fragments can be obtained by pepsin or papain digestion of whole antibodies conventional methods. For example, antibody fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, in U.S. Pat. Nos. 4,036,945 and 4,331,647, and references contained therein. These patents are hereby incorporated in their entireties by reference.

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody. For example, Fv fragments comprise an association of $V_H$ and $V_L$ chains. This association may be noncovalent or the variable chains can be linked by an intermolecular disulfide bond or cross-linked by chemicals such as glutaraldehyde. Preferably, the Fv fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains connected by an oligonucleotide. The structural gene is inserted into an expression vector, which is subsequently introduced into a host cell such as E. coli. The recombinant host cells synthesize a single polypeptide chain with a linker peptide bridging the two V domains. Methods for producing sFvs are described, for example, by Whitlow, et al., 1991, In: Methods: A Companion to Methods in Enzymology, 2:97; Bird et al., 1988, Science 242:423-426; U.S. Pat. No. 4,946,778; and Pack, et al., 1993, BioTechnology 11:1271-77.

Another form of an antibody fragment is a peptide coding for a single complementarity-determining region (CDR). CDR peptides ("minimal recognition units") are often involved in antigen recognition and binding. CDR peptides can be obtained by cloning or constructing genes encoding the CDR of an antibody of interest. Such genes are prepared, for example, by using the polymerase chain reaction to synthesize the variable region from RNA of antibody-producing cells. See, for example, Larrick, et al., Methods: a Companion to Methods in Enzymology, Vol. 2, page 106 (1991).

The invention contemplates human and humanized forms of non-human (e.g. murine) antibodies. Such humanized antibodies are chimeric immunoglobulins, immunoglobulin chains or fragments thereof (such as Fv, Fab, Fab', F(ab')$_2$ or other antigen-binding subsequences of antibodies) that contain a minimal sequence derived from non-human immunoglobulin, such as the eitope recognising sequence. For the most part, humanized antibodies are human immunoglobulins (recipient antibody) in which residues from a complementary determining region (CDR) of the recipient are replaced by residues from a CDR of a nonhuman species (donor antibody) such as mouse, rat or rabbit having the desired specificity, affinity and capacity. Humanized antibody(es) containing a minimal sequence(s) of antibody(es) of the invention, such as a sequence(s) recognising an epitope(s) described herein, is one of the preferred embodiments of the invention.

In some instances, Fv framework residues of the human immunoglobulin are replaced by corresponding non-human residues. Furthermore, humanized antibodies may comprise residues that are found neither in the recipient antibody nor in the imported CDR or framework sequences. These modifications are made to further refine and optimize antibody performance. In general, humanized antibodies will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin. For further details, see: Jones et al., 1986, Nature 321, 522-525; Reichmann et al., 1988, Nature 332, 323-329; Presta, 1992, Curr Op Struct Biol 2:593-596; Holmes et al., 1997, J Immunol 158:2192-2201 and Vaswani, et al., 1998, Annals Allergy, Asthma & Immunol 81:105-115.

The generation of antibodies may be achieved by any standard methods in the art for producing polyclonal and monoclonal antibodies using natural or recombinant fragments of a sequence selected from any of the sequences identified as SEQ ID NOs: 1-4, as an antigen. Such antibodies may be also generated using variants or fragments of SEQ ID NOs: 1-4.

The antibodies may also be produced in vivo by the individual to be treated, for example, by administering an immunogenic fragment according to the invention to said individual. Accordingly, the present invention further relates to a vaccine comprising an immunogenic fragment described above.

The application also relates to a method for producing an antibody of the invention said method comprising a step of providing of an immunogenic fragment described above.

The invention relates both to an antibody, which is capable of modulating, such as enhancing or attenuating, biological function of NCAM in particular a function related to neural cell growth and survival, and to an antibody, which can recognise and specifically bind to NCAM without modulating biological activity thereof.

The invention relates to use of the above antibodies for therapeutic applications involving the modulation of activity of NCAM.

In one aspect the invention relates to the use of a pharmaceutical composition comprising an antibody described above.

EXAMPLES

1. The Effect of FGLs on Activation of FGFR1c in Trex293 Cells

Figure 1:
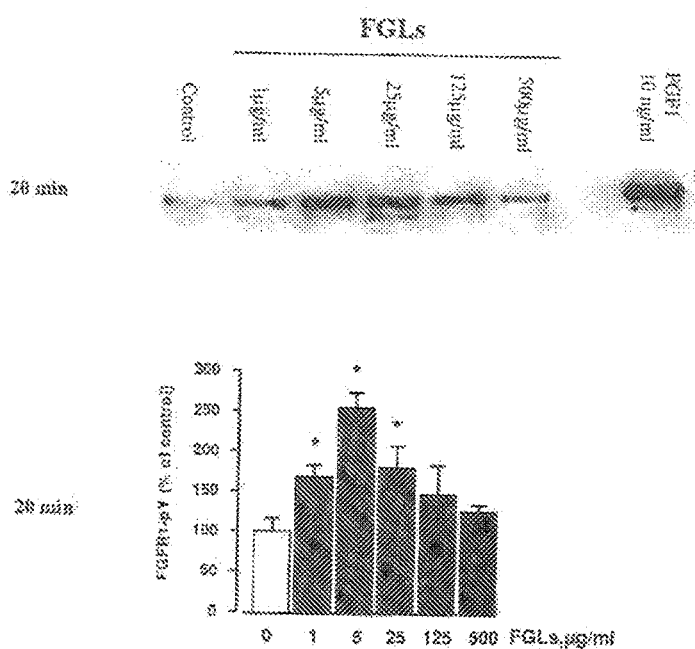
FIG. 1. Dose dependent effect of FGLs on activation of the FGFR. Trex293 cells (Invitrogen) were stably transfected with human FGFR1, splice variant IIIc, with a C-terminal Strep II tag. For determination of phosphorylation, $2 \times 10^6$ cells were starved overnight in medium without serum. After treatment with FGLs, at concentration between 1 and 500 □g/ml, or FGF1 (10 ngml) for 20 minutes, the cells were lysed and purified phospho-proteins were obtained by use of agarose coupled anti-phosphotyrosine antibodies. The purified proteins were separated by SDS-PAGE and transferred to a polyvinylidene fluoride membrane. Immunoblotting was performed using rabbit antibodies against the recombinant StrepII tag. The immune complexes were developed and then visualized and quantified using SynGene Gene Tool image analysis software. The results are given as mean values±SEM from at least three independent experiments and are illustrated as percentage of control values. *p<0.05 when compared with control by paired t-test.

This study investigated the effect of FGLs on FGFR1c phosphorylation in Trex293 cells overexpressing the human FGFR1c. The results of this study show that FGLs induces significant phosphorylation of the FGFR1c. The dose response curve is bell-shaped with significant activity at the concentration range of 1 to 25 □g/ml (FIG. 1).

FGLs induces activation (phosphorylation) of its target, the FGFR. The dose-response of such activation is bell-shaped, as expected by a growth factor like activity studied in vitro. The decrease of effects seen at high concentration of ligand is often related to a decreased availability of receptors on the cell membrane due to a combination of saturation of available receptors by excess ligand, and of internalization of bound receptors.

Figure 2:
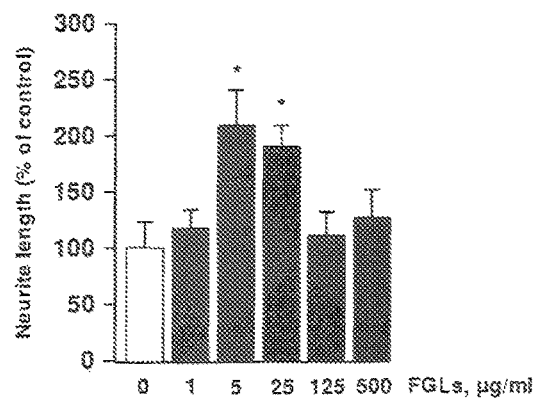
FIG. 2. Effects of FGLs on neurite outgrowth of early postnatal rat cerebellar neurons. CGCs were prepared from 7-day old Wistar rats and plated on uncoated eight-well Lab-Tek® chamber The peptide was added to the medium immediately after plating, and cells were maintained at 37° C., 5% $CO_2$ for 24 hrs. CGC cultures were fixed in 4% and then immunostained against rat GAP-43. Neurite outgrowth was determined by image analysis of 200±20 neurons in each individual experiment. The length of neuronal processes per cell was estimated stereologically. The results are given as mean values±SEM from at least three independent experiments and illustrated as percentage of control values. *p<0.05 when compared with control by paired t-test.

2. An In Vitro Study of the Effect of FGLs on Neurite Outgrowth of Cerebellar Rat Neurons This study investigated the effect of FGLs on neurite outgrowth of dissociated primary cerebellar granule rat cells (CGC) cultured in vitro. The results indicate that FGLs promoted neurite outgrowth from CGC (FIG. 2), with activity at the concentration range 5-25 □g/ml, which corresponds well to that inducing FGFR activation (see FIG. 2).

FGLs has a neuritogenic effect on cerebellar granule neurons obtained from early postnatal rats, suggesting that it promotes neuronal differentiation. Efficacy is found over a range of concentrations corresponding to that of target (FGFR) activation and follows the same bell-shaped dose-response.

3. Randomized, Single-blinded, Placebo Controlled Studies of the Effect of Subcutaneous Administration of FGLs, VEB1, and $FGL_L$ Peptides on Social Memory, using the Social Recognition Test.

Figure 3:
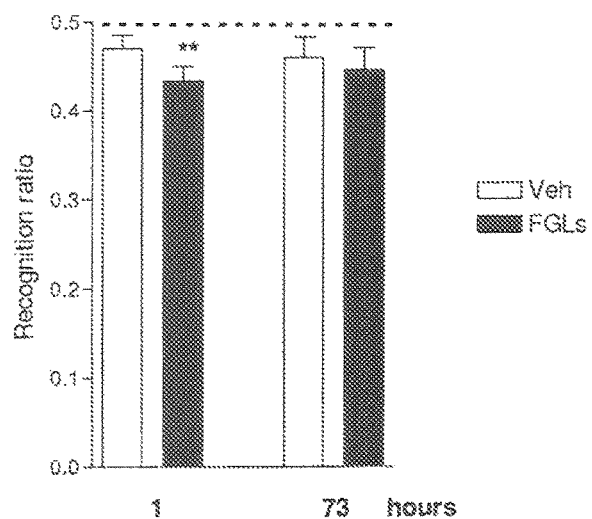
FIG. 3. Effects of a single administration of vehicle or of FGLs on short-term social memory as evaluated in the Social Recognition Test (SRT). FGLs (8.0 mg/kg) or vehicle (sterile water, 4.0 ml/kg) was administered s.c. and the rats were tested twice with the initial trial of SRT performed 1 h and 73 h after administration. The juvenile rat was presented twice with an inter-trial interval of 2 hours. In each experimental group data were obtained from 9 to 11 rats. Results are shown as Mean and SEM of recognition ratio (RR). A RR value significantly below 0.5 indicates social memory. Comparisons of RR values to a hypothetical value 0.50 were carried using one-sample t-test. **P<0.01.

The activity of FGLs, administered subcutaneously, in enhancing social memory in intact adult rats was examined in three studies. In both studies the test system was the Social Recognition Test (SRT), which is a reliable test for the evaluation of compounds active on short-term memory (Dantzer et al., 1987). In our studies we used a protocol of SRT were a juvenile rat was presented to the test rat twice, with an inter-trial interval (ITI) of 2 hours between the two tests. This inter-trial interval was chosen on the basis of previous investigations on the dynamics of social recognition memory that showed that at this ITI, normal rats do not show significant social memory Secher et al., 2006). In the first study the rats received a single subcutaneous dose (8.0 mg/kg) of FGLs and were tested 1 hour and 73 hours after administration. A significant memory enhancing effect of FGLs was detected 1 hour post administration, while a tendency to significance (p=0.06) was seen 73 hours after administration (FIG. 3).

Figure 4:
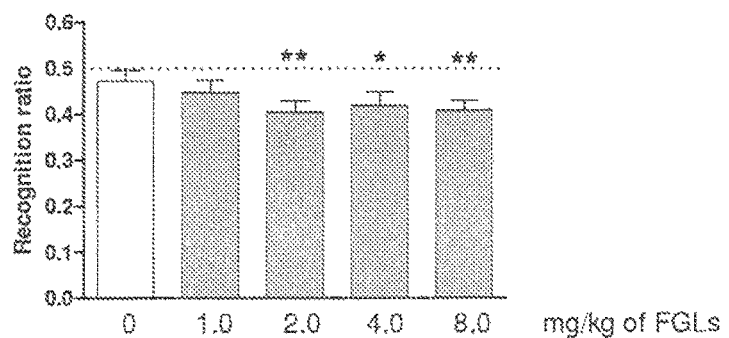
FIG. 4. Effects of a single administration of vehicle or of FGLs on short-term social memory as evaluated in the Social Recognition Test (SRT). FGLs (1.0, 2.0, 4.0 and 8.0 mg/kg) or vehicle (sterile water, 4.0 ml/kg) was administered s.c. and the rats were tested twice with the initial trial of SRT performed 1 h and 24 h after administration. The juvenile rat was presented twice with an inter-trial interval of 2 hours. In each experimental group data were obtained from 9 to 11 rats. Results are shown as Mean and SEM of recognition ratio (RR). A RR value significantly below 0.5 indicates social memory. Comparisons of RR values to a hypothetical value 0.50 were carried using one-sample t-test. **P<0.01.
Figure 4:
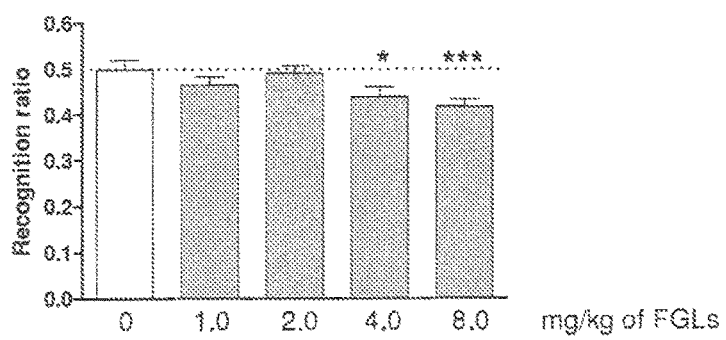

In the second study the rats received a single subcutaneous dose of 1.0, 2.0, 4.0 or 8.0 mg/kg of FGLs and were tested 1 hour and 24 hours after administration. A significant memory enhancing effect of 2.0, 4.0, and 8.0 mg/kg FGLs was detected 1 hour post administration, while a significant memory enhancing effect of 4.0 and 8.0 mg/kg FGLs was seen 24 hours after administration (FIG. 4).

Figure 5:
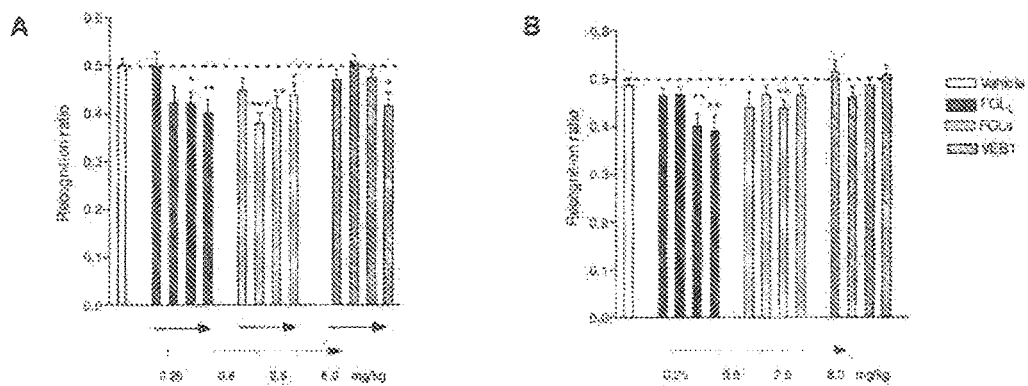
FIG. 5. Effects of subcutaneous administration of FGLs, $FGL_L$ and VEB1 (2 administrations at the stated doses) on short-term social memory as evaluated in the Social Recognition Test (SRT). Results are shown as Mean and SEM of recognition ratio (RR). A RR value significantly below 0.5 indicates social memory. Comparisons of RR values to a hypothetical value 0.50 were carried using one-sample t-test.

In the third study the dose response effects (0.25, 0.80, 2.50 and 8.0 mg/kg) of subcutaneous administration of FGLs were tested. In parallel were also tested $FGL_L$ and VEB1, another truncated form of $FGL_L$. The peptides were administered twice, 24 and 5 hours before the first SRT, and the rats were tested 5 hour and 77 hours after the last administration 5 hours post administration the minimum effective dose for FGLs was 0.80 mg/kg, for $FGL_L$ was 2.50 mg/kg, while for VEB1 was 8.0 mg/kg (FIG. 4A). 77 hours post administration the effects of both $FGL_L$ and FGLs in enhancing social memory were still significant at 2.50 mg/kg, with $FGL_L$ been also effective at 8.0 mg/kg. VEB1 administration did not produce long-lasting social memory enhancing effects (FIG. 5B).

The 11 amino acid form, FGLs has mnemotropic properties similar to those of full length $FGL_L$. FGLs subcutaneous administration enhances short-term social memory with the mnemotropic effects lasting at least 72 hours after administration. The minimum effective dose of FGLs in the SRT in intact rats was 0.8 mg/kg and for $FGL_L$ was 2.5 mg/kg, suggesting an higher bioavailability of the more soluble FGLs in comparison with $FGL_L$.

4. A Study of the Effect of Subcutaneous Administration of FGLs on Spatial Learning Evaluated Using the Morris Water Maze.

The aim of this study was to investigate whether the subcutaneous administration of FGLs modulates spatial learning in adult male Wistar rats, using the Morris Water Maze as test system.

Figure 6:
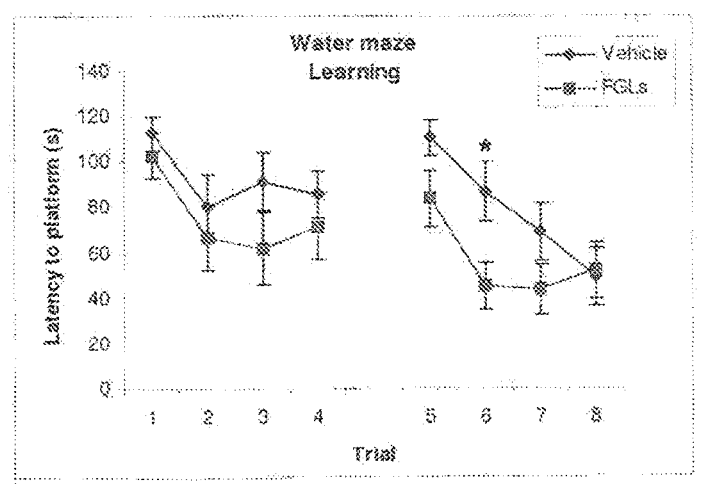

In the MWM test, rats are evaluated in the task to learn and remember the location of an escape platform hidden just under the water surface. In this study the test set-up was optimised for measuring learning. Rats received FGLs 2.5 mg/kg or vehicle subcutaneously as a single dose 5, 3 and 1 day prior the start of the training in the MWM. Rats treated with FGLs learned significantly faster than vehicle treated ones, indicating that FGLs administration facilitates spatial learning (FIG. 6).

Subcutaneous administration of FGLs significantly facilitated learning in Morris Water Maze, indicating a compound-dependent enhancement of motor learning. These results are comparable with those obtained with subcutaneous administration of $FGL_L$, when efficacy after subcutaneous administration was detected at 6.6 mg/kg.

5. A Randomised, Placebo Controlled Study of the Effect of Subcutaneous Administration of FGLs on Cognitive Impairment Induced by Scopolamine Treatment.

FGLs was tested for efficacy in the scopolamine induced social amnesia model in adult rats (Van Kampen et al., 2004). In parallel were also tested $FGL_L$ and VEB1, another truncated form of $FGL_L$. Rats received subcutaneously two consecutive doses of peptide (8 mg/kg) or vehicle with a 19 hours interval. Vehicle treated rats received the same volume of vehicle (sterile water). Testing was started 5 hours after the second administration of peptide and 30 minutes after administration of scopolamine (0.01 mg/kg subcutaneously).

When tested in the SRT, rats treated with scopolamine showed social amnesia since their RR was not significantly different from the theoretical value of 0.5. Scopolamine treated rats that received FGLs or $FGL_L$, had a RR significantly different from the theoretical value of 0.5 (p<0.05) suggesting that the treatment counteracted the social memory impairment induced by scopolamine. VEB1 administration did not produce significant effects (FIG. 7A).

Statistical analysis detected a significant difference in the cumulative investigation time at the first encounter of rats treated with scopolamine and vehicle versus rats treated with scopolamine and either FGLs or $FGL_L$ (p<0.05 both peptides), suggesting that peptide treatment increased the investigative activity of scopolamine treated rats when exposed for the first time to a novel juvenile. In contrast there was not significant difference in the cumulative investigation time at the second encounter among any of the scopolamine treated groups. VEB1 administration did not produce significant effects (FIG. 7B).

Treatment with scopolamine 0.01 mg/kg induced both social amnesia (as judged by statistical analysis of Recognition Ratios) and a significant reduction in investigative activity (as judged by comparison of T1). Treatment with both FGLs and $FGL_L$ ameliorated both parameters.

6. A Randomised, Placebo Controlled Study of the Effect of Subcutaneous Administration of FGLs on Cognitive Impairment and Neuropathology after Treatment of Rats with (25-35) β-Amyloid Fragment In the rat model of (25-35) β-amyloid induced neurotoxicity (Delobette et al., 1997; Maurice et al., 1996), (25-35) aggregated β-amyloid neurotoxin is injected intracerebroventricularly leading to progressive deterioration of short-term memory (clearly detectable using the Social Recognition Test (SRT) with a 30-minute inter-trial interval (ITI) (Kogan et al., 2000), and to neurodegeneration in cortex and hippocampus characterized by increases in amyloid burden, tau phosphorylation and micro- and macro-glia activation, as well as neuronal loss (Klementiev et al., 2007).

In this study, 3.2, 0.8, 0.2 mg/kg of FGLs or sterile PBS were administered daily by subcutaneous injection. Administration was started 7 days after i.c.v. administration of an aggregated form of the (25-35) β-amyloid peptide fragment and continued until day 28 when the rats were terminated.

The social memory performance was estimated, using the SRT 21-22 days after i.c.v. administration of the β-amyloid fragment. A statistically significantly impairment of the short-term memory was observed as a consequence of the (25-35) β-amyloid neurotoxicity in the rats receiving the (25-35) β-amyloid fragment plus vehicle, or plus the control peptide. Rats injected subcutaneously with FGLs at the dose of 0.8 mg/kg showed a statistically significant reduction in the short-term memory deficit compared to placebo-treated rats (FIG. 8A).

The results of the neuropathology investigations (28 days after the (25-35) β-amyloid injection, see Table 1) showed that the β-amyloid injection induced a significant loss of neurons and neuronal damage in the cingulate cortex (FIGS. 8B and C), and in hippocampus (CA3 area) as determined by stereological counting of neurons, as well as by an increased damage index. A significant neuroprotective effect of FGLs was detected in both areas. The minimum effective dose of FGLs for neuroprotection was 0.8 mg/kg, in hippocampus and 0.2 mg/kg in cingulate cortex. The β-amyloid injection caused an increased β-amyloid burden, and peptide treatment an amelioration of this pathology, however due to a large variability among animals both effects did not reach significance (FIG. 8D).

TABLE 1

Overview of results of subcutaneous administration of FGLs in the □-amyloid neurotoxicity model.

| TEST/END POINT | PRESENCE OF A SIGNIFICANT LESION EFFECT | PRESENCE OF A SIGNIFICANT PEPTIDE EFFECT | EFFECTIVE DOSE OR DOSE RANGE |
| --- | --- | --- | --- |
| SRT: short-term social recognition memory | YES (p < 0.05)[1] | YES (p < 0.01)[1] | 0.8 mg/kg |
| Density Intact neurons Hippocampus (CA3) | YES (p < 0.01)[2] | YES (P < 0.05) | 0.8 mg/kg |
| Density Intact neurons Cingulate cortex | YES (p < 0.01)[2] | Yes (p < 0.05)[3] | 0.8 mg/kg |
| Density damaged neurons Hippocampus (CA3) | YES (p < 0.01)[2] | YES (p < 0.05)[3] | 0.8 mg/kg |
| Density damaged neurons Cingulate cortex | YES (p < 0.001)[2] | YES (p < 0.01, p < 0.001)[3] | 0.2 mg/kg |

[1]Comparisons of RR values to a hypothetical value 0.50 were carried using one-sample t-test.
[2]differences between sham operated animals (rats that had received an i.c.v. injection of sterile water and had received subcutaneously drug vehicle) and β-amyloid treated rats that had received subcutaneously drug vehicle were analyzed by un-paired t-test.
[3]differences between β-amyloid treated rats that had received subcutaneously drug vehicle and β-amyloid treated rats that had been treated with different doses of FGLs, were analyzed by One Way ANOVA followed by Newman-Keuls post hoc test.

The results of this study show efficacy of FGLs after subcutaneous administration in ameliorating the social recognition memory deficit caused by □-amyloid neurotoxicity, with a minimum effective dose of 0.8 mg/kg. For neuroprotection the minimum effective dose was 0.2 mg/kg.

7. A Randomised, Placebo-Controlled Study of the Dose-Response Effect of Intranasal Administration of FGLs on Cognitive Impairment after Treatment with (25-35) β-Amyloid Fragment In this study, the (25-35) β-amyloid peptide fragment induced cognitive deficits model in rats was used to investigate the dose-response (0.08, 0.32 or 1.28 mg/kg) effect of FGLs administered intranasally daily for 15 doses from day 7 to day 21 post β-amyloid peptide i.c.v. injection. The social memory performance was evaluated using the SRT, 22 days after the β-amyloid injection. A statistically significant impairment of short-term memory was observed as a consequence of the (25-35) β-amyloid neurotoxicity in the rats receiving the (25-35) β-amyloid fragment plus vehicle. The β-amyloid injected rats treated intranasally with 1.28 mg/kg FGLs showed a significant (p<0.01) amelioration of the deficit in their social memory performance (FIG. 9), when compared with vehicle treated rats.

FGL intranasal administration (as $FGL_L$) significantly ameliorated impaired short-term memory, as reflected by improved performance of the Social Recognition Test. The minimum effective dose with the present protocol of administration (15 daily doses from day 7 to 21 and test 24 hrs after the last administration) was 1.28 mg/kg.

Samples of blood plasma were obtained 30 and 60 minutes after the last administration. The time-course of FGLs concentrations in plasma in were studied. The concentration of FGFs in blood plasma after peptide administration can be seen in FIG. 10.

8. Visual a Appearance of $FGF_L$ and FGFs Diluted in Water.

$FGF_L$ and FGFs were diluted in water at a concentration of 100 mg/ml for visual inspection (FIG. 11). The $FGL_L$ solution became a turbid hard gel, whereas the FGFs solution remained clear. In another experiment were 5 mg of $FGL_L$ and FGLs respectively diluted in 1 ml water or PBS at room temperature. Light microscopy pictures of the water and PBS solutions of $FGL_L$ and FGLs can be seen in FIG. 12. In FIG. 13. is a 90° light-scattering spectra of 100 mg/ml $FGF_L$ and FGLs in water showing the difference in intensity between the $FGF_L$ and the FGLs, solution.

9. FGLs Concentration in Plasma after i.v and s.c Administration.

The time-course of FGLs concentrations in plasma in intact rats after intravenous and subcutaneous administration were studied. A single dose of 1.25 mg/kg of FGLs were administered by intravenous injection or 2.5 mg/kg by subcutaneous injection. Blood samples were collected at different time points after the FGLs administration. The concentration of FGLs was measured using an ELISA assay and polyclonal rabbit anti-FGL antibodies. The concentration of FGFs in blood plasma after peptide administration can be seen in FIG. 14.

10. Preparation of Compounds According to the Invention.

Compounds comprising the following sequences were produced according to the method described below (and see FIG. 15 flowchart):

Peptide sequences:

VAENQQGKSKA

EVVAENQQGKSKA

NVVAENQQGKSKA

NSVAENQQGKSKA

Exemplified by the production of a compound of the structural formula:

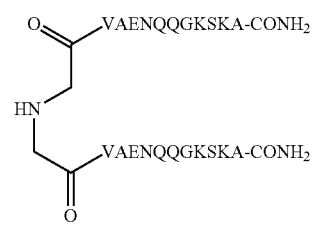

It consists of two identical 11 amino acid peptides, forming a dimer through a linker molecule.

Solid Phase Synthesis

The peptide chain is synthesized by the standard Fmoc-solid phase method. The solid phase synthesis is performed on Tentagel resin with a Rink amide linker, to which the first (C-terminal) amino acid is attached. The amino acids are coupled one at a time alternating with removal of Fmoc-groups. The amino acid derivatives used are, (in the following order):

Fmoc-Ala-OH
Fmoc-Lys(Boc)-OH
Fmoc-Ser(tBu)-OH
Fmoc-Lys(Boc)-OH
Fmoc-Gly-OH
Fmoc-Gln(Trt)-OH
Fmoc-Gln(Trt)-OH
Fmoc-Asn(Trt)-OH
Fmoc-Glu(OtBu)-OH
Fmoc-Ala-OH
Fmoc-Val-OH The Fmoc-amino acids are preactivated in DMF by TBTU/HOBt and then coupled to the growing peptide-resin. For the removal of Fmoc-groups piperidine in DMF is used. At the end of the solid phase synthesis, the peptide resin looks as follows:

```
Val-Ala-Glu(OtBu)-Asn(Trt)-Gln(Trt)-Gln(Trt)-

Gly-Lys(Boc)-Ser(tBu)-Lys(Boc)-Ala-R
```

Dimerisation

The dimer is created by coupling Boc-iminodiacetic acid to the peptide on the resin, using TBTU/HOBt in NMP, after removal of the Fmoc-group with Piperidine/DMF. To reduce sidereactions multiple coupling are performed with Boc-iminodiacetic acid as the limiting component.

Cleavage

The peptide is simultaneously cleaved from the resin and deprotected on the side chains in TFA with water as scavenger to yield the peptide amide:

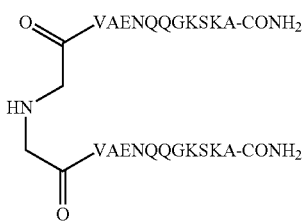

The peptide is purified in two chromatographic steps, ion exchanged to remove TFA-ions, and finally isolated by lyophilisation.

Starting materials, reagents and solvents used in the production of FGLs

Acetic acid
Acetic acid anhydride
O-(Benzotriazol-1-yl)-N,N,N',N'-tetramethyluronium tetrafluoroborate (TBTU)
Boc iminodiacetic acid
Dimethylformamide
Ethanol, 99,9%
Ethylacetate
N-Ethyl-diisopropylamine
Fmoc-Ala-OH
Fmoc-Asn(Trt)-OH
Fmoc-Gln(Trt)-OH
Fmoc-Glu(OtBu)-OH
Fmoc-Gly-OH
Fmoc-Lys(Boc)-OH
Fmoc-Ser(tBu)-OH
Fmoc-Val-OH
HCl
1-Hydroxybenzotriazol
Isopropanol
N-methylpyrrolidone
NaOH
$NH_4Ac$
Piperidine
Tentagel SRAM resin
Toluene
Trifluoroacetic acid Abbreviations Abbreviations for amino acids are in accordance with the recommendations in the IUPAC-IUB Joint Commission on Biochemical Nomenclature Eur. J. Biochem, 1984, vol. 184, pp 9-37

Other abbreviations are:
AA Amino acid
AcOH Acetic acid
Boc N-tert-Butyloxycarbonyl
DIPEA N-Ethyl-diisopropylamine
DMF Dimethylformamide
EtOH Ethanol, 99,9%
Fmoc 9-Fluorenylmethyloxycarbonyl
HOBt 1-Hydroxybenzotriazol
HPLC High pressure liquid chromatography
Ida Iminodiacetic acid
NMP N-methylpyrrolidone
R Amide-TG-resin
tBu tert-Butyl
TFA Trifluoroacetic acid
TBTU O-(Benzotriazol-1-yl)-N,N,N',N'-tetramethyluronium tetrafluoroborate

REFERENCES

Berezin V, Bock E and Poulsen F M (2000). The neural cell adhesion molecule. *Current Opinion in Drug Discovery & Development* 3:605-609.

Bruses J L, Rutishauser U (2001). Roles, regulation, and mechanism of polysialic acid function during neural development. *Biochemie* 83:635-643.

Cremer H, Chazal G, Goridis C, Represa A (1997). NCAM is essential for axonal growth and fasciculation in the hippocampus. *Mol Cell Neurosci.* 8:323-335.

Dantzer R, Bluthe R M, Koob G F, Le Moal M (1987). Modulation of social memory in male rats by neurohypophyseal peptides. *Psychopharmacology* (Berl) 91:363-368.

Delobette S, Privat A, Maurice T (1997). In vitro aggregation facilities beta-amyloid peptide-(25-35)-induced amnesia in the rat. *Eur J Pharmacol.* 319:1-4.

Doherty P and Walsh F S (1996). CAM-FGF Receptor Interactions: A Model for Axonal Growth. *Mol Cell Neurosci.* 8:99-111.

Kiselyov V V, Skladchikova G, Hinsby A M, Jensen P H, Kulahin N, Soroka V, Pedersen N, Tsetlin V, Poulsen F M, Berezin V, Bock E (2003). Structural basis for a direct interaction between FGFR1 and NCAM and evidence for a regulatory role of ATP. *Structure* 11:691-701.

Klementiev B, Novikova T, Novitskaya V, Walmod P S, Dmytriyeva O, Pakkenberg B, Berezin V, Bock E (2007). A neural cell adhesion molecule-derived peptide reduces neuropathological signs and cognitive impairment induced by Abeta(25-35). *Neuroscience* 145:209-224.

Kogan J H, Frankland P W, Silva A J (2000). Long-term memory underlying hippocampus-dependent social recognition in mice. *Hippocampus* 10:47-56.

Maurice T, Lockhart B P, Privat A (1996). Amnesia induced in mice by centrally administered beta-amyloid peptides involves cholinergic dysfunction. *Brain Res.* 706:181-193.

Rougon G, Hobert O (2003). New insights into the diversity and function of neuronal immunoglobulin superfamily molecules. *Annu Rev Neurosci.* 26:207-238.

Secher T, Novitskaia V, Berezin V, Bock E, Glenthoj B, Klementiev B (2006). A neural cell adhesion molecule-derived fibroblast growth factor receptor agonist, the FGL-peptide, promotes early postnatal sensorimotor development and enhances social memory retention. *Neuroscience* 141:1289-1299.

Van Kampen M, Selbach K, Schneider R, Schiegel E, Boess F, Schreiber R (2004). AR-R 17779 improves social recognition in rats by activation of nicotinic alpha7 receptors. *Psychopharmacology* (Berl) 172:375-383.

Walmod P S, Kolkova K, Berezin V, Bock E (2004). Zippers make signals: NCAM-mediated molecular interactions and signal transduction. *Neurochem Res.* 29:2015-2035.

The invention claimed is:

1. A compound comprising the formula $(Z_n-L_m)_q$, wherein
   Z is an individually selected peptide comprising the sequence QQGKSKA (amino acids 5-11 of SEQ ID NO:1),
   wherein Z is at most 13 contiguous amino acid residues,
   L is individually selected from the group consisting of lipophilic substituents, linkers, optionally substituted, and spacers, optionally substituted,
   n is an individually selected integer from 1 to 6,
   m is an individually selected integer from 0 to 6,
   q is an individually selected integer from 1 to 4,
   or a pharmaceutically acceptable salt thereof, wherein said peptide is capable of binding to an FGFR and thereby stimulating FGFR signaling.

2. The compound according to claim 1 wherein at least one L is a linker.

3. The compound according to claim 1 wherein at least one L is a spacer selected from the group consisting of beta-alanine, gamma-aminobutyric acid (GABA), gamma-glutamic acid, lysine, aspartic acid, glutamic acid, a dipeptide containing aspartic acid, a dipeptide containing glutamic acid, or a dipeptide containing lysine or quadrature-glutamic acid.

4. The compound according to claim 1 wherein at least one L is a lipophilic substituent selected from the group consisting of a partially or completely hydrogenated cyclopentanophenathrene skeleton, a straight-chain or branched alkyl group and the acyl group of a straight-chain or branched fatty acid.

5. The compound according to claim 1, consisting of a peptide comprising at most 13 contiguous amino acid residues derived from the fibronectin type 3, II module of NCAM.

6. The compound according to claim 1, wherein said peptide is selected from the group consisting of

| | |
|---|---|
| VAENQQGKSKA | (SEQ ID NO: 1) |
| EVVAENQQGKSKA | (SEQ ID NO: 2) |
| NVVAENQQGKSKA and | (SEQ ID NO: 3) |
| NSVAENQQGKSKA, | (SEQ ID NO: 4) | or a fragment or a variant thereof, wherein said variant comprises at least one amino acid substitution.

7. The compound according to claim 1, wherein said peptide is capable of stimulating neurite outgrowth, stimulating cell survival and/or stimulating synaptic plasticity.

8. The compound according to claim 1, wherein said peptide is capable of stimulating learning and/or memory.

9. The compound according to claim 1, wherein the compound is formulated as a monomer consisting of a single copy of the peptide.

10. The compound according to claim 1, wherein the compound is formulated as a dimer comprising two identical copies of the peptide or formulated as a trimer comprising three identical copies of the peptide.

11. The compound according to claim 1, wherein the compound is formulated as a dimer comprising two different peptide sequences or as a trimer comprising at least two different peptide sequences, wherein at least one of the peptide sequences is as defined in claim 1.

12. The compound according to claim 1, wherein the compound is formulated as a dendrimer comprising four or more identical copies of the peptide.

13. A pharmaceutically safe composition comprising at least one compound according to claim 1.

14. A method for treatment of diseases or conditions wherein modulation of FGFR signalling is essential, comprising administering an amount, effective for such treatment, of the compound according to claim 1 to an individual in need thereof.

15. A method for treatment of diseases or conditions of the central or peripheral nervous system, comprising administering an amount, effective for such treatment, of the compound according to claim 1 to an individual in need thereof.

16. A method for treatment of a disease or condition wherein stimulation of neural cell differentiation, neural cell survival, neurogenesis, neurite outgrowth, stem cell proliferation, stem cell differentiation, and/or learning and memory is beneficial for recovery from said disease or condition, comprising administering an amount, effective for such treatment, of the compound according to claim 1 to an individual in need thereof.

17. The method according to claim 15, wherein said disease or condition is Alzheimer's disease.

18. A method for stimulation of the ability to learn and/or of the short and/or long term memory, comprising administering a learning- or memory-stimulating amount of the compound according to claim 1 to an individual in need thereof.

19. A method of stimulating FGFR signaling in a subject which comprises administering to a subject a stimulatory amount of a compound according to claim 1.

20. The method of claim 19 in which the subject is suffering from a disease or condition of the central or peripheral nervous system.

21. The method of claim 19 in which the subject is suffering from a deficit in learning and/or memory.

22. The method of claim 19 in which the subject is suffering from Alzheimer's disease.

* * * * *

```
                        SEQUENCE LISTING

<160> NUMBER OF SEQ ID NOS: 73

<210> SEQ ID NO 1
<211> LENGTH: 11
<212> TYPE: PRT
<213> ORGANISM: Artificial sequence
<220> FEATURE:
<223> OTHER INFORMATION: Derived from NCAM

<400> SEQUENCE: 1

Val Ala Glu Asn Gln Gln Gly Lys Ser Lys Ala
1               5                   10

<210> SEQ ID NO 2
<211> LENGTH: 13
<212> TYPE: PRT
<213> ORGANISM: Artificial sequence
<220> FEATURE:
<223> OTHER INFORMATION: homologue

<400> SEQUENCE: 2

Glu Val Val Ala Glu Asn Gln Gln Gly Lys Ser Lys Ala
1               5                   10

<210> SEQ ID NO 3
<211> LENGTH: 13
<212> TYPE: PRT
<213> ORGANISM: Artificial sequence
<220> FEATURE:
<223> OTHER INFORMATION: homologue

<400> SEQUENCE: 3

Asn Val Val Ala Glu Asn Gln Gln Gly Lys Ser Lys Ala
1               5                   10

<210> SEQ ID NO 4
<211> LENGTH: 13
<212> TYPE: PRT
<213> ORGANISM: Artificial sequence
<220> FEATURE:
<223> OTHER INFORMATION: homologue

<400> SEQUENCE: 4

Asn Ser Val Ala Glu Asn Gln Gln Gly Lys Ser Lys Ala
1               5                   10

<210> SEQ ID NO 5
<211> LENGTH: 12
<212> TYPE: PRT
<213> ORGANISM: Artificial sequence
<220> FEATURE:
<223> OTHER INFORMATION: homologue
```

```
<400> SEQUENCE: 5

Ala Val Ala Glu Asn Gln Gln Gly Lys Ser Lys Ala
1               5                   10

<210> SEQ ID NO 6
<211> LENGTH: 12
<212> TYPE: PRT
<213> ORGANISM: Artificial sequence
<220> FEATURE:
<223> OTHER INFORMATION: homologue

<400> SEQUENCE: 6

Gly Val Ala Glu Asn Gln Gln Gly Lys Ser Lys Ala
1               5                   10

<210> SEQ ID NO 7
<211> LENGTH: 12
<212> TYPE: PRT
<213> ORGANISM: Artificial sequence
<220> FEATURE:
<223> OTHER INFORMATION: homologue

<400> SEQUENCE: 7

Leu Val Ala Glu Asn Gln Gln Gly Lys Ser Lys Ala
1               5                   10

<210> SEQ ID NO 8
<211> LENGTH: 12
<212> TYPE: PRT
<213> ORGANISM: Artificial sequence
<220> FEATURE:
<223> OTHER INFORMATION: homologue

<400> SEQUENCE: 8

Met Val Ala Glu Asn Gln Gln Gly Lys Ser Lys Ala
1               5                   10

<210> SEQ ID NO 9
<211> LENGTH: 12
<212> TYPE: PRT
<213> ORGANISM: Artificial sequence
<220> FEATURE:
<223> OTHER INFORMATION: homologue

<400> SEQUENCE: 9

Val Val Ala Glu Asn Gln Gln Gly Lys Ser Lys Ala
1               5                   10

<210> SEQ ID NO 10
<211> LENGTH: 12
<212> TYPE: PRT
<213> ORGANISM: Artificial sequence
<220> FEATURE:
<223> OTHER INFORMATION: homologue

<400> SEQUENCE: 10

Pro Val Ala Glu Asn Gln Gln Gly Lys Ser Lys Ala
1               5                   10

<210> SEQ ID NO 11
<211> LENGTH: 12
<212> TYPE: PRT
<213> ORGANISM: Artificial sequence
<220> FEATURE:
<223> OTHER INFORMATION: homologue

<400> SEQUENCE: 11
```

-continued

Ile Val Ala Glu Asn Gln Gln Gly Lys Ser Lys Ala
1               5                   10

<210> SEQ ID NO 12
<211> LENGTH: 13
<212> TYPE: PRT
<213> ORGANISM: Artificial sequence
<220> FEATURE:
<223> OTHER INFORMATION: homologue

<400> SEQUENCE: 12

Gln Ala Val Ala Glu Asn Gln Gln Gly Lys Ser Lys Ala
1               5                   10

<210> SEQ ID NO 13
<211> LENGTH: 13
<212> TYPE: PRT
<213> ORGANISM: Artificial sequence
<220> FEATURE:
<223> OTHER INFORMATION: homologue

<400> SEQUENCE: 13

Gln Gly Val Ala Glu Asn Gln Gln Gly Lys Ser Lys Ala
1               5                   10

<210> SEQ ID NO 14
<211> LENGTH: 13
<212> TYPE: PRT
<213> ORGANISM: Artificial sequence
<220> FEATURE:
<223> OTHER INFORMATION: homologue

<400> SEQUENCE: 14

Gln Leu Val Ala Glu Asn Gln Gln Gly Lys Ser Lys Ala
1               5                   10

<210> SEQ ID NO 15
<211> LENGTH: 13
<212> TYPE: PRT
<213> ORGANISM: Artificial sequence
<220> FEATURE:
<223> OTHER INFORMATION: homologue

<400> SEQUENCE: 15

Gln Met Val Ala Glu Asn Gln Gln Gly Lys Ser Lys Ala
1               5                   10

<210> SEQ ID NO 16
<211> LENGTH: 13
<212> TYPE: PRT
<213> ORGANISM: Artificial sequence
<220> FEATURE:
<223> OTHER INFORMATION: homologue

<400> SEQUENCE: 16

Gln Val Val Ala Glu Asn Gln Gln Gly Lys Ser Lys Ala
1               5                   10

<210> SEQ ID NO 17
<211> LENGTH: 13
<212> TYPE: PRT
<213> ORGANISM: Artificial sequence
<220> FEATURE:
<223> OTHER INFORMATION: homologue

<400> SEQUENCE: 17

Gln Pro Val Ala Glu Asn Gln Gln Gly Lys Ser Lys Ala
1               5                   10

```
<210> SEQ ID NO 18
<211> LENGTH: 13
<212> TYPE: PRT
<213> ORGANISM: Artificial sequence
<220> FEATURE:
<223> OTHER INFORMATION: homologue

<400> SEQUENCE: 18

Gln Ile Val Ala Glu Asn Gln Gln Gly Lys Ser Lys Ala
1               5                   10

<210> SEQ ID NO 19
<211> LENGTH: 13
<212> TYPE: PRT
<213> ORGANISM: Artificial sequence
<220> FEATURE:
<223> OTHER INFORMATION: homologue

<400> SEQUENCE: 19

Asn Ala Val Ala Glu Asn Gln Gln Gly Lys Ser Lys Ala
1               5                   10

<210> SEQ ID NO 20
<211> LENGTH: 13
<212> TYPE: PRT
<213> ORGANISM: Artificial sequence
<220> FEATURE:
<223> OTHER INFORMATION: homologue

<400> SEQUENCE: 20

Asn Gly Val Ala Glu Asn Gln Gln Gly Lys Ser Lys Ala
1               5                   10

<210> SEQ ID NO 21
<211> LENGTH: 13
<212> TYPE: PRT
<213> ORGANISM: Artificial sequence
<220> FEATURE:
<223> OTHER INFORMATION: homologue

<400> SEQUENCE: 21

Asn Leu Val Ala Glu Asn Gln Gln Gly Lys Ser Lys Ala
1               5                   10

<210> SEQ ID NO 22
<211> LENGTH: 13
<212> TYPE: PRT
<213> ORGANISM: Artificial sequence
<220> FEATURE:
<223> OTHER INFORMATION: homologue

<400> SEQUENCE: 22

Asn Met Val Ala Glu Asn Gln Gln Gly Lys Ser Lys Ala
1               5                   10

<210> SEQ ID NO 23
<211> LENGTH: 13
<212> TYPE: PRT
<213> ORGANISM: Artificial sequence
<220> FEATURE:
<223> OTHER INFORMATION: homologue

<400> SEQUENCE: 23

Asn Val Val Ala Glu Asn Gln Gln Gly Lys Ser Lys Ala
1               5                   10
```

```
<210> SEQ ID NO 24
<211> LENGTH: 13
<212> TYPE: PRT
<213> ORGANISM: Artificial sequence
<220> FEATURE:
<223> OTHER INFORMATION: homologue

<400> SEQUENCE: 24

Asn Pro Val Ala Glu Asn Gln Gln Gly Lys Ser Lys Ala
1               5                   10

<210> SEQ ID NO 25
<211> LENGTH: 13
<212> TYPE: PRT
<213> ORGANISM: Artificial sequence
<220> FEATURE:
<223> OTHER INFORMATION: homologue

<400> SEQUENCE: 25

Asn Ile Val Ala Glu Asn Gln Gln Gly Lys Ser Lys Ala
1               5                   10

<210> SEQ ID NO 26
<211> LENGTH: 13
<212> TYPE: PRT
<213> ORGANISM: Artificial sequence
<220> FEATURE:
<223> OTHER INFORMATION: homologue

<400> SEQUENCE: 26

Ser Ala Val Ala Glu Asn Gln Gln Gly Lys Ser Lys Ala
1               5                   10

<210> SEQ ID NO 27
<211> LENGTH: 13
<212> TYPE: PRT
<213> ORGANISM: Artificial sequence
<220> FEATURE:
<223> OTHER INFORMATION: homologue

<400> SEQUENCE: 27

Ser Gly Val Ala Glu Asn Gln Gln Gly Lys Ser Lys Ala
1               5                   10

<210> SEQ ID NO 28
<211> LENGTH: 13
<212> TYPE: PRT
<213> ORGANISM: Artificial sequence
<220> FEATURE:
<223> OTHER INFORMATION: homologue

<400> SEQUENCE: 28

Ser Leu Val Ala Glu Asn Gln Gln Gly Lys Ser Lys Ala
1               5                   10

<210> SEQ ID NO 29
<211> LENGTH: 13
<212> TYPE: PRT
<213> ORGANISM: Artificial sequence
<220> FEATURE:
<223> OTHER INFORMATION: homologue

<400> SEQUENCE: 29

Ser Met Val Ala Glu Asn Gln Gln Gly Lys Ser Lys Ala
1               5                   10

<210> SEQ ID NO 30
<211> LENGTH: 13
```

```
<212> TYPE: PRT
<213> ORGANISM: Artificial sequence
<220> FEATURE:
<223> OTHER INFORMATION: homologue

<400> SEQUENCE: 30

Ser Val Val Ala Glu Asn Gln Gln Gly Lys Ser Lys Ala
1               5                   10

<210> SEQ ID NO 31
<211> LENGTH: 13
<212> TYPE: PRT
<213> ORGANISM: Artificial sequence
<220> FEATURE:
<223> OTHER INFORMATION: homologue

<400> SEQUENCE: 31

Ser Pro Val Ala Glu Asn Gln Gln Gly Lys Ser Lys Ala
1               5                   10

<210> SEQ ID NO 32
<211> LENGTH: 13
<212> TYPE: PRT
<213> ORGANISM: Artificial sequence
<220> FEATURE:
<223> OTHER INFORMATION: homologue

<400> SEQUENCE: 32

Ser Ile Val Ala Glu Asn Gln Gln Gly Lys Ser Lys Ala
1               5                   10

<210> SEQ ID NO 33
<211> LENGTH: 13
<212> TYPE: PRT
<213> ORGANISM: Artificial sequence
<220> FEATURE:
<223> OTHER INFORMATION: homologue

<400> SEQUENCE: 33

Thr Ala Val Ala Glu Asn Gln Gln Gly Lys Ser Lys Ala
1               5                   10

<210> SEQ ID NO 34
<211> LENGTH: 13
<212> TYPE: PRT
<213> ORGANISM: Artificial sequence
<220> FEATURE:
<223> OTHER INFORMATION: homologue

<400> SEQUENCE: 34

Thr Gly Val Ala Glu Asn Gln Gln Gly Lys Ser Lys Ala
1               5                   10

<210> SEQ ID NO 35
<211> LENGTH: 13
<212> TYPE: PRT
<213> ORGANISM: Artificial sequence
<220> FEATURE:
<223> OTHER INFORMATION: homologue

<400> SEQUENCE: 35

Thr Leu Val Ala Glu Asn Gln Gln Gly Lys Ser Lys Ala
1               5                   10

<210> SEQ ID NO 36
<211> LENGTH: 13
<212> TYPE: PRT
<213> ORGANISM: Artificial sequence
```

```
<220> FEATURE:
<223> OTHER INFORMATION: homologue

<400> SEQUENCE: 36

Thr Met Val Ala Glu Asn Gln Gln Gly Lys Ser Lys Ala
1               5                   10

<210> SEQ ID NO 37
<211> LENGTH: 13
<212> TYPE: PRT
<213> ORGANISM: Artificial sequence
<220> FEATURE:
<223> OTHER INFORMATION: homologue

<400> SEQUENCE: 37

Thr Val Val Ala Glu Asn Gln Gln Gly Lys Ser Lys Ala
1               5                   10

<210> SEQ ID NO 38
<211> LENGTH: 13
<212> TYPE: PRT
<213> ORGANISM: Artificial sequence
<220> FEATURE:
<223> OTHER INFORMATION: homologue

<400> SEQUENCE: 38

Thr Pro Val Ala Glu Asn Gln Gln Gly Lys Ser Lys Ala
1               5                   10

<210> SEQ ID NO 39
<211> LENGTH: 13
<212> TYPE: PRT
<213> ORGANISM: Artificial sequence
<220> FEATURE:
<223> OTHER INFORMATION: homologue

<400> SEQUENCE: 39

Thr Ile Val Ala Glu Asn Gln Gln Gly Lys Ser Lys Ala
1               5                   10

<210> SEQ ID NO 40
<211> LENGTH: 13
<212> TYPE: PRT
<213> ORGANISM: Artificial sequence
<220> FEATURE:
<223> OTHER INFORMATION: homologue

<400> SEQUENCE: 40

Gly Ala Val Ala Glu Asn Gln Gln Gly Lys Ser Lys Ala
1               5                   10

<210> SEQ ID NO 41
<211> LENGTH: 13
<212> TYPE: PRT
<213> ORGANISM: Artificial sequence
<220> FEATURE:
<223> OTHER INFORMATION: homologue

<400> SEQUENCE: 41

Gly Gly Val Ala Glu Asn Gln Gln Gly Lys Ser Lys Ala
1               5                   10

<210> SEQ ID NO 42
<211> LENGTH: 13
<212> TYPE: PRT
<213> ORGANISM: Artificial sequence
<220> FEATURE:
<223> OTHER INFORMATION: homologue
```

```
<400> SEQUENCE: 42

Gly Leu Val Ala Glu Asn Gln Gln Gly Lys Ser Lys Ala
1               5                   10

<210> SEQ ID NO 43
<211> LENGTH: 13
<212> TYPE: PRT
<213> ORGANISM: Artificial sequence
<220> FEATURE:
<223> OTHER INFORMATION: homologue

<400> SEQUENCE: 43

Gly Met Val Ala Glu Asn Gln Gln Gly Lys Ser Lys Ala
1               5                   10

<210> SEQ ID NO 44
<211> LENGTH: 13
<212> TYPE: PRT
<213> ORGANISM: Artificial sequence
<220> FEATURE:
<223> OTHER INFORMATION: homologue

<400> SEQUENCE: 44

Gly Val Val Ala Glu Asn Gln Gln Gly Lys Ser Lys Ala
1               5                   10

<210> SEQ ID NO 45
<211> LENGTH: 13
<212> TYPE: PRT
<213> ORGANISM: Artificial sequence
<220> FEATURE:
<223> OTHER INFORMATION: homologue

<400> SEQUENCE: 45

Gly Pro Val Ala Glu Asn Gln Gln Gly Lys Ser Lys Ala
1               5                   10

<210> SEQ ID NO 46
<211> LENGTH: 13
<212> TYPE: PRT
<213> ORGANISM: Artificial sequence
<220> FEATURE:
<223> OTHER INFORMATION: homologue

<400> SEQUENCE: 46

Gly Ile Val Ala Glu Asn Gln Gln Gly Lys Ser Lys Ala
1               5                   10

<210> SEQ ID NO 47
<211> LENGTH: 13
<212> TYPE: PRT
<213> ORGANISM: Artificial sequence
<220> FEATURE:
<223> OTHER INFORMATION: homologue

<400> SEQUENCE: 47

Asp Ala Val Ala Glu Asn Gln Gln Gly Lys Ser Lys Ala
1               5                   10

<210> SEQ ID NO 48
<211> LENGTH: 13
<212> TYPE: PRT
<213> ORGANISM: Artificial sequence
<220> FEATURE:
<223> OTHER INFORMATION: homologue

<400> SEQUENCE: 48
```

Asp Gly Val Ala Glu Asn Gln Gln Gly Lys Ser Lys Ala
1               5                   10

<210> SEQ ID NO 49
<211> LENGTH: 13
<212> TYPE: PRT
<213> ORGANISM: Artificial sequence
<220> FEATURE:
<223> OTHER INFORMATION: homologue

<400> SEQUENCE: 49

Asp Leu Val Ala Glu Asn Gln Gln Gly Lys Ser Lys Ala
1               5                   10

<210> SEQ ID NO 50
<211> LENGTH: 13
<212> TYPE: PRT
<213> ORGANISM: Artificial sequence
<220> FEATURE:
<223> OTHER INFORMATION: homologue

<400> SEQUENCE: 50

Asp Met Val Ala Glu Asn Gln Gln Gly Lys Ser Lys Ala
1               5                   10

<210> SEQ ID NO 51
<211> LENGTH: 13
<212> TYPE: PRT
<213> ORGANISM: Artificial sequence
<220> FEATURE:
<223> OTHER INFORMATION: homologue

<400> SEQUENCE: 51

Asp Val Val Ala Glu Asn Gln Gln Gly Lys Ser Lys Ala
1               5                   10

<210> SEQ ID NO 52
<211> LENGTH: 13
<212> TYPE: PRT
<213> ORGANISM: Artificial sequence
<220> FEATURE:
<223> OTHER INFORMATION: homologue

<400> SEQUENCE: 52

Asp Pro Val Ala Glu Asn Gln Gln Gly Lys Ser Lys Ala
1               5                   10

<210> SEQ ID NO 53
<211> LENGTH: 13
<212> TYPE: PRT
<213> ORGANISM: Artificial sequence
<220> FEATURE:
<223> OTHER INFORMATION: homologue

<400> SEQUENCE: 53

Asp Ile Val Ala Glu Asn Gln Gln Gly Lys Ser Lys Ala
1               5                   10

<210> SEQ ID NO 54
<211> LENGTH: 13
<212> TYPE: PRT
<213> ORGANISM: Artificial sequence
<220> FEATURE:
<223> OTHER INFORMATION: homologue

<400> SEQUENCE: 54

Glu Ala Val Ala Glu Asn Gln Gln Gly Lys Ser Lys Ala

```
1               5                   10
```

<210> SEQ ID NO 55
<211> LENGTH: 13
<212> TYPE: PRT
<213> ORGANISM: Artificial sequence
<220> FEATURE:
<223> OTHER INFORMATION: homologue

<400> SEQUENCE: 55

```
Glu Gly Val Ala Glu Asn Gln Gln Gly Lys Ser Lys Ala
1               5                   10
```

<210> SEQ ID NO 56
<211> LENGTH: 13
<212> TYPE: PRT
<213> ORGANISM: Artificial sequence
<220> FEATURE:
<223> OTHER INFORMATION: homologue

<400> SEQUENCE: 56

```
Glu Leu Val Ala Glu Asn Gln Gln Gly Lys Ser Lys Ala
1               5                   10
```

<210> SEQ ID NO 57
<211> LENGTH: 13
<212> TYPE: PRT
<213> ORGANISM: Artificial sequence
<220> FEATURE:
<223> OTHER INFORMATION: homologue

<400> SEQUENCE: 57

```
Glu Met Val Ala Glu Asn Gln Gln Gly Lys Ser Lys Ala
1               5                   10
```

<210> SEQ ID NO 58
<211> LENGTH: 13
<212> TYPE: PRT
<213> ORGANISM: Artificial sequence
<220> FEATURE:
<223> OTHER INFORMATION: homologue

<400> SEQUENCE: 58

```
Glu Pro Val Ala Glu Asn Gln Gln Gly Lys Ser Lys Ala
1               5                   10
```

<210> SEQ ID NO 59
<211> LENGTH: 13
<212> TYPE: PRT
<213> ORGANISM: Artificial sequence
<220> FEATURE:
<223> OTHER INFORMATION: homologue

<400> SEQUENCE: 59

```
Glu Ile Val Ala Glu Asn Gln Gln Gly Lys Ser Lys Ala
1               5                   10
```

<210> SEQ ID NO 60
<211> LENGTH: 13
<212> TYPE: PRT
<213> ORGANISM: Artificial sequence
<220> FEATURE:
<223> OTHER INFORMATION: homologue

<400> SEQUENCE: 60

```
Ala Asp Val Ala Glu Asn Gln Gln Gly Lys Ser Lys Ala
1               5                   10
```

<210> SEQ ID NO 61
<211> LENGTH: 13
<212> TYPE: PRT
<213> ORGANISM: Artificial sequence
<220> FEATURE:
<223> OTHER INFORMATION: homologue

<400> SEQUENCE: 61

Gly Asp Val Ala Glu Asn Gln Gln Gly Lys Ser Lys Ala
1               5                   10

<210> SEQ ID NO 62
<211> LENGTH: 13
<212> TYPE: PRT
<213> ORGANISM: Artificial sequence
<220> FEATURE:
<223> OTHER INFORMATION: homologue

<400> SEQUENCE: 62

Leu Asp Val Ala Glu Asn Gln Gln Gly Lys Ser Lys Ala
1               5                   10

<210> SEQ ID NO 63
<211> LENGTH: 13
<212> TYPE: PRT
<213> ORGANISM: Artificial sequence
<220> FEATURE:
<223> OTHER INFORMATION: homologue

<400> SEQUENCE: 63

Met Asp Val Ala Glu Asn Gln Gln Gly Lys Ser Lys Ala
1               5                   10

<210> SEQ ID NO 64
<211> LENGTH: 13
<212> TYPE: PRT
<213> ORGANISM: Artificial sequence
<220> FEATURE:
<223> OTHER INFORMATION: homologue

<400> SEQUENCE: 64

Val Asp Val Ala Glu Asn Gln Gln Gly Lys Ser Lys Ala
1               5                   10

<210> SEQ ID NO 65
<211> LENGTH: 13
<212> TYPE: PRT
<213> ORGANISM: Artificial sequence
<220> FEATURE:
<223> OTHER INFORMATION: homologue

<400> SEQUENCE: 65

Pro Asp Val Ala Glu Asn Gln Gln Gly Lys Ser Lys Ala
1               5                   10

<210> SEQ ID NO 66
<211> LENGTH: 13
<212> TYPE: PRT
<213> ORGANISM: Artificial sequence
<220> FEATURE:
<223> OTHER INFORMATION: homologue

<400> SEQUENCE: 66

Ile Asp Val Ala Glu Asn Gln Gln Gly Lys Ser Lys Ala
1               5                   10

<210> SEQ ID NO 67

<211> LENGTH: 13
<212> TYPE: PRT
<213> ORGANISM: Artificial sequence
<220> FEATURE:
<223> OTHER INFORMATION: homologue

<400> SEQUENCE: 67

Ala Glu Val Ala Glu Asn Gln Gln Gly Lys Ser Lys Ala
1               5                   10

<210> SEQ ID NO 68
<211> LENGTH: 13
<212> TYPE: PRT
<213> ORGANISM: Artificial sequence
<220> FEATURE:
<223> OTHER INFORMATION: homologue

<400> SEQUENCE: 68

Gly Glu Val Ala Glu Asn Gln Gln Gly Lys Ser Lys Ala
1               5                   10

<210> SEQ ID NO 69
<211> LENGTH: 13
<212> TYPE: PRT
<213> ORGANISM: Artificial sequence
<220> FEATURE:
<223> OTHER INFORMATION: homologue

<400> SEQUENCE: 69

Leu Glu Val Ala Glu Asn Gln Gln Gly Lys Ser Lys Ala
1               5                   10

<210> SEQ ID NO 70
<211> LENGTH: 13
<212> TYPE: PRT
<213> ORGANISM: Artificial sequence
<220> FEATURE:
<223> OTHER INFORMATION: homologue

<400> SEQUENCE: 70

Met Glu Val Ala Glu Asn Gln Gln Gly Lys Ser Lys Ala
1               5                   10

<210> SEQ ID NO 71
<211> LENGTH: 13
<212> TYPE: PRT
<213> ORGANISM: Artificial sequence
<220> FEATURE:
<223> OTHER INFORMATION: homologue

<400> SEQUENCE: 71

Val Glu Val Ala Glu Asn Gln Gln Gly Lys Ser Lys Ala
1               5                   10

<210> SEQ ID NO 72
<211> LENGTH: 13
<212> TYPE: PRT
<213> ORGANISM: Artificial sequence
<220> FEATURE:
<223> OTHER INFORMATION: homologue

<400> SEQUENCE: 72

Pro Glu Val Ala Glu Asn Gln Gln Gly Lys Ser Lys Ala
1               5                   10

<210> SEQ ID NO 73
<211> LENGTH: 13
<212> TYPE: PRT

```
<213> ORGANISM: Artificial sequence
<220> FEATURE:
<223> OTHER INFORMATION: homologue

<400> SEQUENCE: 73

Ile Glu Val Ala Glu Asn Gln Gln Gly Lys Ser Lys Ala
1               5                   10
```